United States Patent
Anryu et al.

(10) Patent No.: US 8,852,846 B2
(45) Date of Patent: *Oct. 7, 2014

(54) SALT AND PHOTORESIST COMPOSITION COMPRISING THE SAME

(75) Inventors: Yukako Anryu, Osaka (JP); Koji Ichikawa, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/439,478

(22) Filed: Apr. 4, 2012

(65) Prior Publication Data

US 2012/0258403 A1    Oct. 11, 2012

(30) Foreign Application Priority Data

Apr. 7, 2011    (JP) .................................. 2011-085490

(51) Int. Cl.

| | | |
|---|---|---|
| G03F 7/004 | (2006.01) | |
| G03F 7/38 | (2006.01) | |
| C07C 303/32 | (2006.01) | |
| C07D 277/06 | (2006.01) | |
| C07D 279/06 | (2006.01) | |
| C07D 281/06 | (2006.01) | |
| C07D 295/06 | (2006.01) | |
| C07D 279/12 | (2006.01) | |
| C07D 303/32 | (2006.01) | |
| G03F 7/039 | (2006.01) | |
| G03F 7/20 | (2006.01) | |

(52) U.S. Cl.
CPC ............ *C07D 279/12* (2013.01); *C07D 295/06* (2013.01); *C07D 277/06* (2013.01); *C07D 281/06* (2013.01); *C07D 279/06* (2013.01); *C07D 303/32* (2013.01); *G03F 7/0045* (2013.01); *G03F 7/0046* (2013.01); *G03F 7/0397* (2013.01); *G03F 7/2041* (2013.01); *Y10S 430/121* (2013.01); *Y10S 430/123* (2013.01)
USPC ........ 430/270.1; 430/326; 430/330; 430/920; 430/922; 540/467; 540/544; 544/53; 544/59; 548/146; 562/109; 562/113

(58) Field of Classification Search
CPC ... G03F 7/0045; G03F 7/0397; C07C 303/32; C07D 277/06; C07D 279/06; C07D 281/06; C07D 295/06
USPC .............. 430/270.1, 910, 920, 922, 326, 330; 544/59, 53; 562/109, 113; 540/544, 540/467; 548/122, 146

See application file for complete search history.

(56) References Cited

U.S. PATENT DOCUMENTS

| | | | | |
|---|---|---|---|---|
| 7,629,108 | B2 * | 12/2009 | Watanabe et al. | .......... 430/270.1 |
| 8,236,842 | B2 * | 8/2012 | Yoshida et al. | ................ 514/397 |
| 8,460,851 | B2 * | 6/2013 | Yamaguchi et al. | ....... 430/270.1 |
| 8,530,135 | B2 * | 9/2013 | Yamaguchi et al. | ....... 430/270.1 |
| 2002/0098443 | A1 * | 7/2002 | Hatakeyama et al. | ..... 430/270.1 |
| 2002/0102491 | A1 | 8/2002 | Kodama et al. | |
| 2007/0122750 | A1 | 5/2007 | Yamaguchi et al. | |
| 2008/0102405 | A1 * | 5/2008 | Watanabe et al. | .......... 430/283.1 |
| 2011/0171576 | A1 | 7/2011 | Yamaguchi et al. | |

* cited by examiner

*Primary Examiner* — John Chu
(74) *Attorney, Agent, or Firm* — Birch, Stewart, Kolasch & Birch, LLP

(57) ABSTRACT

The present invention provides a salt represented by the formula (I):

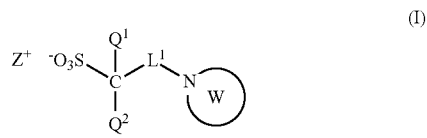

(I)

wherein $Q^1$ and $Q^2$ independently each represent a fluorine atom or a C1-C6 perfluoroalkyl group, $L^1$ represents a C1-C20 divalent saturated hydrocarbon group in which one or more —CH$_2$— can be replaced by —O— or —CO—, W represents a group represented by the formula (W1), (W2), (W3), (W4) or (W5):

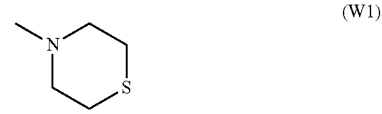

(W1)

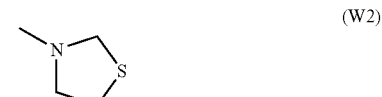

(W2)

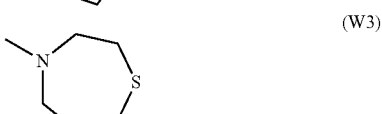

(W3)

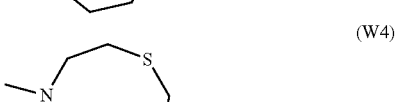

(W4)

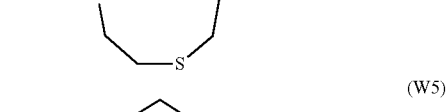

(W5)

and $Z^+$ represents an organic counter ion.

10 Claims, No Drawings

SALT AND PHOTORESIST COMPOSITION COMPRISING THE SAME

This nonprovisional application claims priority under 35 U.S.C. §119-(a) on Patent Application No. 2011-085490 filed in JAPAN on Apr. 7, 2011, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

US 2002/0102491 A1 discloses a salt represented by the following formula:

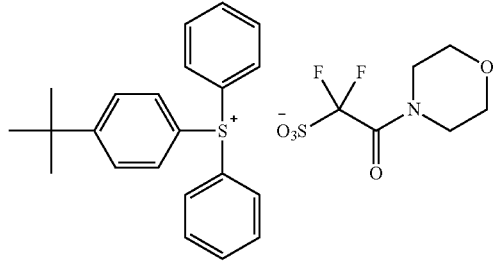

as an acid generator, and a photoresist composition comprising the salt.

SUMMARY OF THE INVENTION

The present invention is to provide a salt for suitable for an acid generator and a photoresist composition comprising the same.

The present invention relates to the followings:

<1> A salt represented by the formula (I):

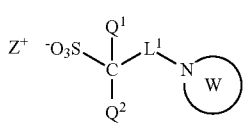

(I)

wherein $Q^1$ and $Q^2$ independently each represent a fluorine atom or a C1-C6 perfluoroalkyl group, $L^1$ represents a C1-C20 divalent saturated hydrocarbon group in which one or more —CH$_2$— can be replaced by —O— or —CO—, W represents a group represented by the formula (W1), (W2), (W3), (W4) or (W5):

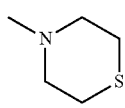

(W1)

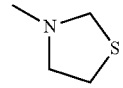

(W2)

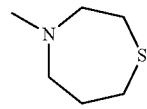

(W3)

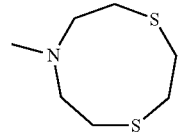

(W4)

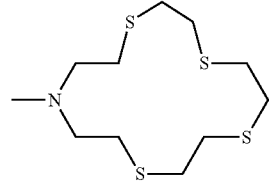

(W5)

and $Z^+$ represents an organic counter ion;

<2> The salt according to <1>, wherein W is the group represented by the formula (W1);

<3> The salt according to <1> or <2>, wherein $L^1$ is *—CO— or *—CO—O—(CH$_2$)$_n$— wherein * represents a binding position to —C($Q^1$)($Q^2$)- and n represents an integer of 1 to 18;

<4> The salt according to <1> or <2>, wherein $L^1$ is *—CO—O—(CH$_2$)$_n$— wherein * represents a binding position to —C($Q^1$)($Q^2$)- and n is 1, 2, 4, 6, 8, 10 or 12;

<5> An acid generator comprising the salt according to any one of <1> to <4>;

<6> A photoresist composition comprising the acid generator according to <5> and a resin having an acid-labile group, being insoluble or poorly soluble in an aqueous alkali solution but becoming soluble in an aqueous alkali solution by the action of an acid;

<7> The photoresist composition according to <6>, which further comprises a basic compound;

<8> The photoresist composition according to <6> or <7>, which further comprises a solvent;

<9> The photoresist composition according to <7>, which further comprises a solvent;

<10> A process for producing a photoresist pattern comprising the following steps (1) to (5):

(1) a step of applying the photoresist composition according to any one of <6> to <9> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

The salt of the present invention is represented by the formula (I):

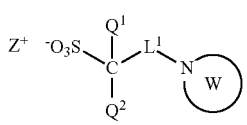

(I)

wherein $Q^1$ and $Q^2$ independently each represent a fluorine atom or a C1-C6 perfluoroalkyl group, $L^1$ represents a C1-C20 divalent saturated hydrocarbon group in which one or more —CH$_2$— can be replaced by —O— or —CO—, W represents a group represented by the formula (W1), (W2), (W3), (W4) or (W5):

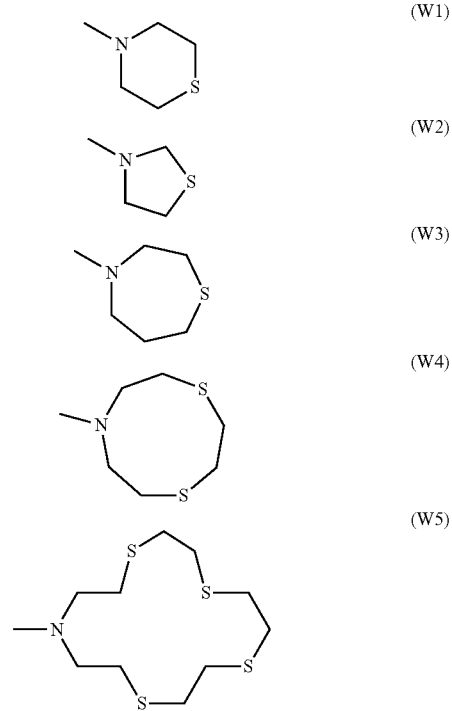

and $Z^+$ represents an organic counter ion (hereinafter, simply referred to as SALT (I)).

Examples of the C1-C6 perfluoroalkyl group include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group, and a trifluoromethyl group is preferable. It is preferred that $Q^1$ and $Q^2$ independently each represent a fluorine atom or a trifluoromethyl group, and it is more preferred that $Q^1$ and $Q^2$ are fluorine atoms.

Examples of the C1-C20 divalent saturated hydrocarbon group include a C1-C20 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an octadecane-1,18-diyl group, a nonadecane-1,19-diyl group and an icosane-1,20-diyl group; a C2-C20 branched alkanediyl group such as an ethane-1,1-diyl group, a propane-1,1-diyl group, a propane-2,2-diyl group, a butane-1,3-diyl group, a 2-methylpropane-1,3-diyl group, a 2-methylpropane-1,2-diyl group, a pentane-1,4-diyl group and a 2-methylbutane-1,4-diyl group; a divalent monocyclic saturated alicyclic hydrocarbon group such as a cycloalkanediyl group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated alicyclic hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group; and a group formed by combining two or more groups selected from the group consisting of the above-mentioned groups.

One or more —CH$_2$— in the C1-C20 divalent saturated hydrocarbon group can be replaced by —O— or —CO—, and examples of the C1-C20 divalent saturated hydrocarbon group in which one or more —CH$_2$— are replaced by —O— or —CO— include *—CO—, *—CO—O-$L^{b2}$-, *—CO—O-$L^{b4}$-CO—O-$L^{b3}$-, *-$L^{b5}$-O—CO-$L^{b6}$-, *-$L^{b8}$-O-$L^{b7}$-, *—CO—O-$L^{b9}$-O-$L^{b10}$-, *—CO—O-$L^{b13}$-O-$L^{b12}$-CO—O-$L^{b11}$- and *—CO—O-$L^{b14}$-CO— wherein $L^{b2}$ represents a C1-C18 divalent saturated hydrocarbon group, $L^{b3}$ represents a C1-C15 divalent saturated hydrocarbon group, $L^{b4}$ represents a C1-C15 divalent saturated hydrocarbon group, with the proviso that total carbon number of $L^{b3}$ and $L^{b4}$ is 1 to 16, $L^{b5}$ represents a C1-C17 divalent saturated hydrocarbon group, $L^{b6}$ represents a C1-C17 divalent saturated hydrocarbon group, with the proviso that total carbon number of $L^{b5}$ and $L^{b6}$ is 1 to 18, $L^{b7}$ represents a C1-C18 divalent saturated hydrocarbon group, $L^{b8}$ represents a C1-C18 divalent saturated hydrocarbon group, with the proviso that total carbon number of $L^{b7}$ and $L^{b8}$ is 1 to 19, $L^{b9}$ represents a C1-C16 divalent saturated hydrocarbon group, $L^{b10}$ represents a C1-C16 divalent saturated hydrocarbon group, with the proviso that total carbon number of $L^{b9}$ and $L^{b10}$ is 1 to 17, $L^{b11}$ represents a C1-C13 divalent saturated hydrocarbon group, $L^{b12}$ represents a C1-C13 divalent saturated hydrocarbon group, $L^{b13}$ represents a C1-C13 divalent saturated hydrocarbon group, with the proviso that total carbon number of $L^{b11}$, $L^{b12}$ and $L^{b13}$ is 1 to 15, $L^{b14}$ represents a C1-C17 divalent saturated hydrocarbon group, and * represents a binding position to —C($Q^1$)($Q^2$)-.

Among them, preferred are *—CO— and *—CO—O-$L^{b2}$-, and more preferred are *—CO— or *—CO—O—(CH$_2$)$_n$— wherein n represents an integer of 1 to 18, and especially preferred is *—CO—O—(CH$_2$)$_n$— wherein n is 1, 2, 4, 6, 8, 10 or 12.

Examples of *—CO—O-$L^{b2}$- include the following.

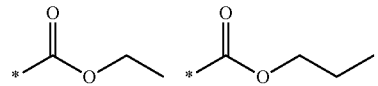

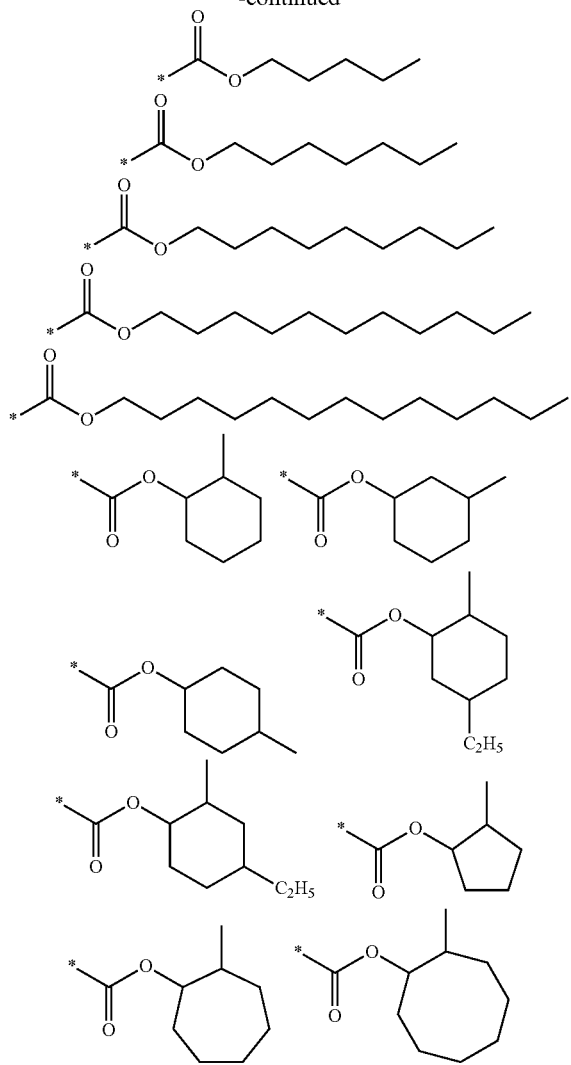
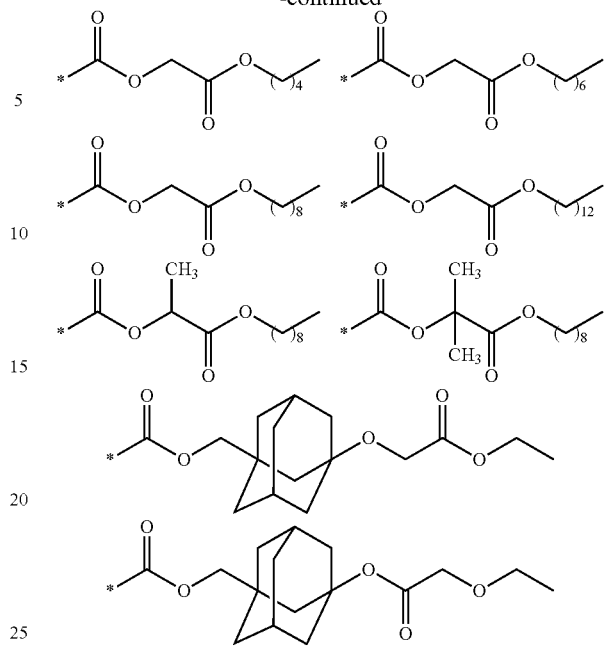
Examples of *—CO—O-$L^{b4}$-CO—O-$L^{b3}$- include the following.
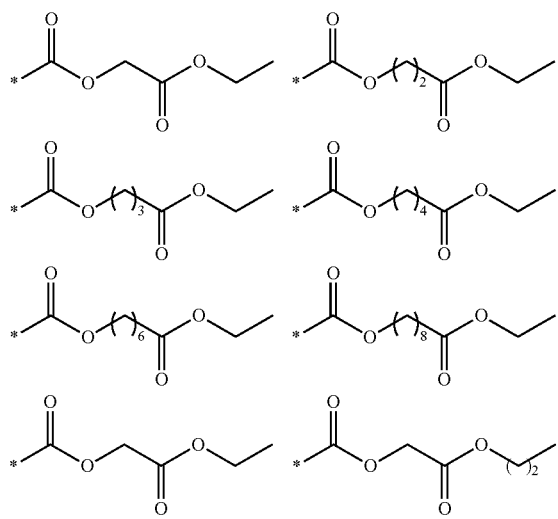
Examples of *-$L^{b5}$-O—CO-$L^{b6}$- include the following.
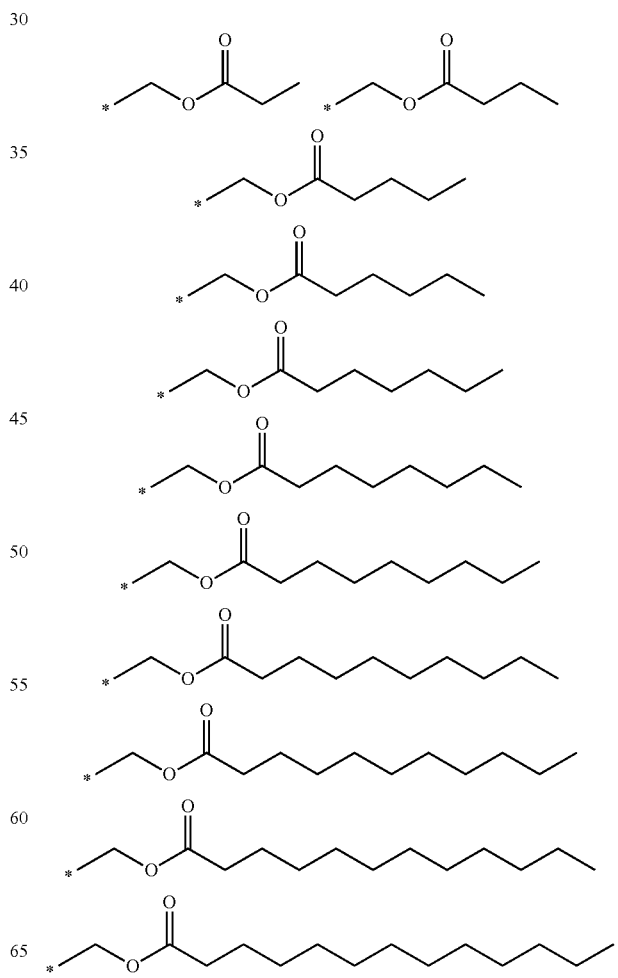

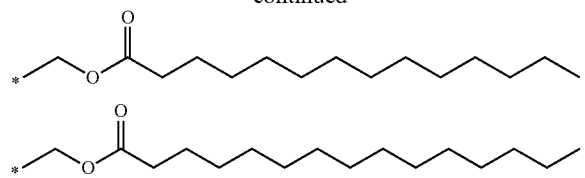
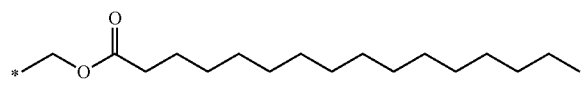
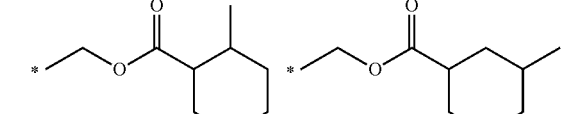
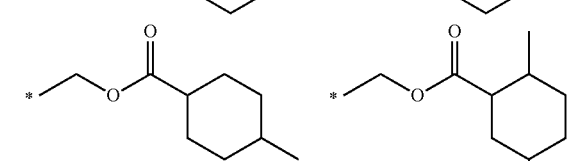
Examples of *-L$^{b8}$-O-L$^{b7}$- include the following.
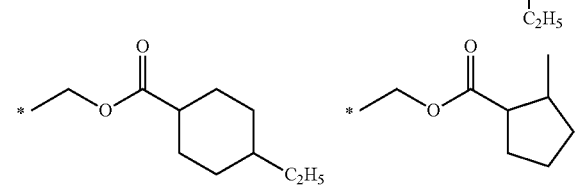
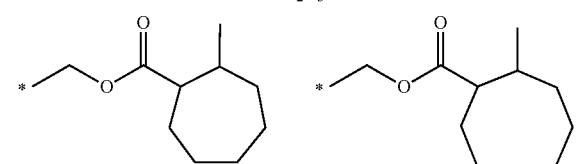
Examples of *—CO—O-L$^{b9}$-O-L$^{b10}$- include the following.
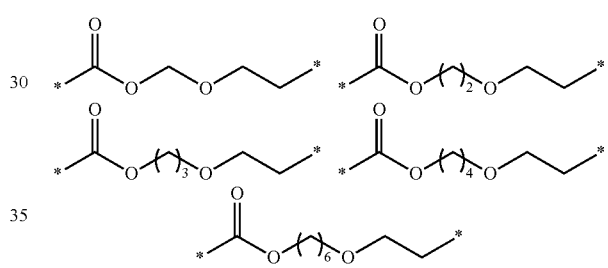
Examples of *—CO—O-L$^{b13}$-O-L$^{b12}$-CO—O-L$^{b11}$-include the following.
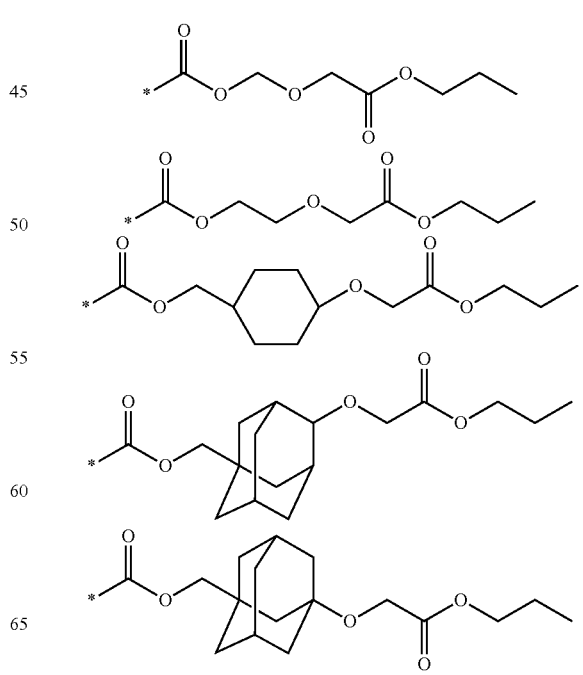

Examples of *—CO—O-L$^{b14}$-CO— include the following.
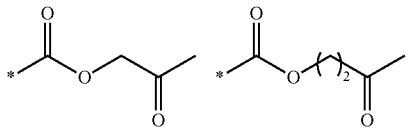
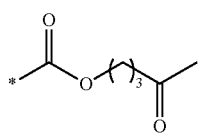
W represents a group represented by the formula (W1), (W2), (W3), (W4) or (W5):
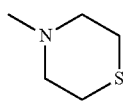
(W1)
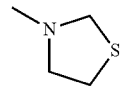
(W2)
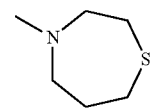
(W3)
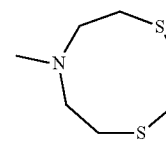
(W4)
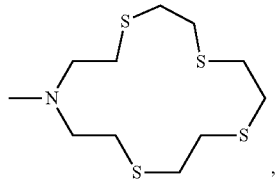
(W5)
and a group represented by the formula (W1), (W2) or (W3) is preferable, and a group represented by the formula (W1) is more preferable.
Examples of the anion part of SALT (I) include the anions represented by the formulae (I-a-1) to (I-a-28).
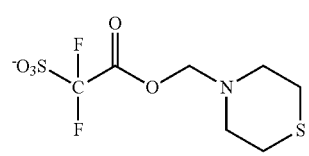
(I-a-1)
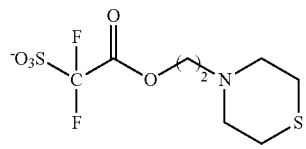
(I-a-2)
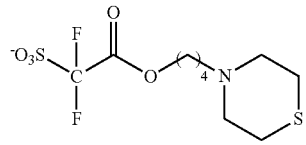
(I-a-3)
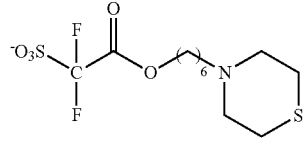
(I-a-4)
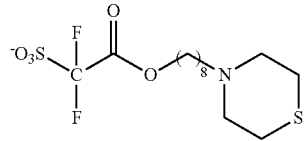
(I-a-5)
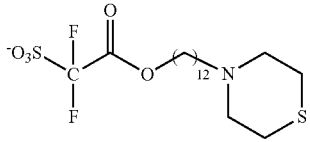
(I-a-6)
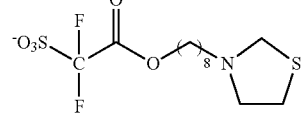
(I-a-7)
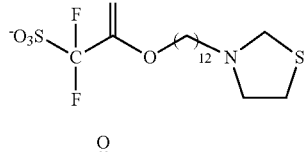
(I-a-8)
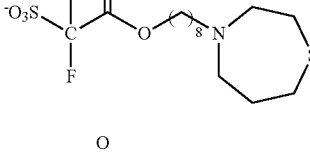
(I-a-9)
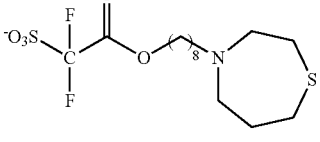
(I-a-10)
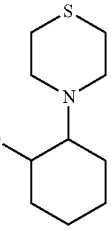
(I-a-11)

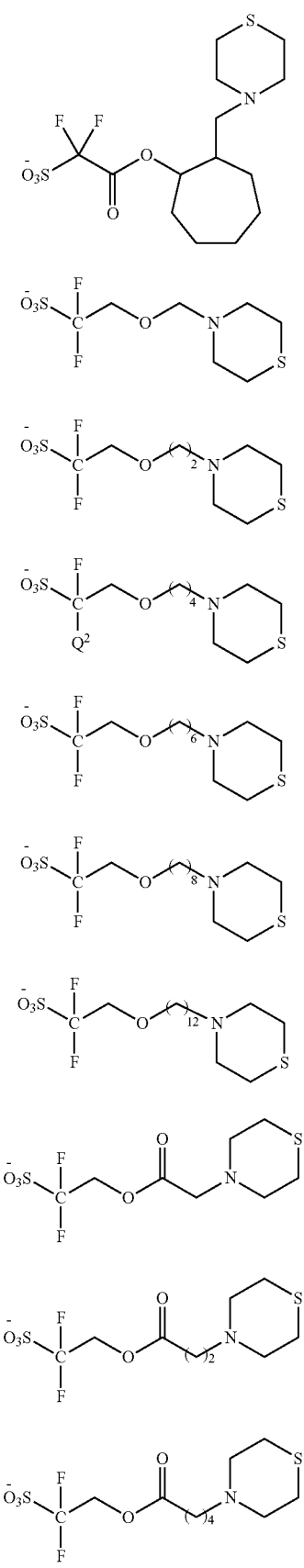

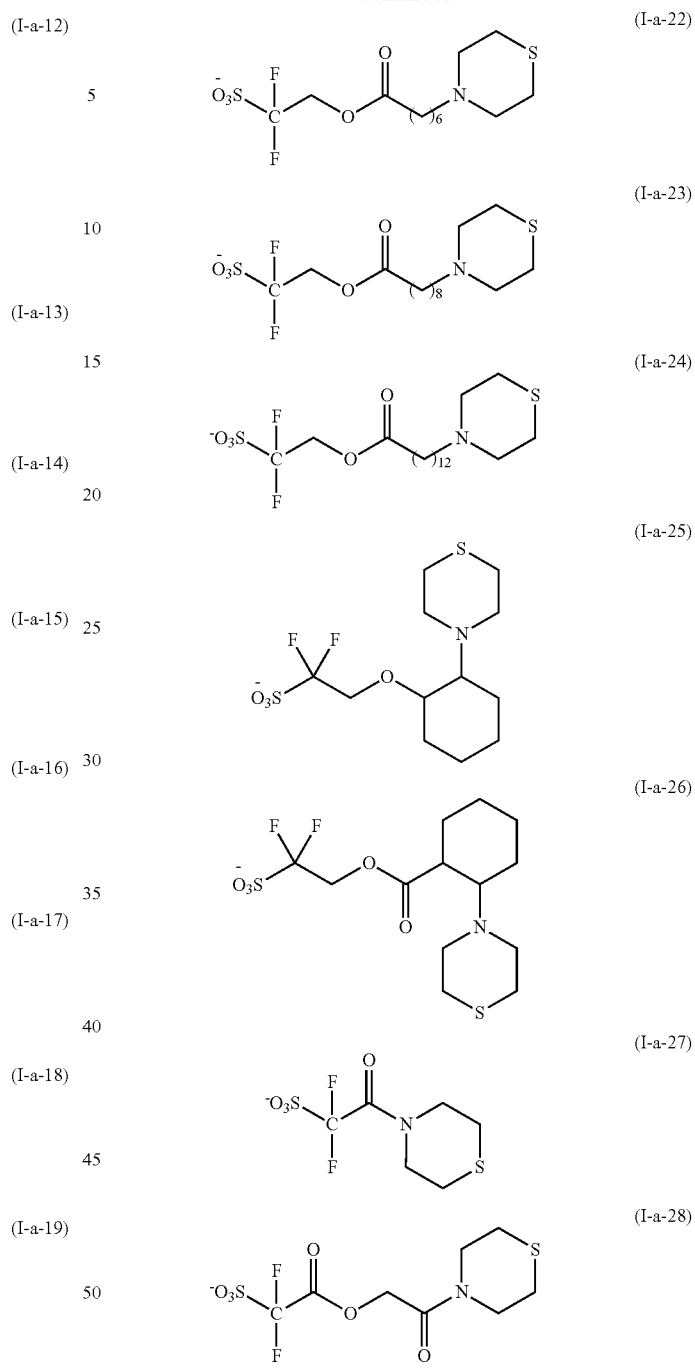

Examples of the organic counter ion represented by Z+ include an organic onium cation such as an organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable, and triarylsulfonium cation is especially preferable. "Arylsulfonium cation" means a sulfonium cation having at least one aryl group.

Preferable examples of the organic counter ion represented by Z+ include the cations represented by the formulae (b2-1) to (b2-4):

(b2-1)

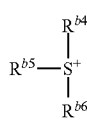

(b2-2)

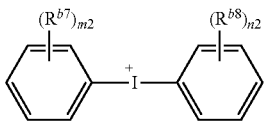

(b2-3)

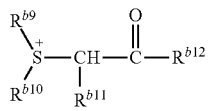

(b2-4)

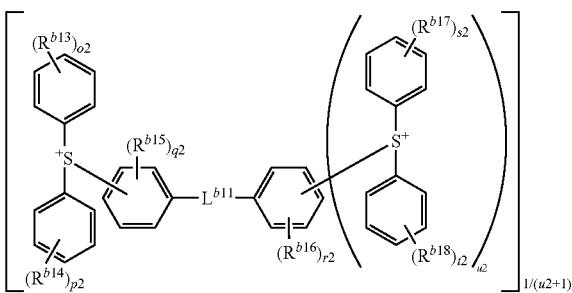

wherein $R^{b4}$, $R^{b5}$ and $R^{b6}$ independently represent a C1-C30 alkyl group which can have one or more substituents selected from the group consisting of a hydroxyl group, a C1-C12 alkoxy group and a C6-C18 aromatic hydrocarbon group, a C3-C18 alicyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 alkyl group, a C3-C18 alicyclic hydrocarbon group and a C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxyl group, a C1-C12 alkyl group or a C1-C12 alkoxy group, m2 and n2 independently represents an integer of 0 to 5, $R^{b9}$ and $R^{b10}$ independently represent a C1-C18 alkyl group or a C3-C18 alicyclic hydrocarbon group, or $R^{b9}$ and $R^{b10}$ are bonded to form a C2-C11 divalent acyclic hydrocarbon group which forms a ring together with the adjacent $S^+$, and one or more —CH$_2$— in the divalent acyclic hydrocarbon group may be replaced by —CO—, —O— or —S—, and $R^{11}$ represents a hydrogen atom, a C1-C18 alkyl group, a C3-C18 alicyclic hydrocarbon group or a C6-C18 aromatic hydrocarbon group, $R^{12}$ represents a C1-C12 alkyl group, a C3-C18 alicyclic hydrocarbon group or a C6-C18 aromatic hydrocarbon group and the aromatic hydrocarbon group can have one or more substituents selected from the group consisting of a C1-C12 alkyl group, a C1-C12 alkoxy group, a C3-C18 alicyclic hydrocarbon group and a C2-C13 acyloxy group, or $R^{b11}$ and $R^{b12}$ are bonded each other to form a C1-C10 divalent acyclic hydrocarbon group which forms a 2-oxo-cycloalkyl group together with the adjacent —CHCO—, and one or more —CH$_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The alkyl group represented by $R^{b4}$, $R^{b5}$ and $R^{b6}$ has preferably 1 to 12 carbon atoms. The alicyclic hydrocarbon group represented by $R^{b4}$, $R^{b5}$ and $R^{b6}$ has preferably 4 to 12 carbon atoms.

The alkyl group represented by $R^{b9}$ to $R^{b11}$ has preferably 1 to 12 carbon atoms. The alicyclic hydrocarbon group represented by $R^{b9}$ to $R^{b11}$ has preferably 4 to 12 carbon atoms.

The alicyclic hydrocarbon group represented by $R^{b12}$ has preferably 4 to 12 carbon atoms.

Preferable examples of the alkyl group include a methyl group, an ethyl group, a propyl group, an isopropyl group, a butyl group, a sec-butyl group, a tert-butyl group, a pentyl group, a hexyl group, an octyl group, a 2-ethylhexyl group, a decyl group, a dodecyl group, a hexadecyl group, a pentadecyl group, a heptadecyl group and an octadecyl group, and more preferable examples thereof include a methyl group, an ethyl group, a propyl group, an isopropyl group, a butyl group, a sec-butyl group, a tert-butyl group, a pentyl group, a hexyl group, an octyl group and a 2-ethylhexyl group. The alicyclic hydrocarbon group may be monocyclic or polycyclic. Preferable examples of the monocyclic alicyclic hydrocarbon group include a cycloalkyl group such as a cyclopropyl group, a cyclobutyl group, a cyclopentyl group, a cyclohexyl group, a cycloheptyl group and a cyclodecyl group. Preferable examples of the polycyclic alicyclic hydrocarbon group include a decahydronaphthyl group, an adamantyl group, a 2-alkyladamantan-2-yl group, a 1-(adamantan-1-yl)alkan-1-yl group, an isobornyl group, a methylnorbornyl group and the following groups.

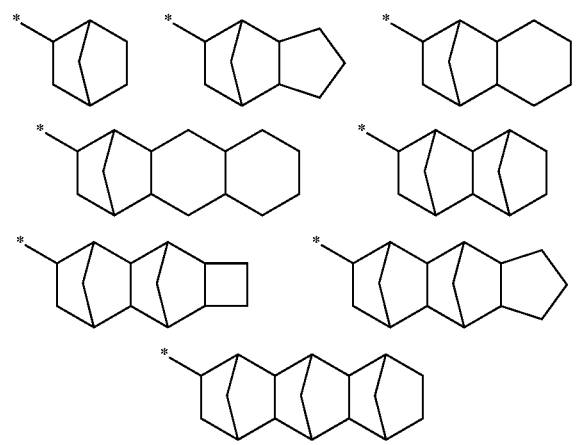

More preferable examples of the alicyclic hydrocarbon group include a cyclopropyl group, a cyclobutyl group, a cyclopentyl group, a cyclohexyl group, a cycloheptyl group, a cyclodecyl group, a 2-alkyladamantan-2-yl group, a 1-(adamantan-1-yl) alkan-1-yl group, and an isobornyl group.

Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group, a naphthyl group, an anthryl group, a p-adamantylphenyl group, a tolyl group, a mesityl group, a phenathryl group, a 2,6-diethylphenyl group and a 2-methyl-6-ethylphenyl group.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propionyl group, a butyryl group, isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms.

Examples of the aliphatic hydrocarbon group having an aromatic hydrocarbon group include a benzyl group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent and the divalent acyclic hydrocarbon group include a thiolan-1-ium ring (tetrahydrothiphenium ring), a thian-1-ium ring and a 1,4-oxathian-4-ium ring. AC3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

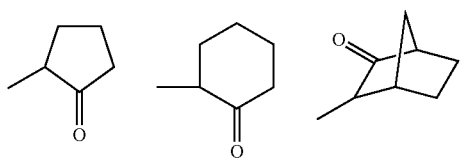

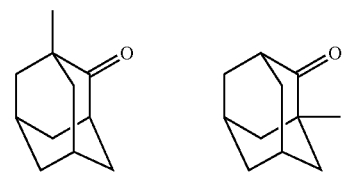

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation is especially preferable.

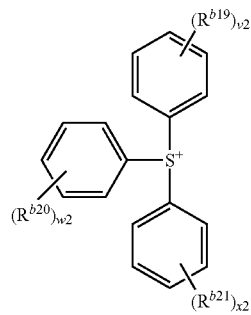

(b2-1-1)

wherein $R^{b19}$, $R^{b20}$ and $R^{b21}$ are independently in each occurrence a halogen atom (preferably a fluorine atom), a hydroxyl group, a C1-C18 alkyl group, a C3-C18 alicyclic hydrocarbon group or a C1-C12 alkoxy group, and one or more hydrogen atoms of the alkyl group can be replaced by a hydroxyl group, a C1-C12 alkoxy group or a C6-C18 aromatic hydrocarbon group, and one or more hydrogen atoms of the alicyclic hydrocarbon group can be replaced by a halogen atom, a glycidyloxy group or a C2-C4 acyl group, and v2, w2 and x2 independently each represent an integer of 0 to 5.

The alkyl group has preferably 1 to 12 carbon atoms, and the alicyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the organic counter ion include those described in JP 2010-204646 A.

Preferable examples of the organic counter ion include the following.

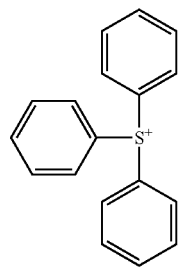

(b2-c-1)

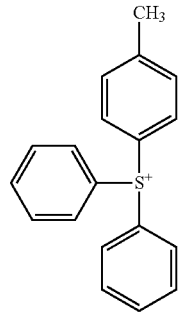

(b2-c-2)

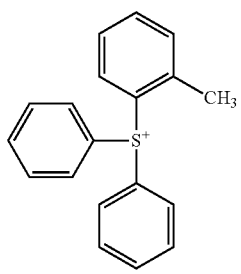 (b2-c-3)
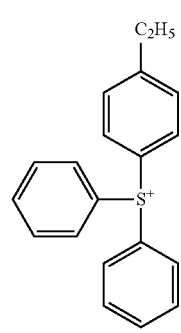 (b2-c-4)
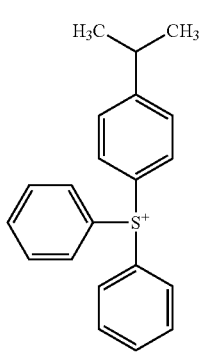 (b2-c-5)
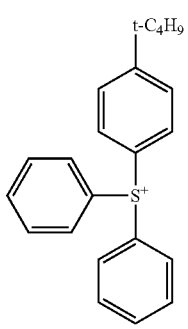 (b2-c-6)
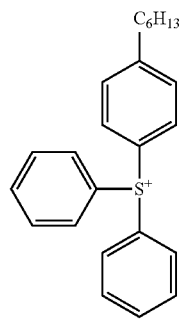 (b2-c-7)
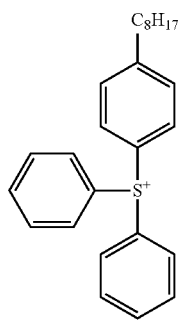 (b2-c-8)
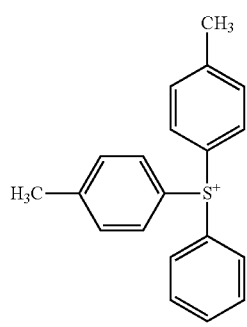 (b2-c-9)
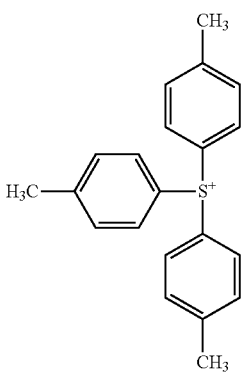 (b2-c-10)
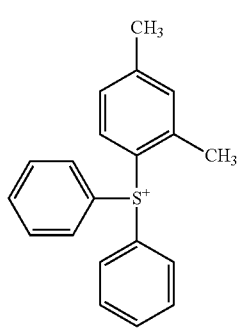 (b2-c-11)
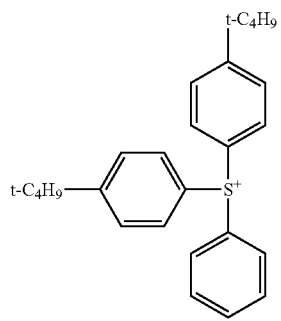 (b2-c-12)

(b2-c-13)
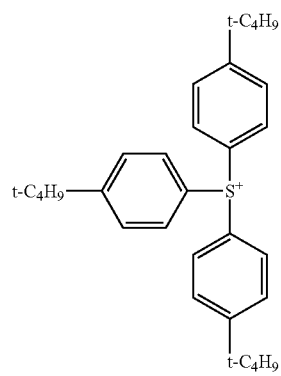
(b2-c-14)
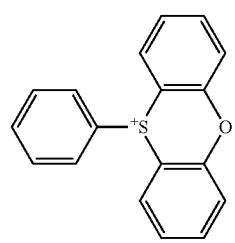
(b2-c-15)
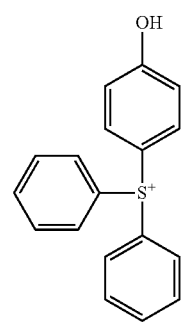
(b2-c-16)
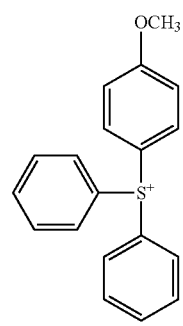
(b2-c-17)
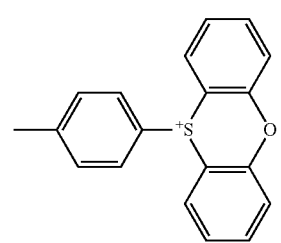
(b2-c-18)
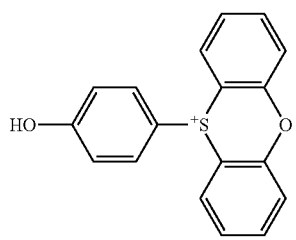
(b2-c-19)
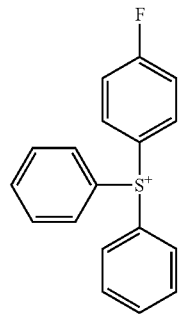
(b2-c-20)
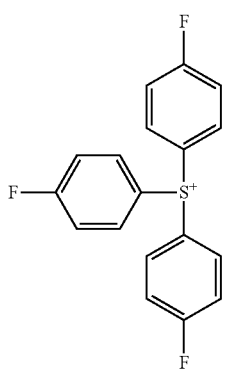
(b2-c-21)
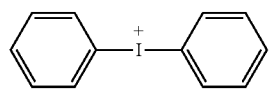
(b2-c-22)
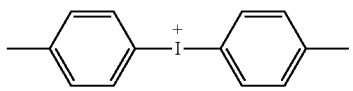
(b2-c-23)
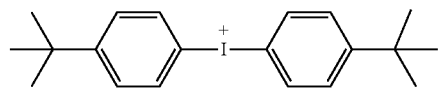
(b2-c-24)
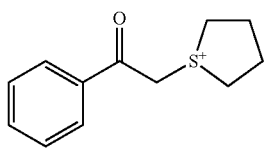
(b2-c-25)
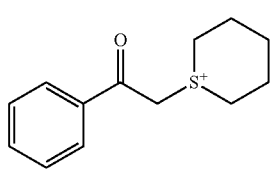

-continued

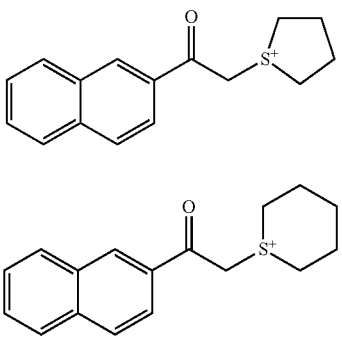

(b2-c-26)

(b2-c-27)

Examples of SALT (I) include a salt wherein the anion is any one of the above-mentioned anions and the cation is any one of organic counter ions. Preferable examples of SALT (I) include the following salts described in Tables 1 to 5.

TABLE 1

| SALT (I) | Anion | Organic Counter Ion |
|---|---|---|
| (I-1) | (I-a-5) | (b2-c-1) |
| (I-2) | (I-a-6) | (b2-c-1) |
| (I-3) | (I-a-7) | (b2-c-1) |
| (I-4) | (I-a-8) | (b2-c-1) |
| (I-5) | (I-a-9) | (b2-c-1) |
| (I-6) | (I-a-10) | (b2-c-1) |
| (I-7) | (I-a-11) | (b2-c-1) |
| (I-8) | (I-a-12) | (b2-c-1) |
| (I-9) | (I-a-5) | (b2-c-10) |
| (I-10) | (I-a-6) | (b2-c-10) |

TABLE 2

| SALT (I) | Anion | Organic Counter Ion |
|---|---|---|
| (I-11) | (I-a-7) | (b2-c-10) |
| (I-12) | (I-a-8) | (b2-c-10) |
| (I-13) | (I-a-9) | (b2-c-10) |
| (I-14) | (I-a-10) | (b2-c-10) |
| (I-15) | (I-a-11) | (b2-c-10) |
| (I-16) | (I-a-12) | (b2-c-10) |
| (I-17) | (I-a-5) | (b2-c-21) |
| (I-18) | (I-a-6) | (b2-c-21) |
| (I-19) | (I-a-7) | (b2-c-21) |
| (I-20) | (I-a-8) | (b2-c-21) |
| (I-21) | (I-a-9) | (b2-c-21) |
| (I-22) | (I-a-10) | (b2-c-21) |
| (I-23) | (I-a-11) | (b2-c-21) |
| (I-24) | (I-a-12) | (b2-c-21) |
| (I-25) | (I-a-5) | (b2-c-24) |
| (I-26) | (I-a-6) | (b2-c-24) |
| (I-27) | (I-a-7) | (b2-c-24) |
| (I-28) | (I-a-8) | (b2-c-24) |
| (I-29) | (I-a-9) | (b2-c-24) |
| (I-30) | (I-a-10) | (b2-c-24) |
| (I-31) | (I-a-11) | (b2-c-24) |
| (I-32) | (I-a-12) | (b2-c-24) |
| (I-33) | (I-a-5) | (b2-c-2) |
| (I-34) | (I-a-6) | (b2-c-2) |
| (I-35) | (I-a-7) | (b2-c-2) |
| (I-36) | (I-a-5) | (b2-c-21) |
| (I-37) | (I-a-6) | (b2-c-21) |
| (I-38) | (I-a-7) | (b2-c-21) |
| (I-39) | (I-a-5) | (b2-c-23) |
| (I-40) | (I-a-6) | (b2-c-23) |

TABLE 3

| SALT (I) | Anion | Organic Counter Ion |
|---|---|---|
| (I-41) | (I-a-7) | (b2-c-23) |
| (I-42) | (I-a-5) | (b2-c-26) |
| (I-43) | (I-a-6) | (b2-c-26) |
| (I-44) | (I-a-7) | (b2-c-26) |
| (I-45) | (I-a-5) | (b2-c-6) |
| (I-46) | (I-a-6) | (b2-c-6) |
| (I-47) | (I-a-7) | (b2-c-6) |
| (I-48) | (I-a-5) | (b2-c-15) |
| (I-49) | (I-a-6) | (b2-c-15) |
| (I-50) | (I-a-7) | (b2-c-15) |
| (I-51) | (I-a-1) | (b2-c-1) |
| (I-52) | (I-a-1) | (b2-c-10) |
| (I-53) | (I-a-1) | (b2-c-14) |
| (I-54) | (I-a-2) | (b2-c-1) |
| (I-55) | (I-a-2) | (b2-c-10) |
| (I-56) | (I-a-2) | (b2-c-14) |
| (I-57) | (I-a-3) | (b2-c-1) |
| (I-58) | (I-a-3) | (b2-c-10) |
| (I-59) | (I-a-3) | (b2-c-14) |
| (I-60) | (I-a-4) | (b2-c-1) |
| (I-61) | (I-a-4) | (b2-c-10) |
| (I-62) | (I-a-4) | (b2-c-14) |
| (I-63) | (I-a-13) | (b2-c-1) |
| (I-64) | (I-a-13) | (b2-c-10) |
| (I-65) | (I-a-13) | (b2-c-14) |
| (I-66) | (I-a-14) | (b2-c-1) |
| (I-67) | (I-a-14) | (b2-c-10) |
| (I-68) | (I-a-14) | (b2-c-14) |
| (I-69) | (I-a-15) | (b2-c-1) |
| (I-70) | (I-a-15) | (b2-c-10) |

TABLE 4

| SALT (I) | Anion | Organic Counter Ion |
|---|---|---|
| (I-71) | (I-a-15) | (b2-c-14) |
| (I-72) | (I-a-16) | (b2-c-1) |
| (I-73) | (I-a-16) | (b2-c-10) |
| (I-74) | (I-a-16) | (b2-c-14) |
| (I-75) | (I-a-17) | (b2-c-1) |
| (I-76) | (I-a-17) | (b2-c-10) |
| (I-77) | (I-a-17) | (b2-c-14) |
| (I-78) | (I-a-18) | (b2-c-1) |
| (I-79) | (I-a-18) | (b2-c-10) |
| (I-80) | (I-a-18) | (b2-c-14) |
| (I-81) | (I-a-19) | (b2-c-1) |
| (I-82) | (I-a-19) | (b2-c-10) |
| (I-83) | (I-a-19) | (b2-c-14) |
| (I-84) | (I-a-20) | (b2-c-1) |
| (I-85) | (I-a-20) | (b2-c-10) |
| (I-86) | (I-a-20) | (b2-c-14) |
| (I-87) | (I-a-21) | (b2-c-1) |
| (I-88) | (I-a-21) | (b2-c-10) |
| (I-89) | (I-a-21) | (b2-c-14) |
| (I-90) | (I-a-22) | (b2-c-1) |
| (I-91) | (I-a-22) | (b2-c-10) |
| (I-92) | (I-a-22) | (b2-c-14) |
| (I-93) | (I-a-23) | (b2-c-1) |
| (I-94) | (I-a-23) | (b2-c-10) |
| (I-95) | (I-a-23) | (b2-c-14) |
| (I-96) | (I-a-24) | (b2-c-1) |
| (I-97) | (I-a-24) | (b2-c-10) |
| (I-98) | (I-a-24) | (b2-c-14) |
| (I-99) | (I-a-25) | (b2-c-1) |
| (I-100) | (I-a-25) | (b2-c-10) |

TABLE 5

| SALT (I) | Anion | Organic Counter Ion |
|---|---|---|
| (I-101) | (I-a-25) | (b2-c-14) |
| (I-102) | (I-a-26) | (b2-c-1) |
| (I-103) | (I-a-26) | (b2-c-10) |

TABLE 5-continued
| SALT (I) | Anion | Organic Counter Ion |
|----------|----------|---------------------|
| (I-104)  | (I-a-26) | (b2-c-14)           |
| (I-105)  | (I-a-27) | (b2-c-1)            |
| (I-106)  | (I-a-28) | (b2-c-1)            |
| (I-107)  | (I-a-27) | (b2-c-10)           |
| (I-108)  | (I-a-28) | (b2-c-10)           |
| (I-109)  | (I-a-27) | (b2-c-21)           |
| (I-110)  | (I-a-28) | (b2-c-21)           |
| (I-111)  | (I-a-27) | (b2-c-24)           |
| (I-112)  | (I-a-28) | (b2-c-24)           |
Among them, preferred are the following.
(I-1)
(I-2)
(I-3)
(I-4)
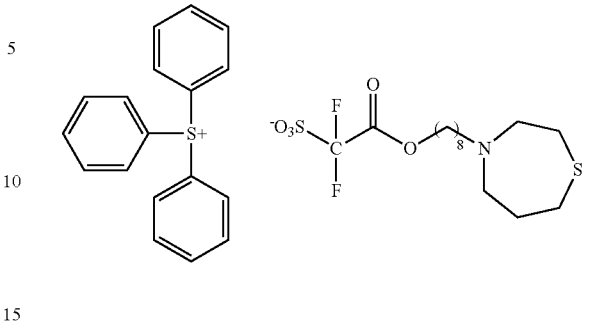
(I-5)
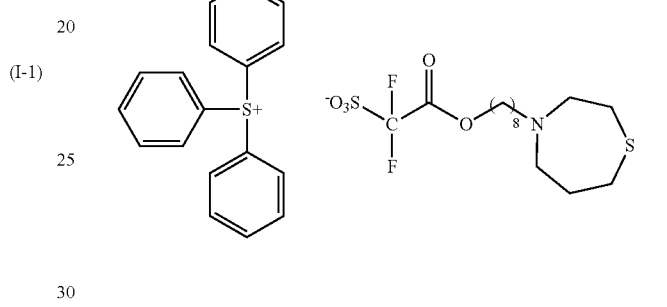
(I-6)
(I-7)
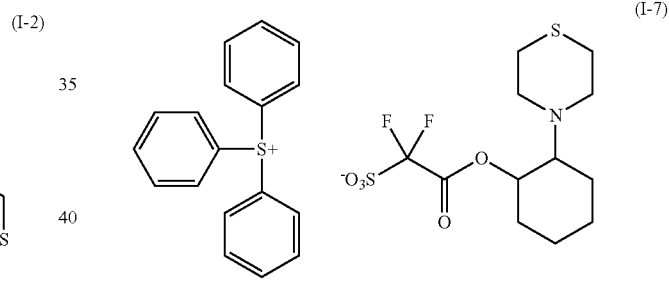
(I-8)
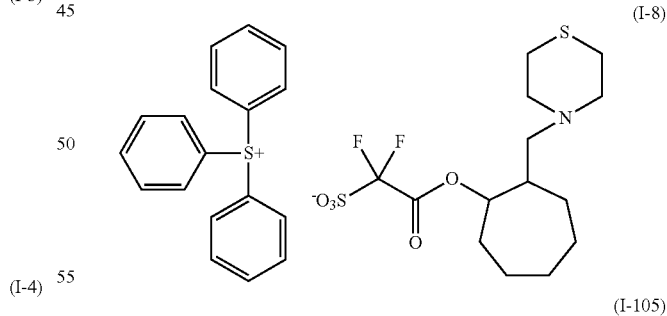
(I-105)
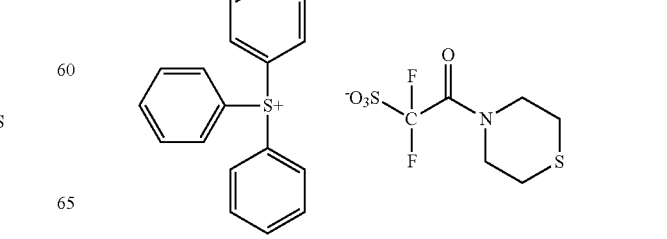

(I-106)
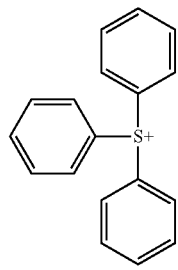 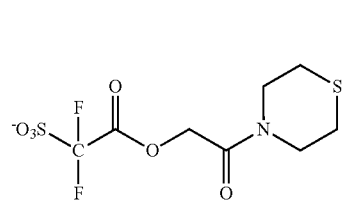
(I-9)
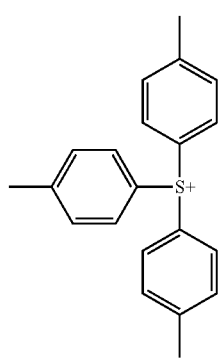 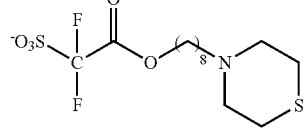
(I-10)
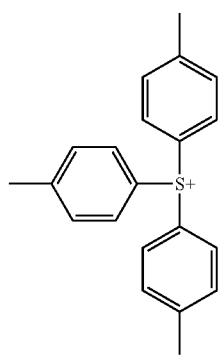 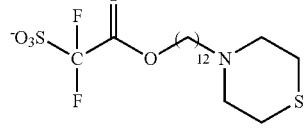
(I-11)
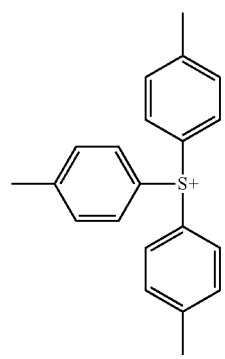 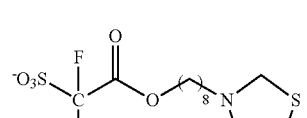
(I-12)
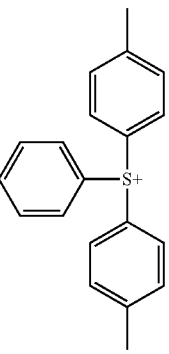 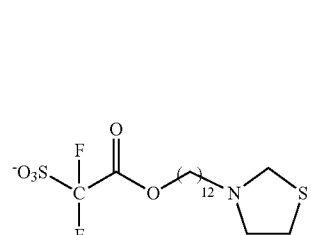
(I-13)
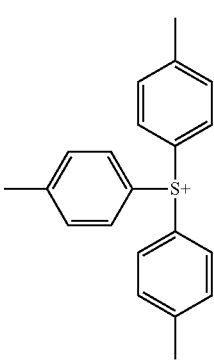 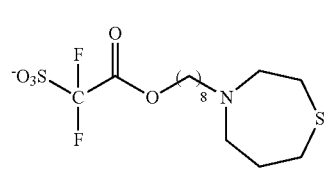
(I-14)
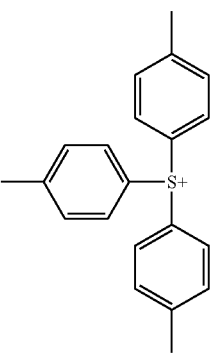 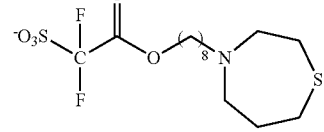
(I-15)
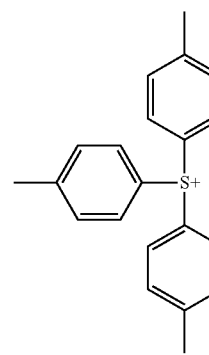 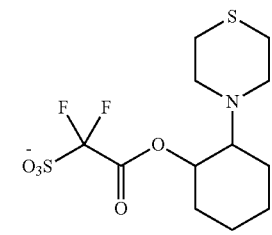

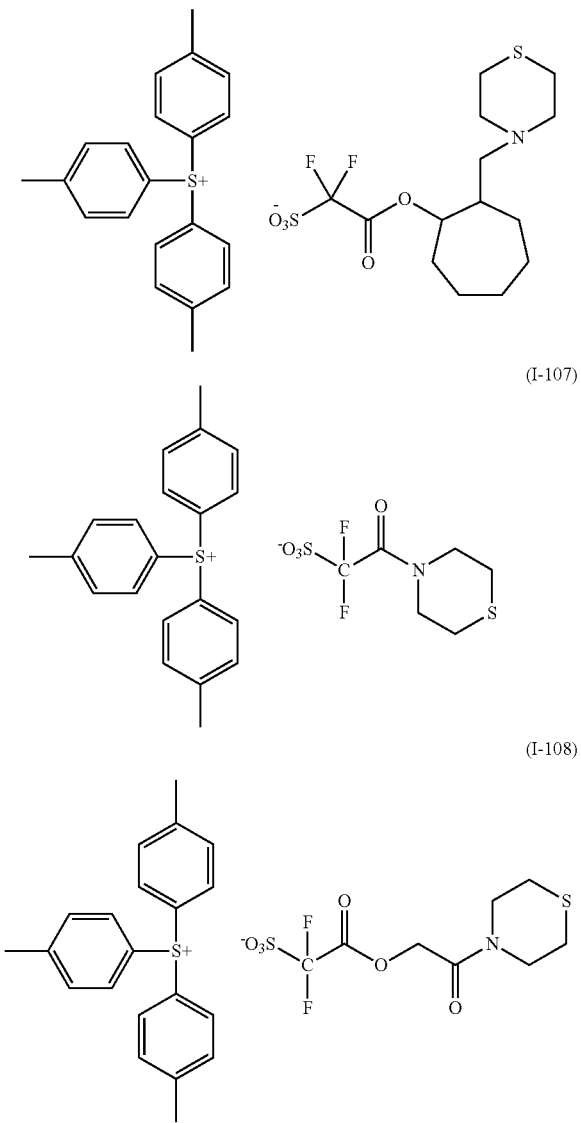
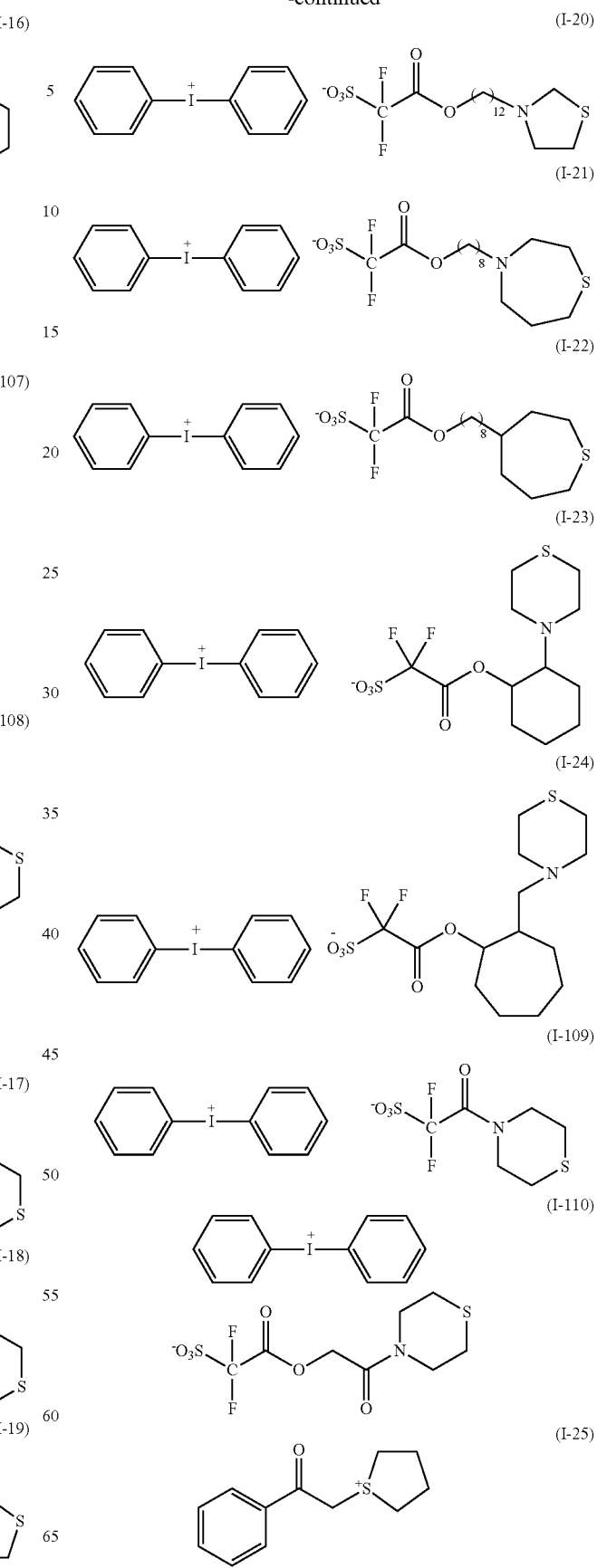

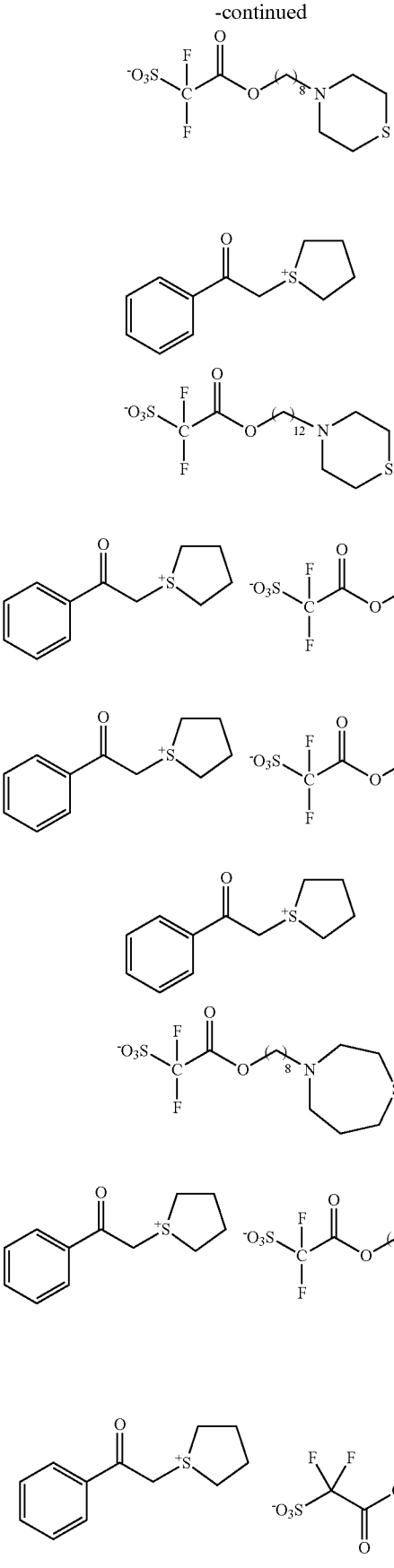
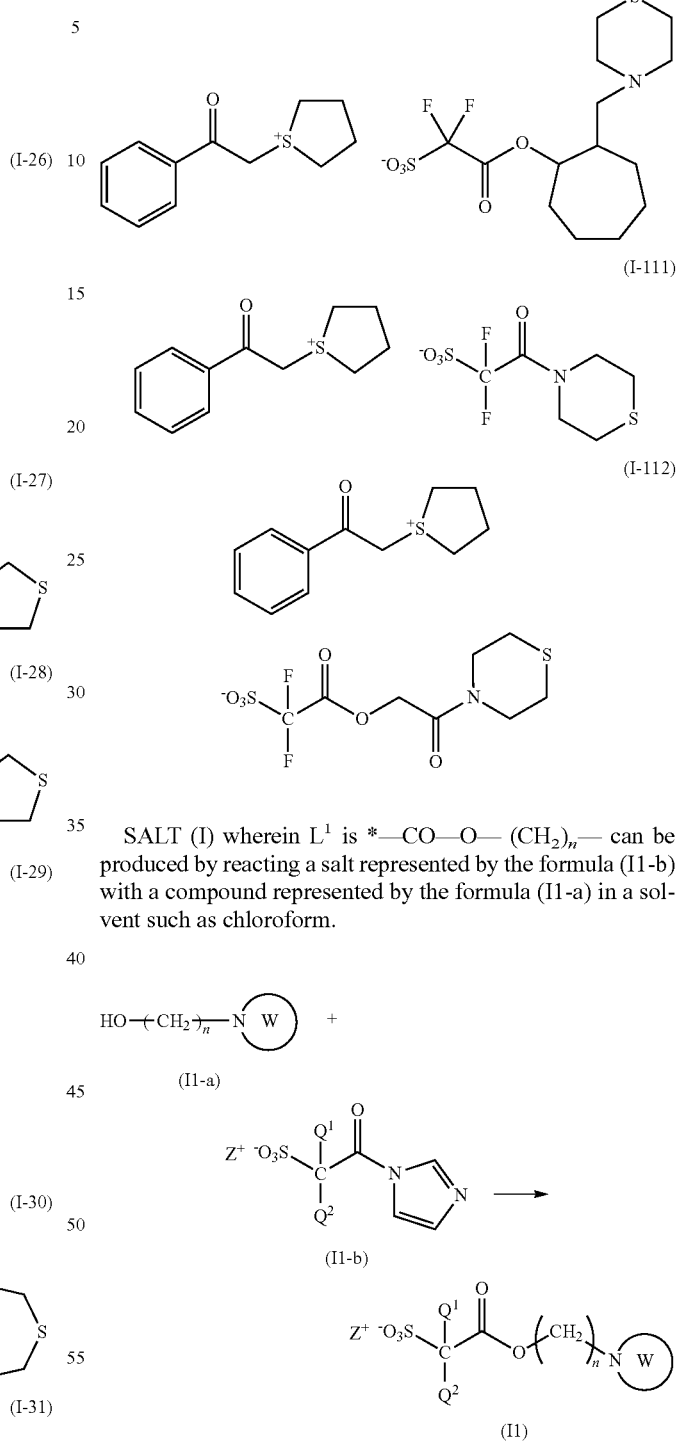

SALT (I) wherein $L^1$ is *—CO—O—$(CH_2)_n$— can be produced by reacting a salt represented by the formula (I1-b) with a compound represented by the formula (I1-a) in a solvent such as chloroform.

wherein $Q^1$, $Q^2$, W, n and $Z^+$ are the same as defined above.

The compound represented by the formula (I1-a) can be produced by reacting a compound represented by the formula (I1-c) with a compound represented by the formula (I1-d) in the presence of a base such as N-methylpyrrolidine in a solvent such as methyl isobutyl ketone.

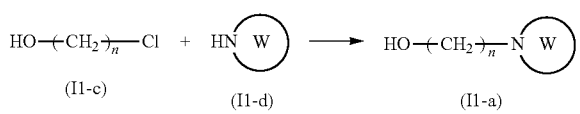

wherein W and n are the same as defined above.

Examples of the compound represented by the formula (I1-c) include 8-chloro-1-octanol. Examples of the compound represented by the formula (I1-d) include thiomorpholine.

The salt represented by the formula (I1-b) can be produced by reacting a salt represented by the formula (I1-e) with a compound represented by the formula (I1-f) in a solvent such as chloroform.

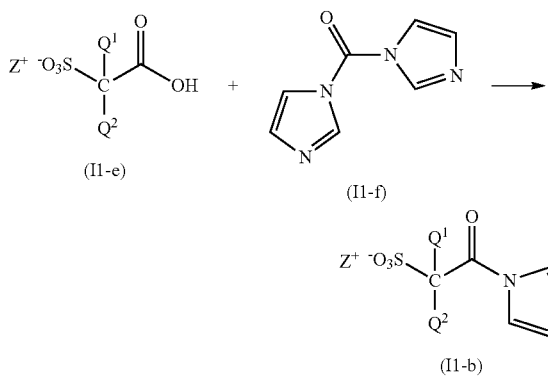

wherein $Q^1$, $Q^2$ and $Z^+$ are the same as defined above.

The salt represented by the formula (I1-e) can be produced according to the method described in JP 2008-127367 A.

SALT (I) wherein $L^1$ is *—CO— can be produced by reacting the above-mentioned salt represented by the formula (I1-b) with the above-mentioned compound represented by the formula (I1-d) in a solvent such as chloroform.

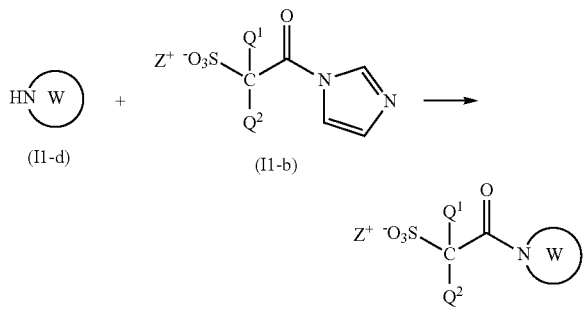

wherein $Q^1$, $Q^2$ W and $Z^+$ are the same as defined above.

Next, the acid generator of the present invention will be illustrated.

The acid generator of the present invention comprises SALT (I). The acid generator of the present invention can contain two or more kinds of SALT (I). The acid generator of the present invention can contain one or more known acid generators other than SALT (I) in addition to SALT (I).

Examples of the known acid generator include a nonionic acid generator, an ionic acid generator and the combination thereof. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and diazonaphthoquinone 4-sulfonate. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonulmethide anion. The onium salt compound is preferable.

Other examples of the known acid generator include acid generators described in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712.

Among them, preferred is a fluorine-containing acid generator.

Preferable examples of the known acid generator include a salt represented by the formula (II):

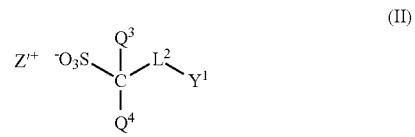

(II)

wherein $Q^3$ and $Q^4$ each independently represent a fluorine atom or a C1-C6 perfluoroalkyl group, $L^2$ represents a C1-C17 saturated divalent hydrocarbon group which can have one or more substituents and in which one or more —$CH_2$— can be replaced by —O— or —CO—, $Y^1$ represents a C1-C36 aliphatic hydrocarbon group or a C3-C36 alicyclic hydrocarbon group, and the aliphatic hydrocarbon group and the alicyclic hydrocarbon group can have one or more substituents, and one or more —$CH_2$— in the aliphatic hydrocarbon group and the alicyclic hydrocarbon group can be replaced by —O—, —CO— or —$SO_2$—, and $Z'^+$ represents an organic counter ion.

Examples of the C1-C6 perfluoroalkyl group represented by $Q^3$ and $Q^4$ include the same as those of $Q^1$ and $Q^2$.

Examples of the C1-C17 saturated divalent hydrocarbon group represented by $L^2$ include the same as those of $L^1$. The saturated divalent hydrocarbon group is preferably a linear or branched chain alkanediyl group.

Examples of the C1-C17 saturated divalent hydrocarbon group in which one or more —$CH_2$— are replaced by —O— or —CO— include *—CO—O-$L^d$-, *—CO—O-$L^f$-CO—O-$L^e$-, *-$L^g$-O—CO—, *-$L^i$-O-$L^h$-, *—CO—O-$L^j$-O—, and *—CO—O-$L^m$-O-$L^k$-CO—O—, wherein $L^d$ represents a single bond or a C1-C15 divalent saturated hydrocarbon group, $L^e$ represents a single bond or a C1-C12 divalent saturated hydrocarbon group, $L^f$ represents a single bond or a C1-C13 divalent saturated hydrocarbon group, with proviso that total carbon number of $L^e$ and $L^f$ is 1 to 13, $L^g$ represents a C1-C15 divalent saturated hydrocarbon group, $L^h$ represents a C1-C15 divalent saturated hydrocarbon group, $L^i$ represents a C1-C15 divalent saturated hydrocarbon group, with proviso that total carbon number of $L^h$ and $L^i$ is 1 to 16, $L^j$ represents a C1-C14 divalent saturated hydrocarbon group, $L^k$ represents a C1-C11 divalent saturated hydrocarbon group, $L^m$ represents a C1-C11 divalent saturated hydrocarbon group, with proviso that total carbon number of $L^k$ and $L^{bm}$ is 1 to 12, and * represents a binding position to —C $(Q^3)(Q^4)$-. Among them, preferred is *—CO—O-$L^d$-, and more preferred is *—CO—O-$L^d$- in which $L^d$ is a single bond or —CH$_2$—.

Examples of *—CO—O-$L^d$- include *—CO—O— and *—CO—O—CH$_2$. Examples of *—CO—O-$L^f$-CO—O-$L^e$- include *—CO—O—CH$_2$—CO—O—, *—CO—O—(CH$_2$)$_2$—CO—O—, *—CO—O—(CH$_2$)$_3$—CO—O—, *—CO—O—(CH$_2$)$_4$—CO—O—, *—CO—O—(CH$_2$)$_6$—CO—O—, *—CO—O—(CH$_2$)$_8$—CO—O—, *—CO—O—CH$_2$—CH(CH$_3$)—CO—O— and *—CO—O—CH$_2$—C(CH$_3$)$_2$—CO—O—. Examples of *-$L^g$-O—CO— include *—CH$_2$—O—CO—, *—(CH$_2$)$_2$—O—CO—, *—(CH$_2$)$_3$—O—CO—, *—(CH$_2$)$_4$—O—CO—, *—(CH$_2$)$_6$—O—CO— and *—(CH$_2$)$_8$—O—CO—. Examples of *-$L^i$-O-$L^h$- include *—CH$_2$—O—CH$_2$—. Examples of *—CO—O-$L^j$-O— include *—CO—O—CH$_2$—O—, *—CO—O—(CH$_2$)$_2$—O—, *—CO—O—(CH$_2$)$_3$—O—, *—CO—O—(CH$_2$)$_4$—O— and *—CO—O—(CH$_2$)$_6$—O—. Examples of *—CO—O-$L^m$-O-$^{9k}$-CO—O— include the followings.

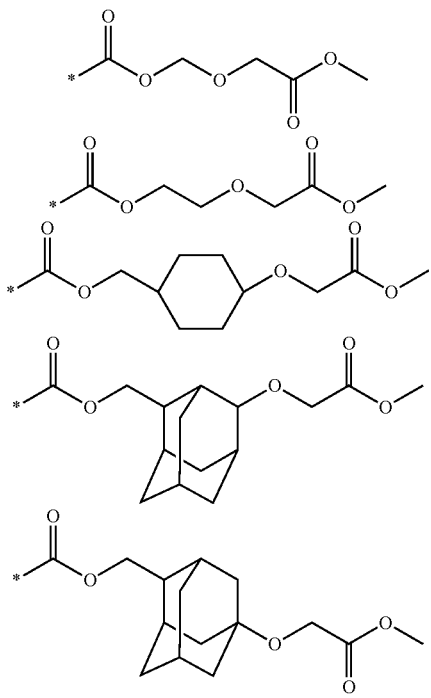

The C1-C17 saturated divalent hydrocarbon group can have one or more substituents, and examples of the substituent include a halogen atom, a hydroxyl group, a carboxyl group, a C6-C18 aromatic hydrocarbon group, a C7-C21 aralkyl group, a C2-C4 acyl group and a glycidyloxy group.

Examples of the substituent in $Y^1$ include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —(CH$_2$)$_{j2}$—O—CO—$R^{b1}$— in which $R^{b1}$ represents a C1-C16 alkyl group, a C3-C16 alicyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the alkyl group include the same as described above. Examples of the hydroxyl-containing aliphatic hydrocarbon group include a hydroxymethyl group. Examples of the C3-C16 alicyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 alkyl group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C18 alicyclic hydrocarbon group represented by $Y^1$ include the groups represented by the formulae (Y1) to (Y29):

 (Y1)

 (Y2)

 (Y3)

 (Y4)

 (Y5)

 (Y6)

 (Y7)

(Y8) 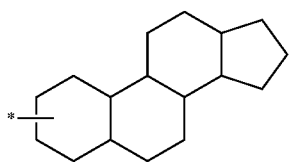
(Y9) 
(Y10) 
(Y11) 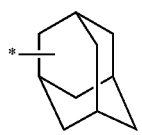
(Y12) 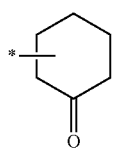
(Y13) 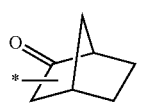
(Y14) 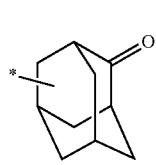
(Y15) 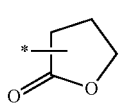
(Y16) 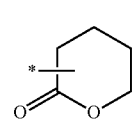
(Y17) 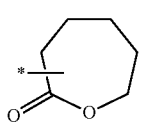
(Y18) 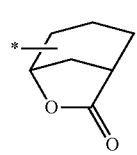
(Y19) 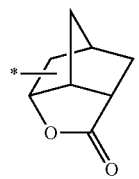
(Y20) 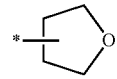
(Y21) 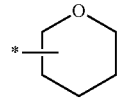
(Y22) 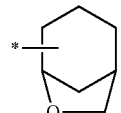
(Y23) 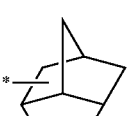
(Y24) 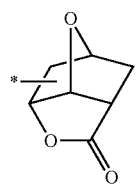
(Y25) 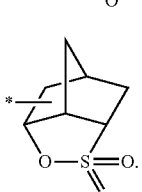
(Y26) 
Among them, preferred are the groups represented by the formulae (Y1) to (Y19), and more preferred are the groups represented by the formulae (Y11), (Y14), (Y15), (Y19), and still more preferred are the groups represented by the formulae (Y11) and (Y14).
Examples of $Y^1$ having one or more substituents include the followings:
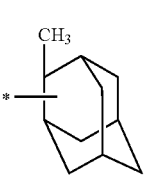

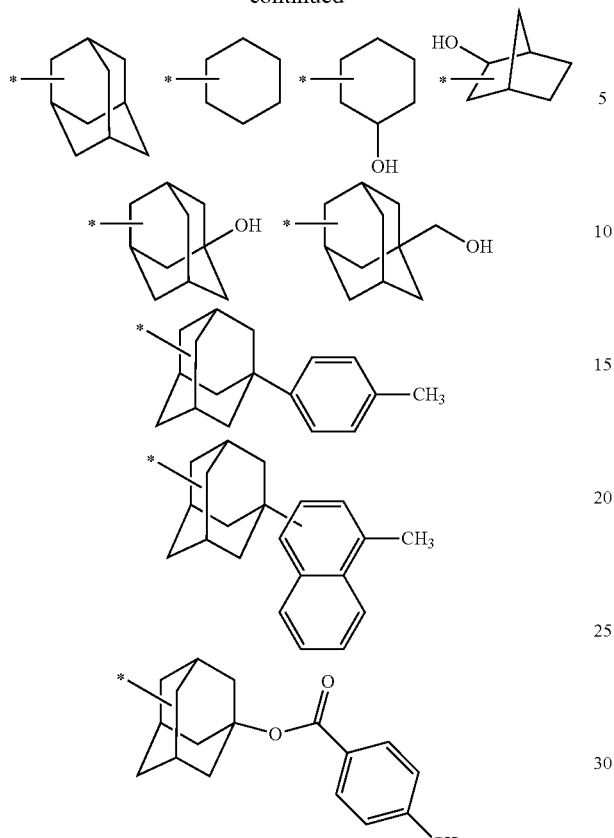

Y¹ is preferably a C3-C18 alicyclic hydrocarbon group which can have one or more substituents, and more preferably an adamantyl group which can have one or more substituents, and still more preferably an adamantyl group, a hydroxyadamantyl group or an oxoadamantyl group.

Among the sulfonic acid anions of the salt represented by the formula (II), preferred are anions represented by the formulae (IIa) to (IIi).

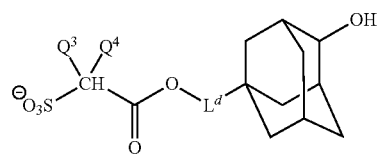
(IIa)

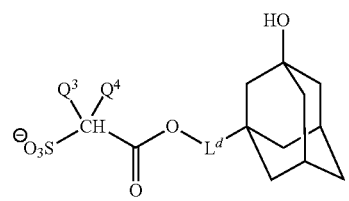
(IIb)

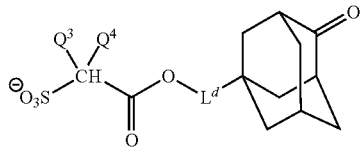
(IIc)

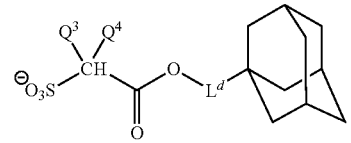
(IId)

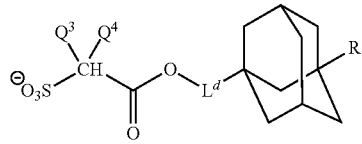
(IIe)

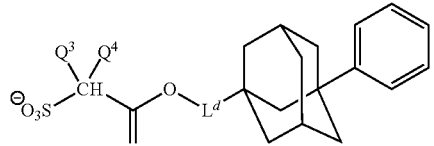
(IIf)

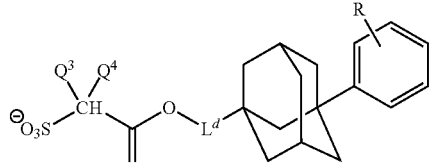
(IIg)

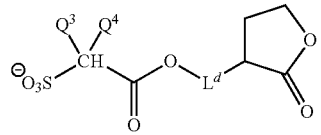
(IIh)

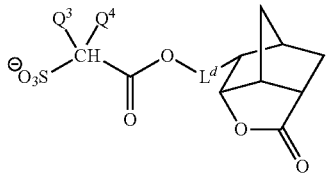
(IIi)

wherein $Q^3$, $Q^4$ and $L^d$ are the same as defined above, and R represents a C1-C4 aliphatic hydrocarbon group, preferably a methyl group.

Specific examples of the anion parts include the following.

-continued
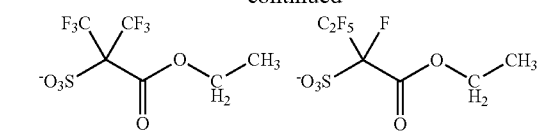
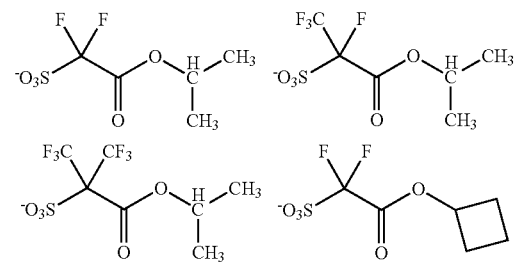
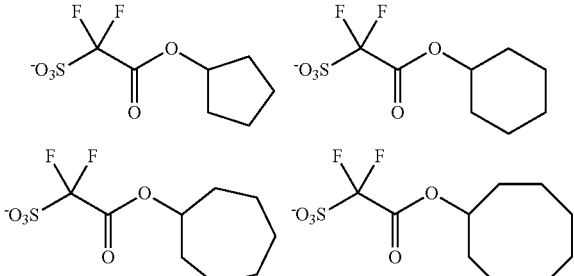
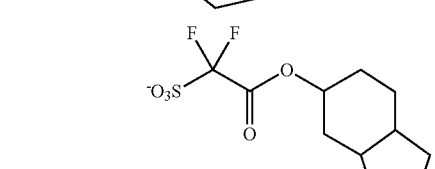
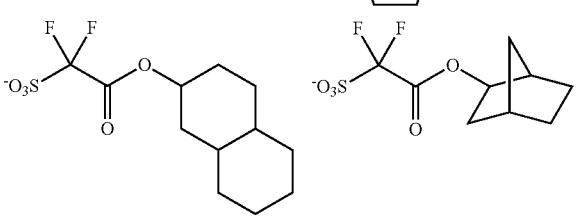
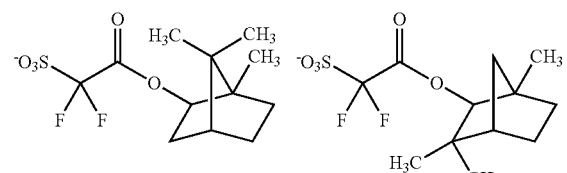
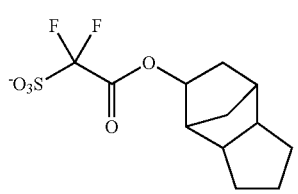
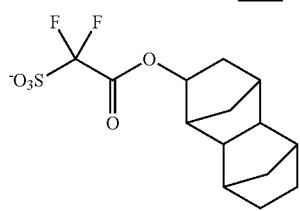
-continued
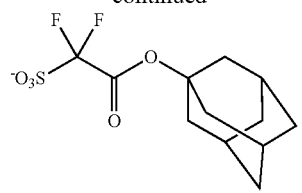
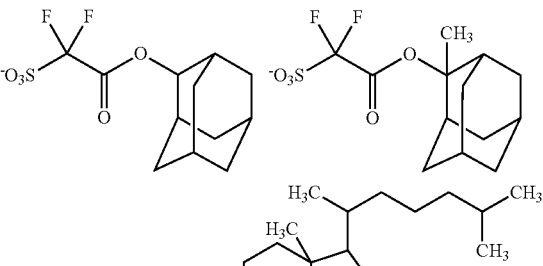
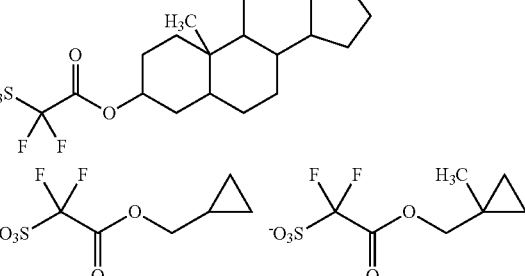
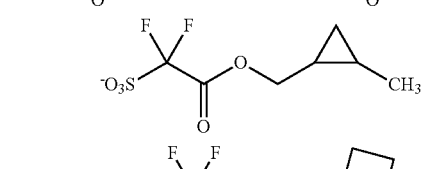
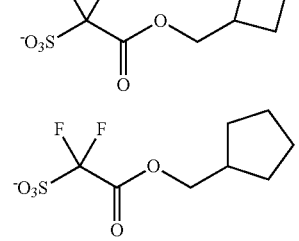
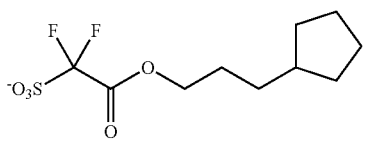
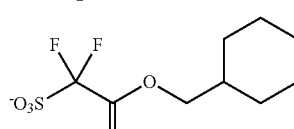
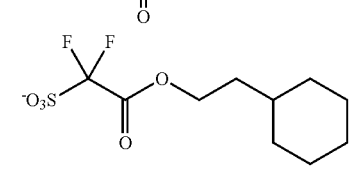
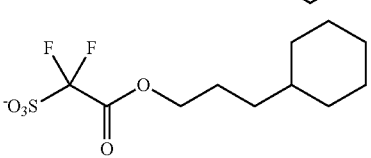

-continued
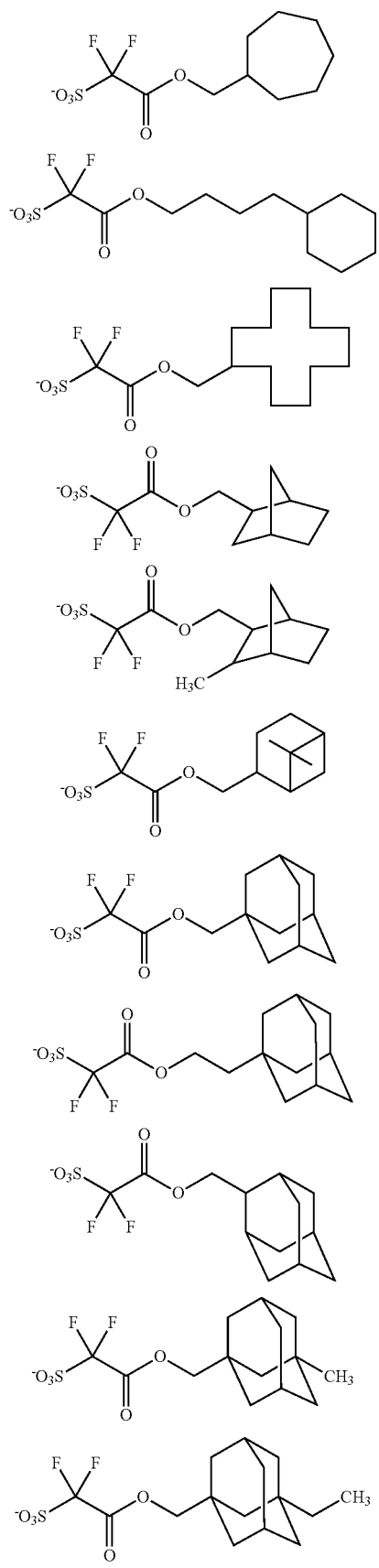
-continued
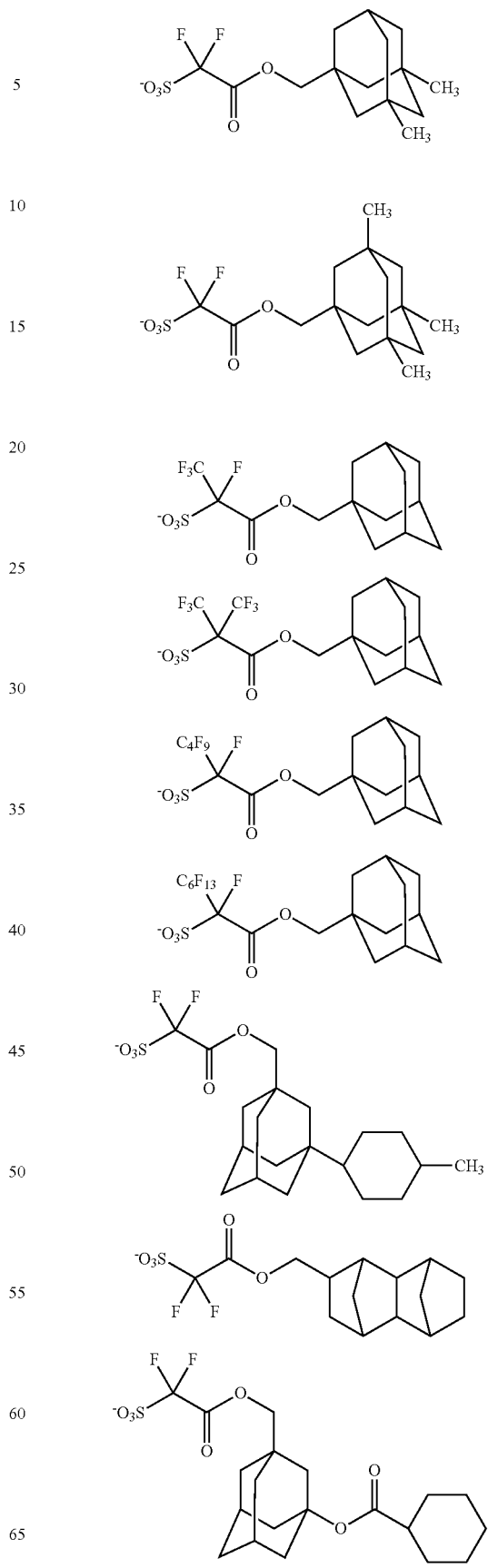

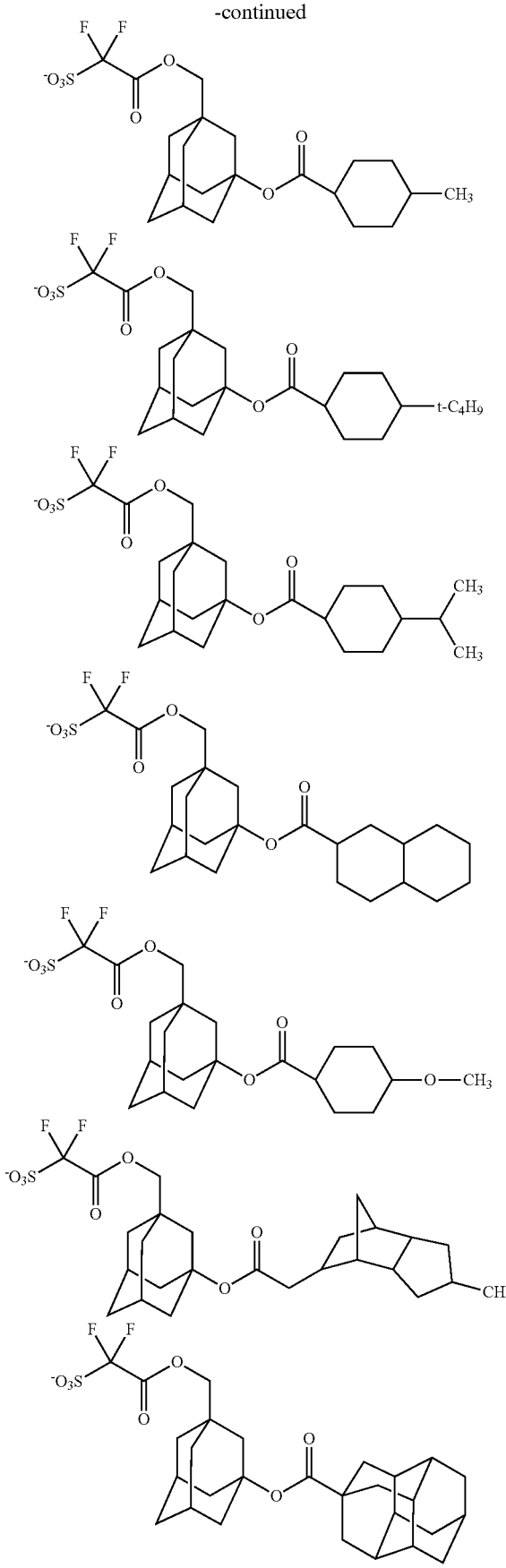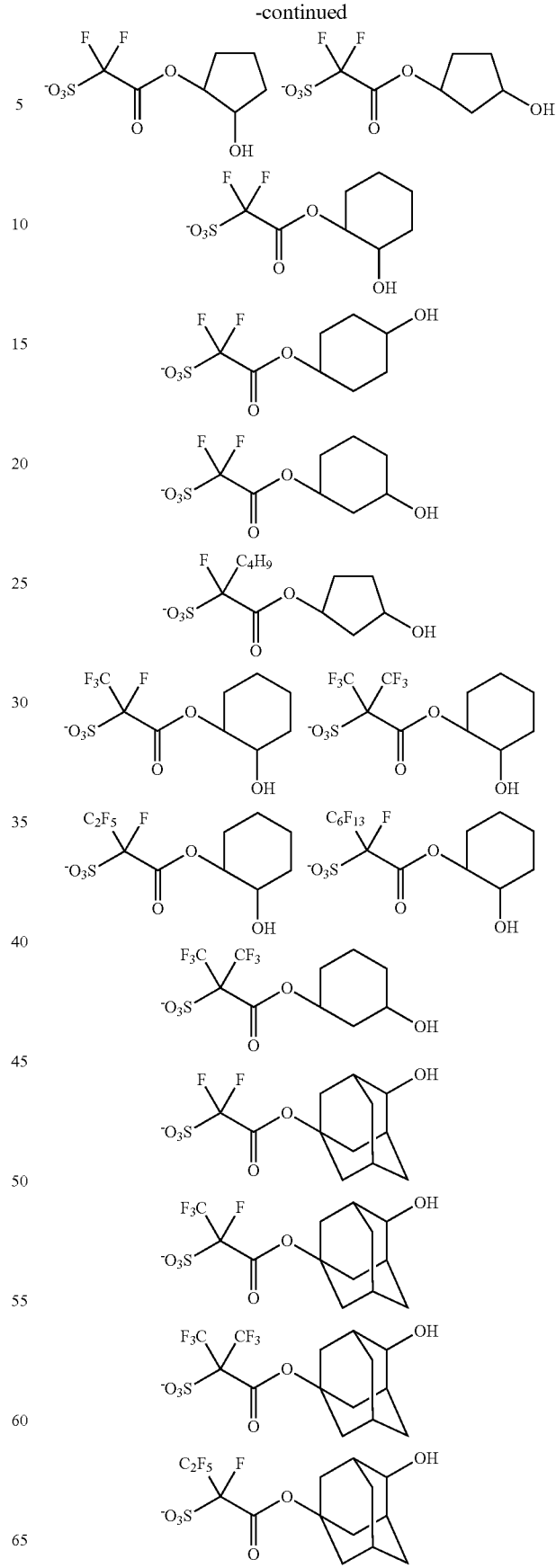

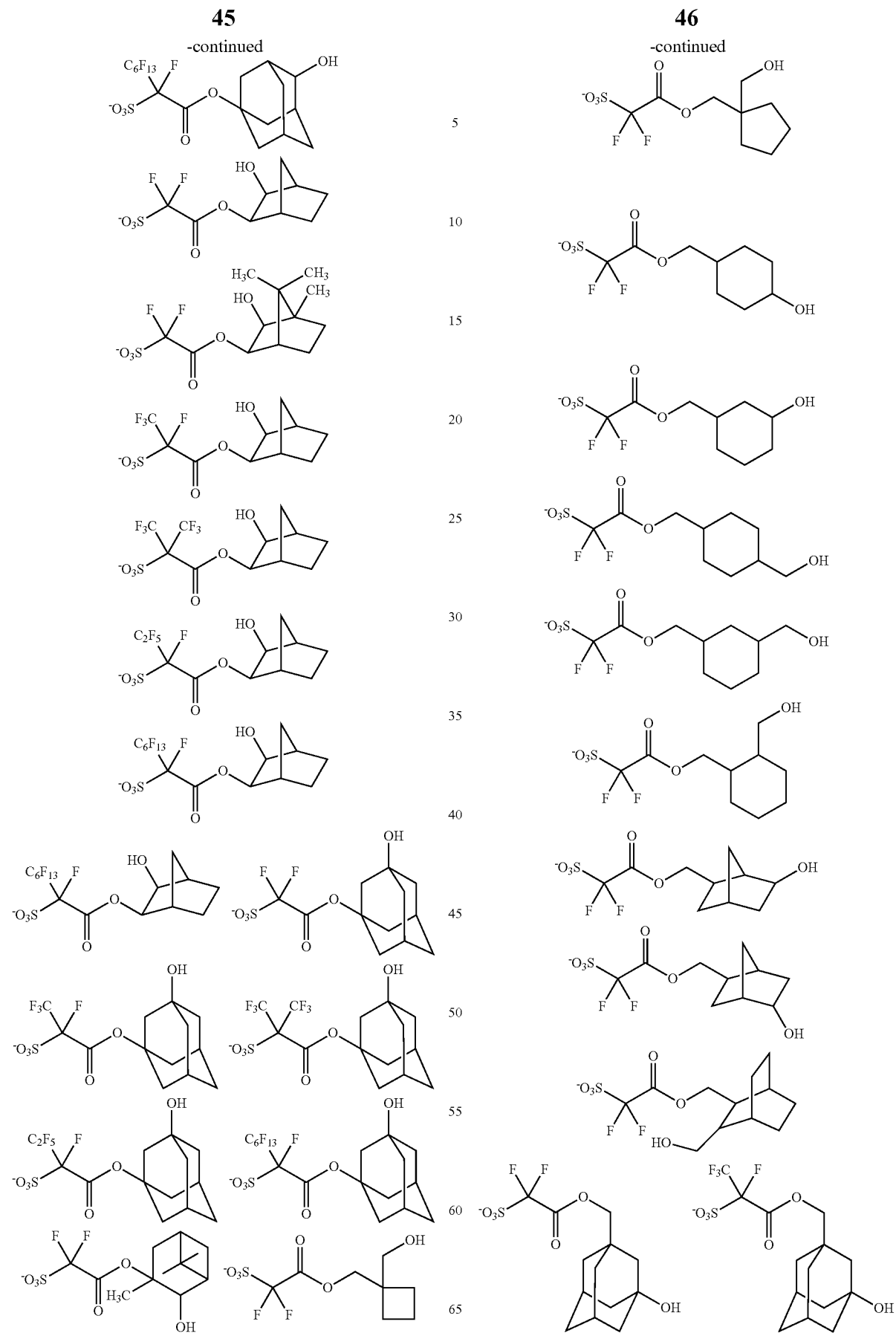

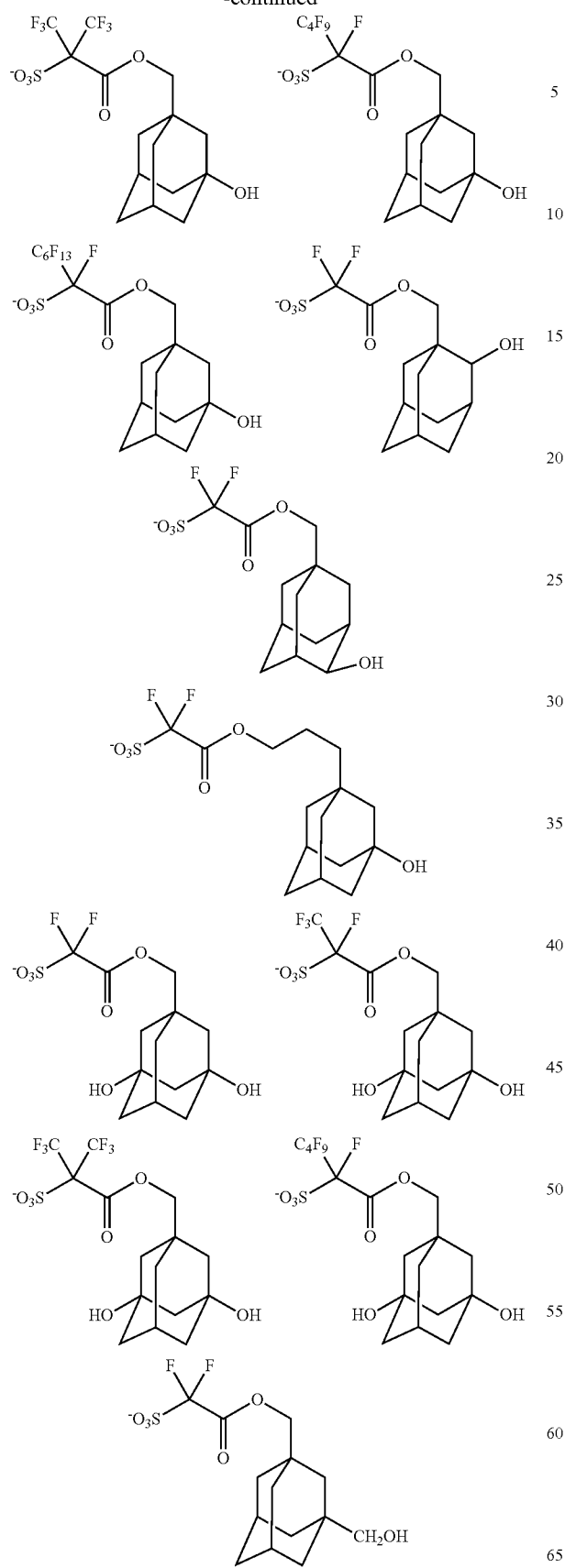
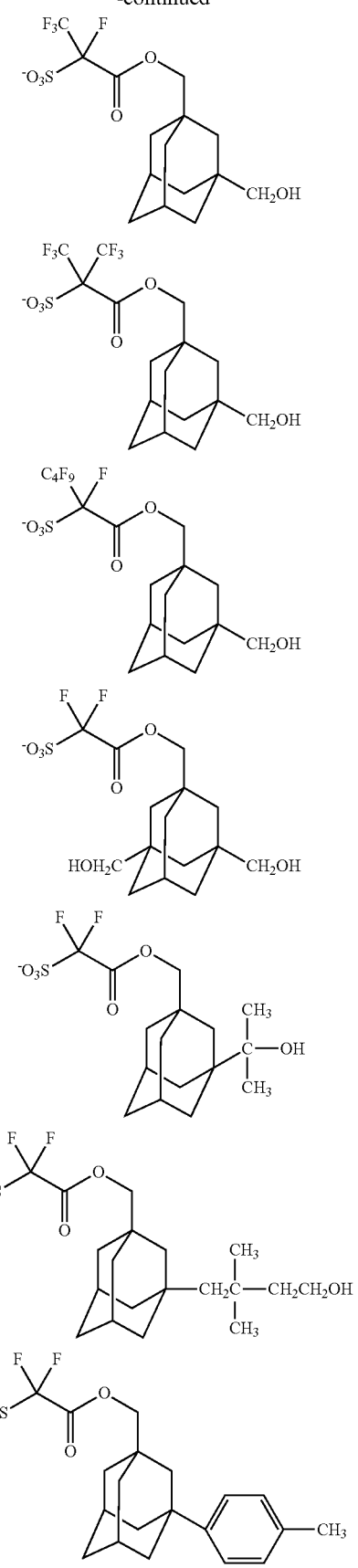

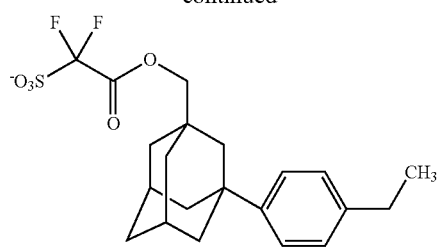
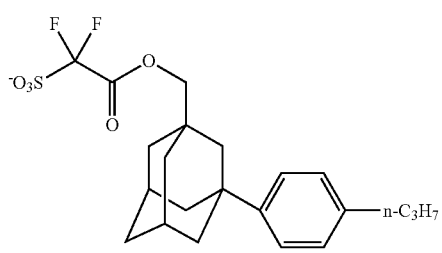
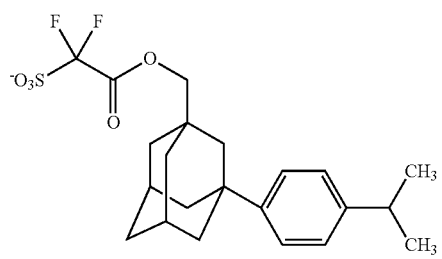
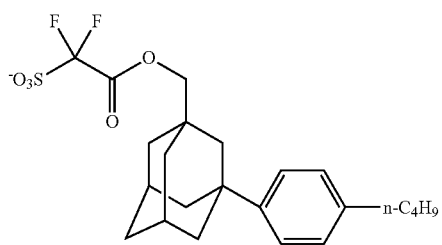
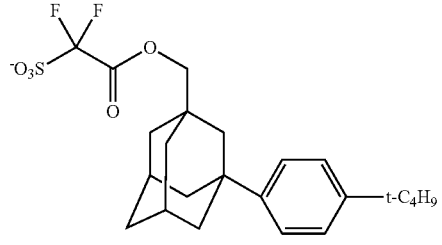
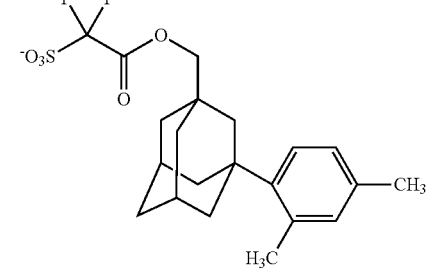
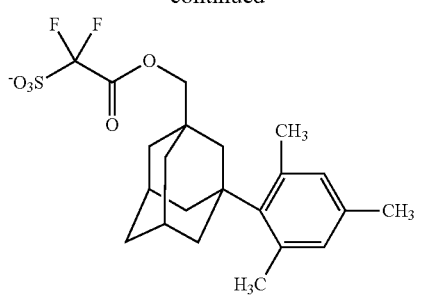
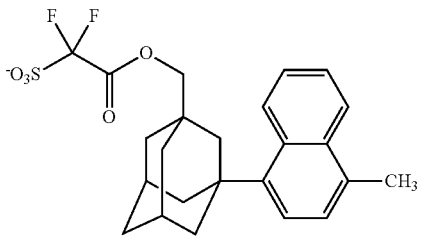
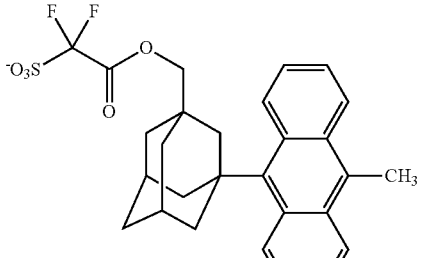
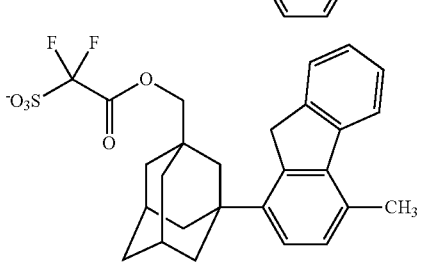
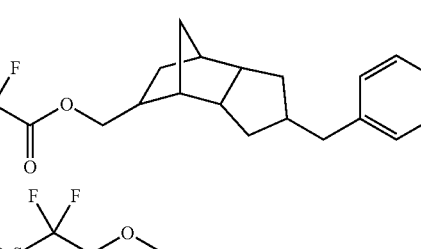
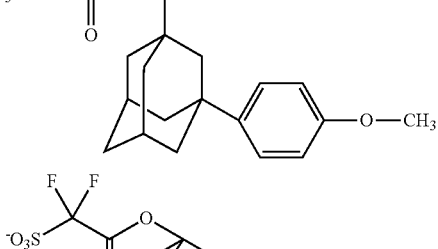
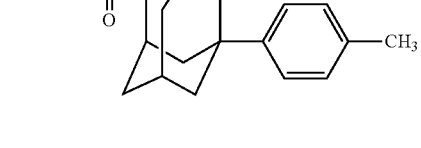

51
-continued
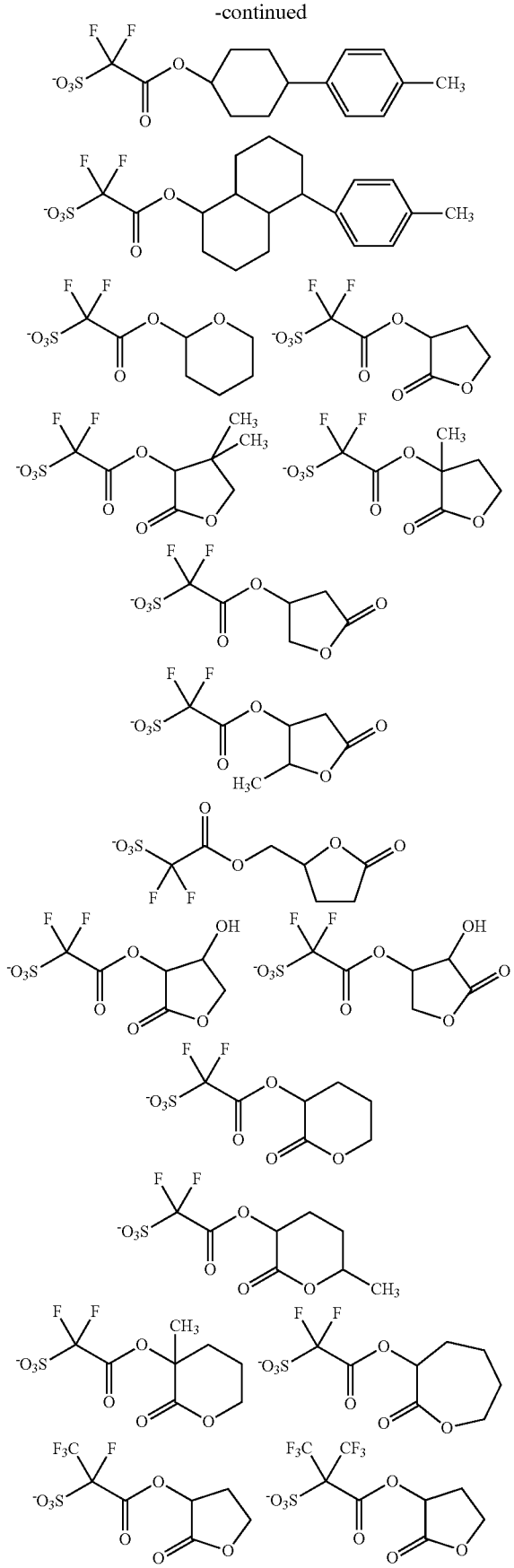
52
-continued
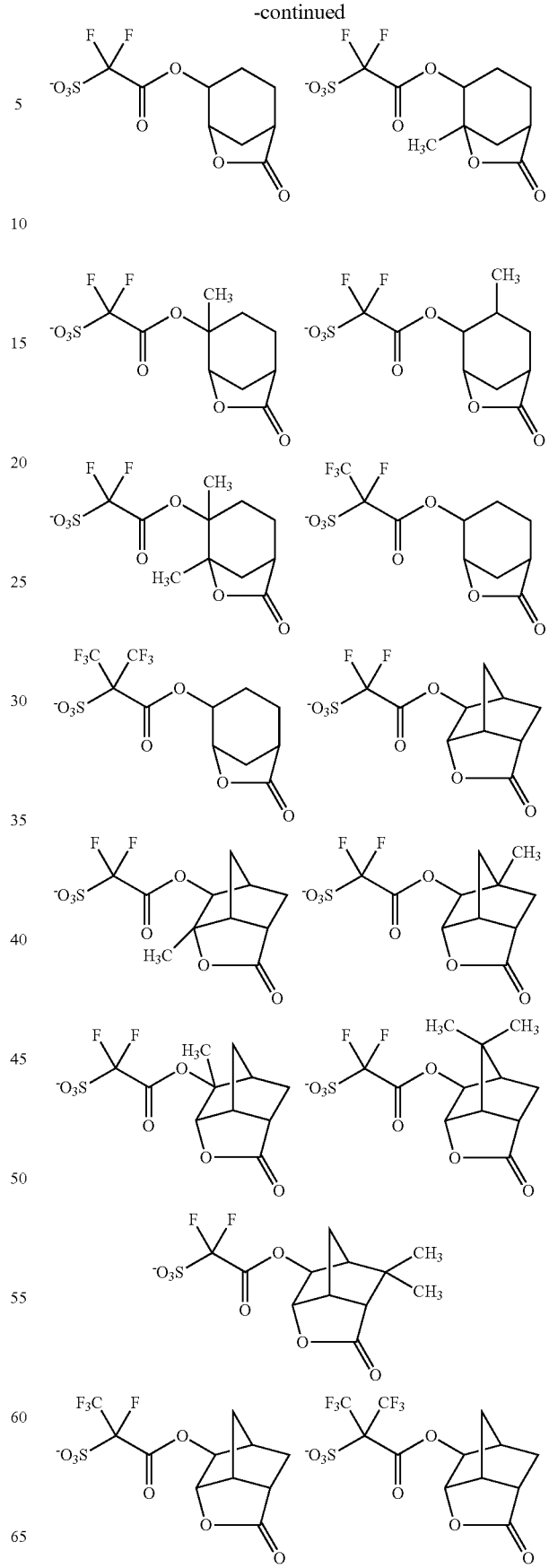

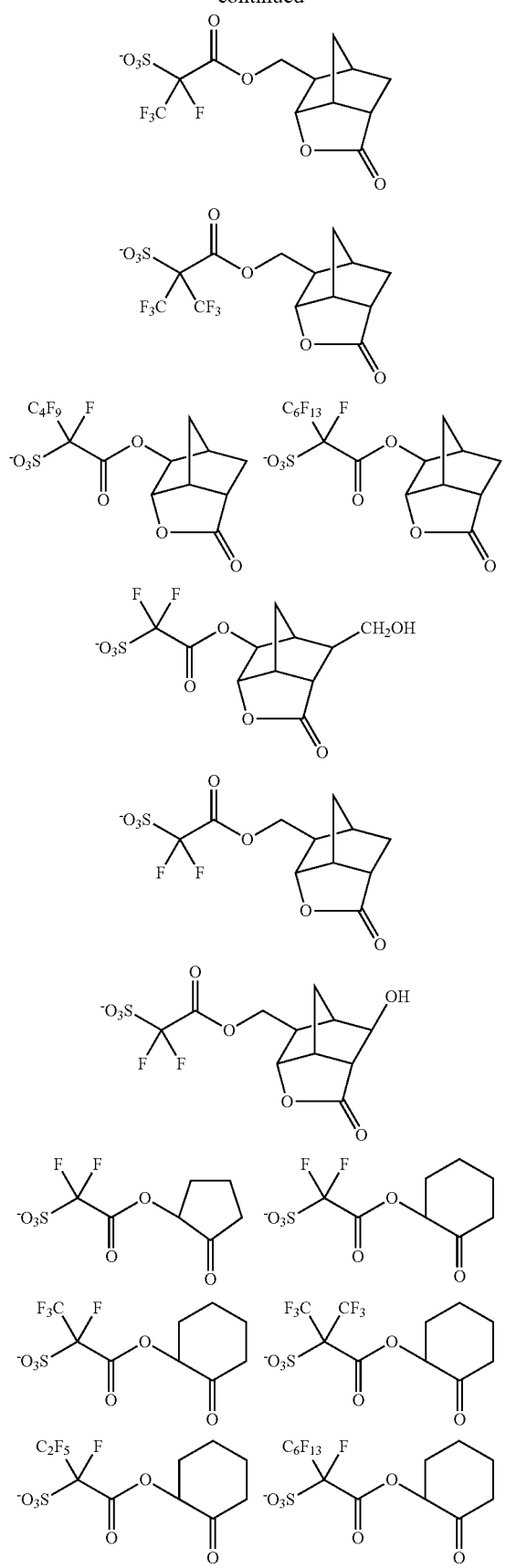
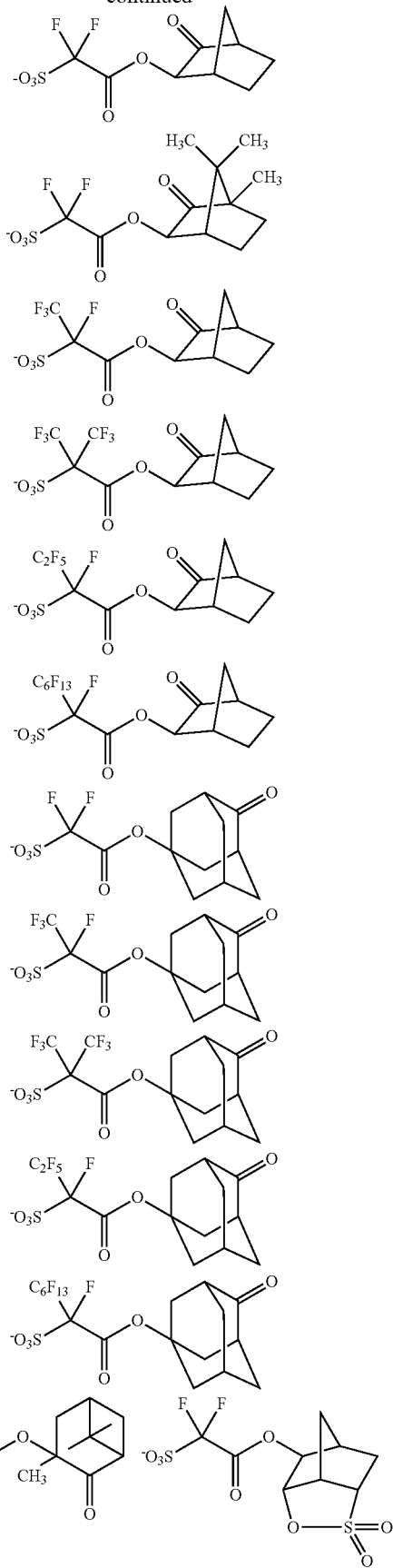

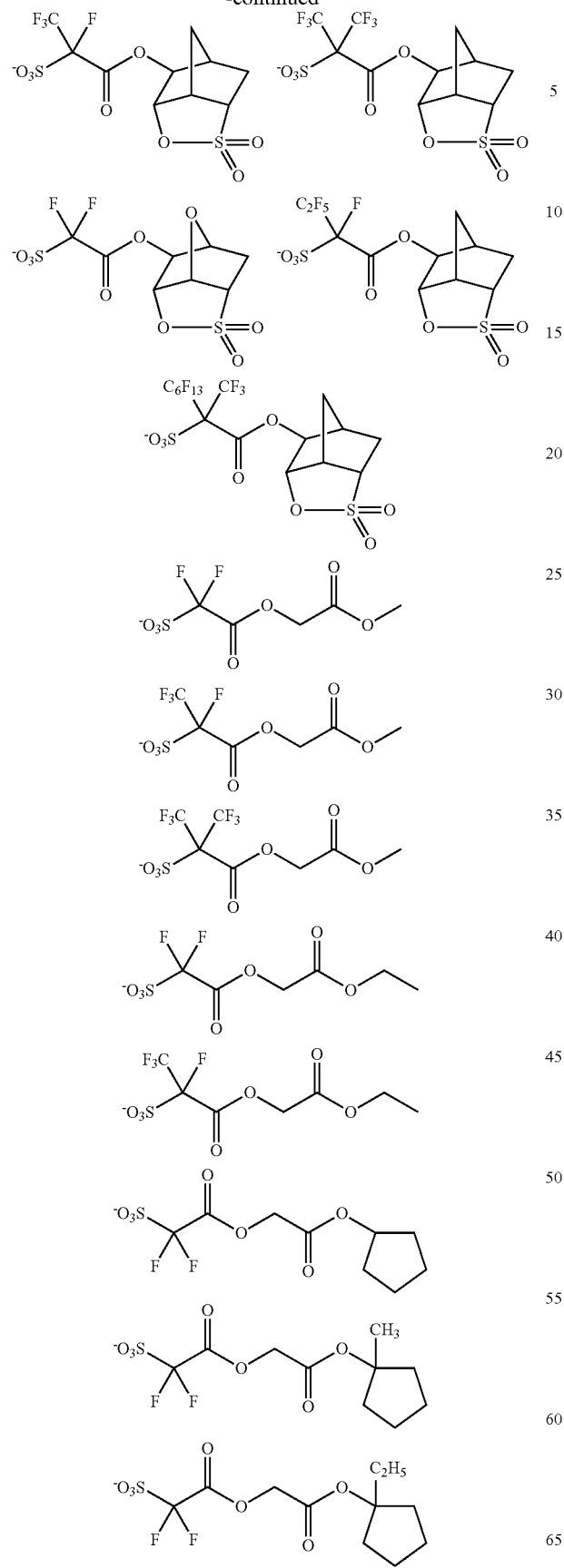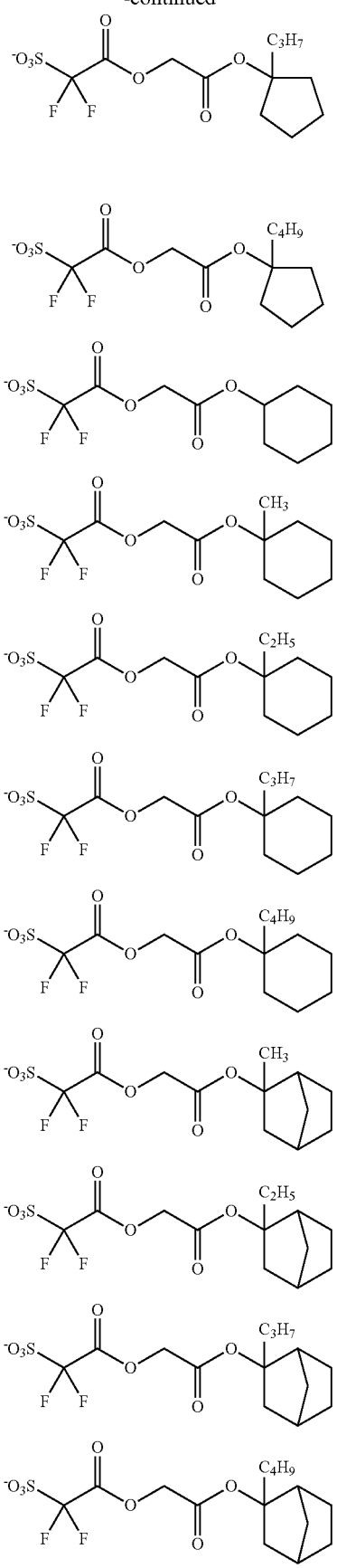

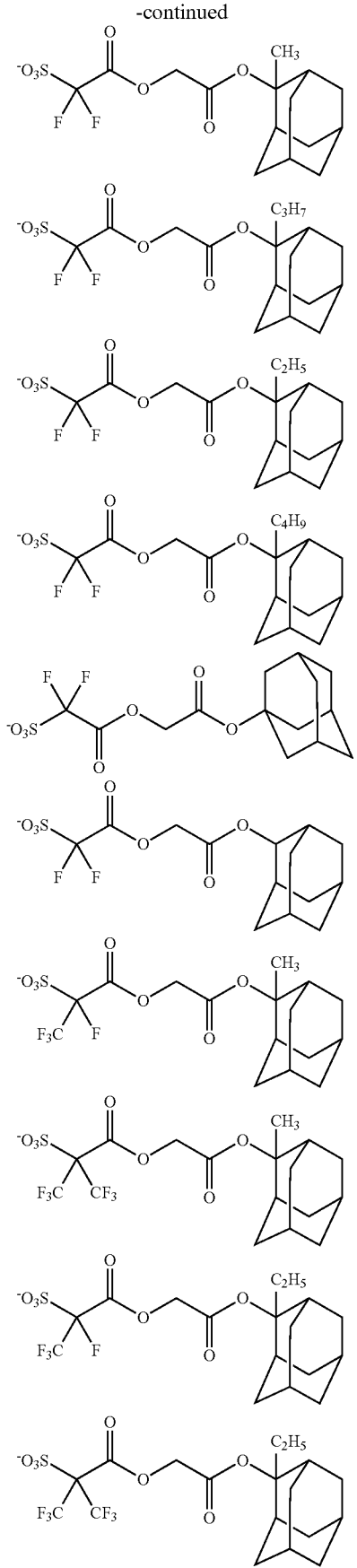
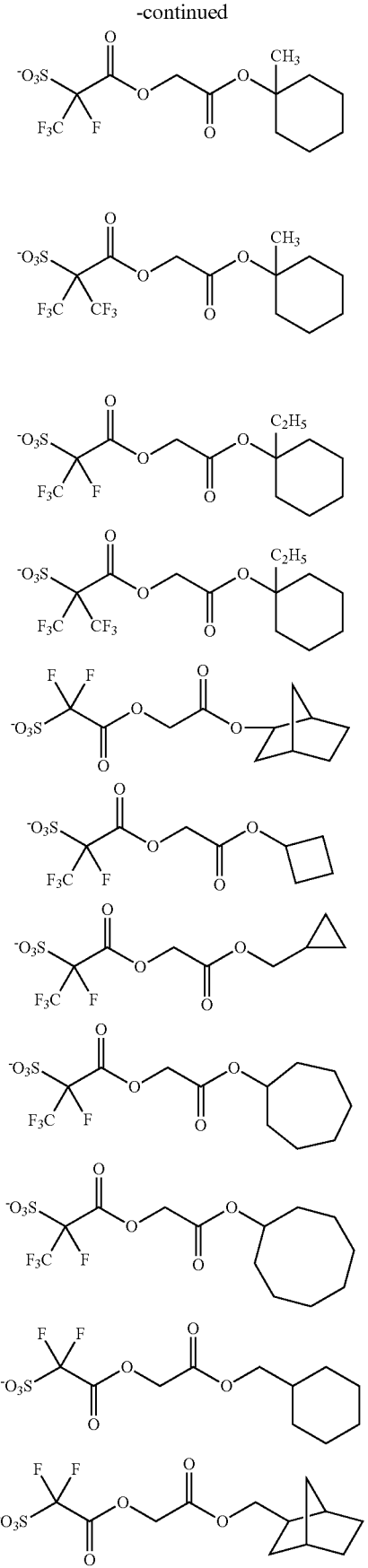

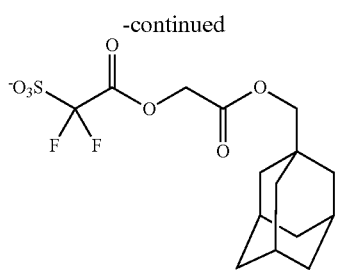
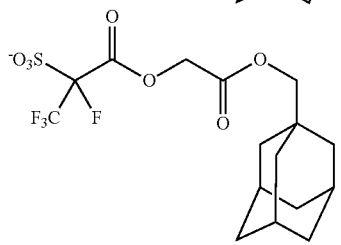
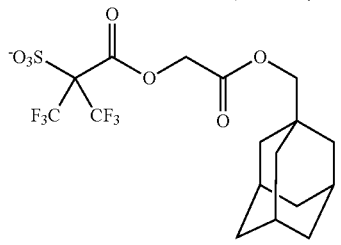
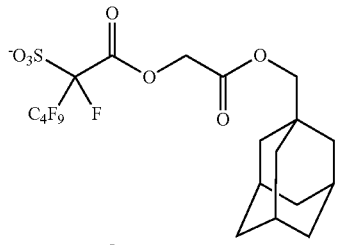
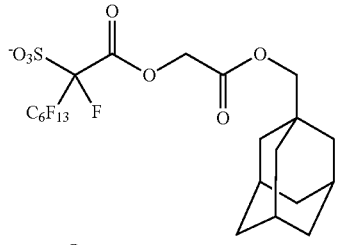
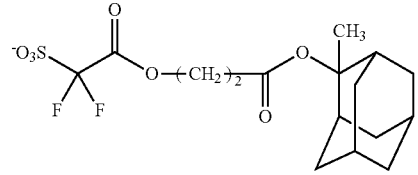
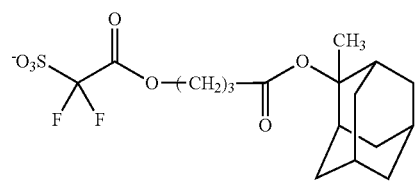
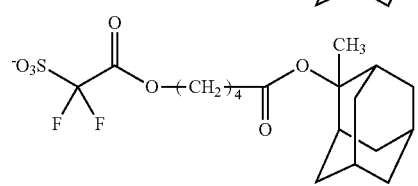
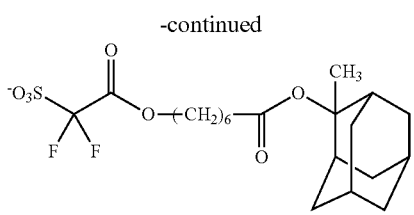
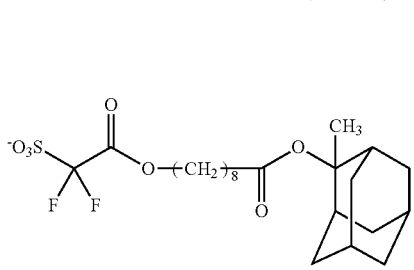
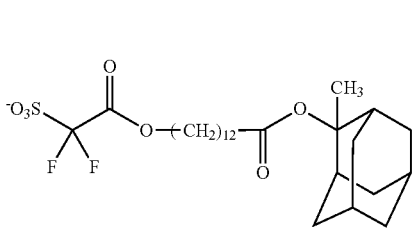
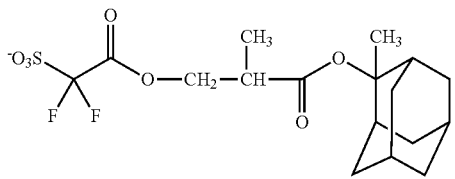
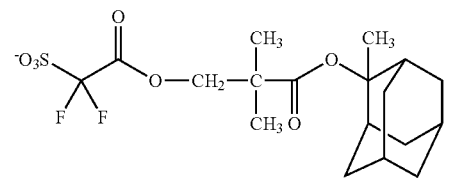
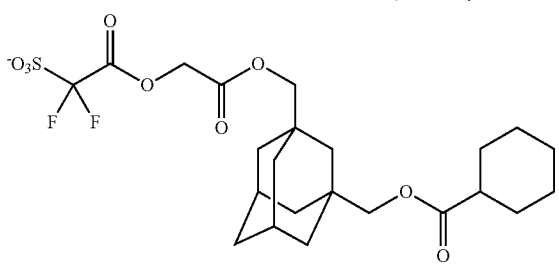
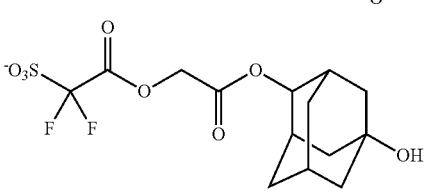
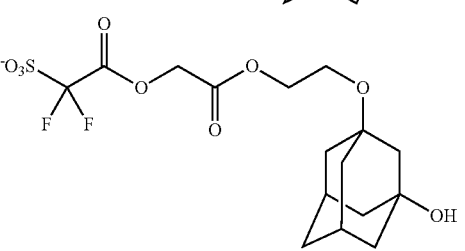

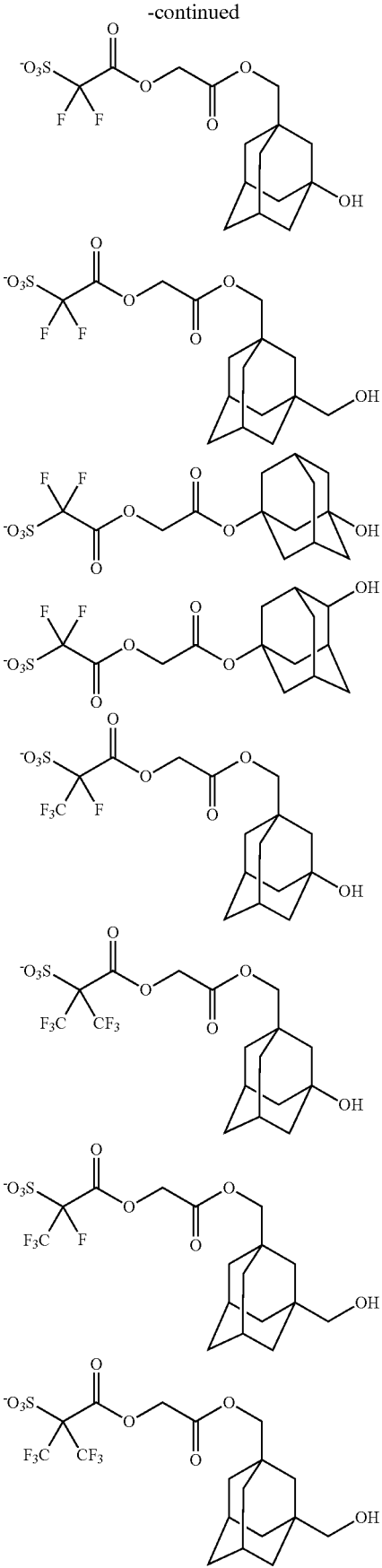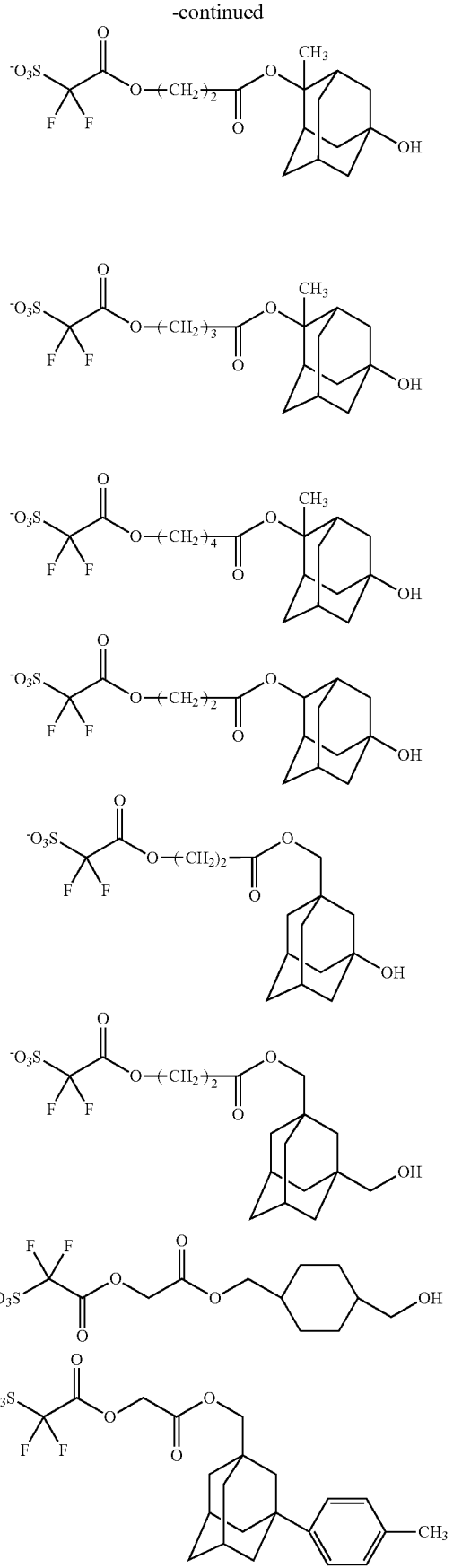

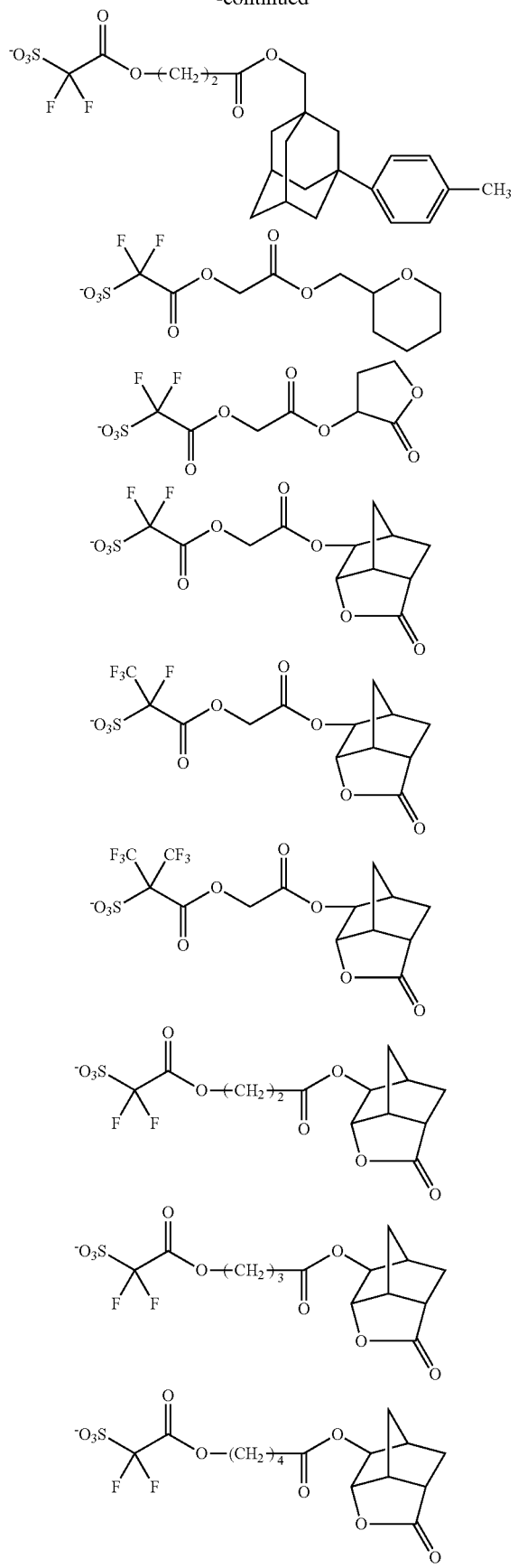
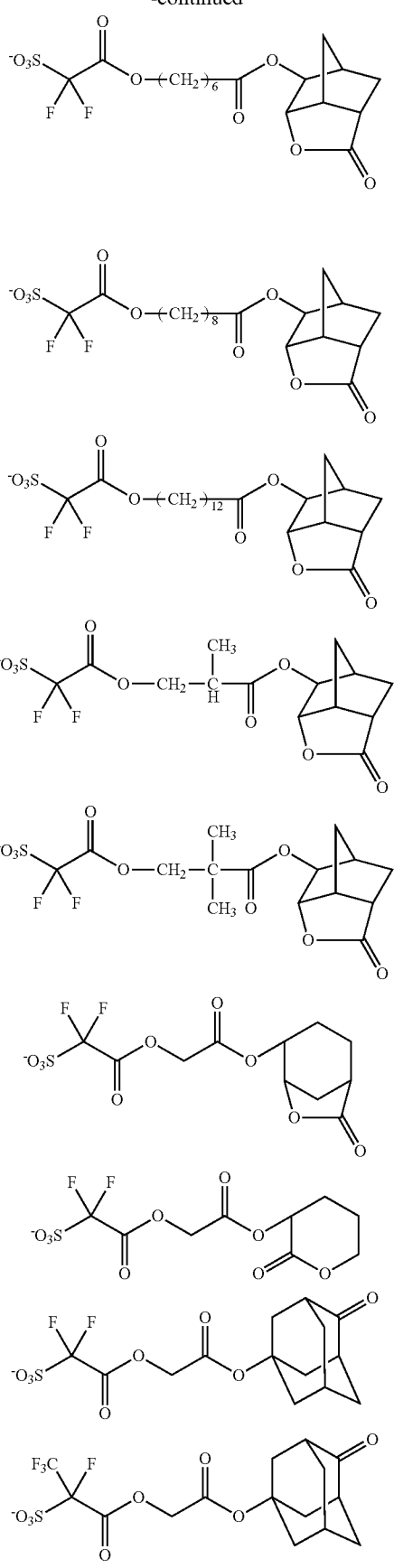

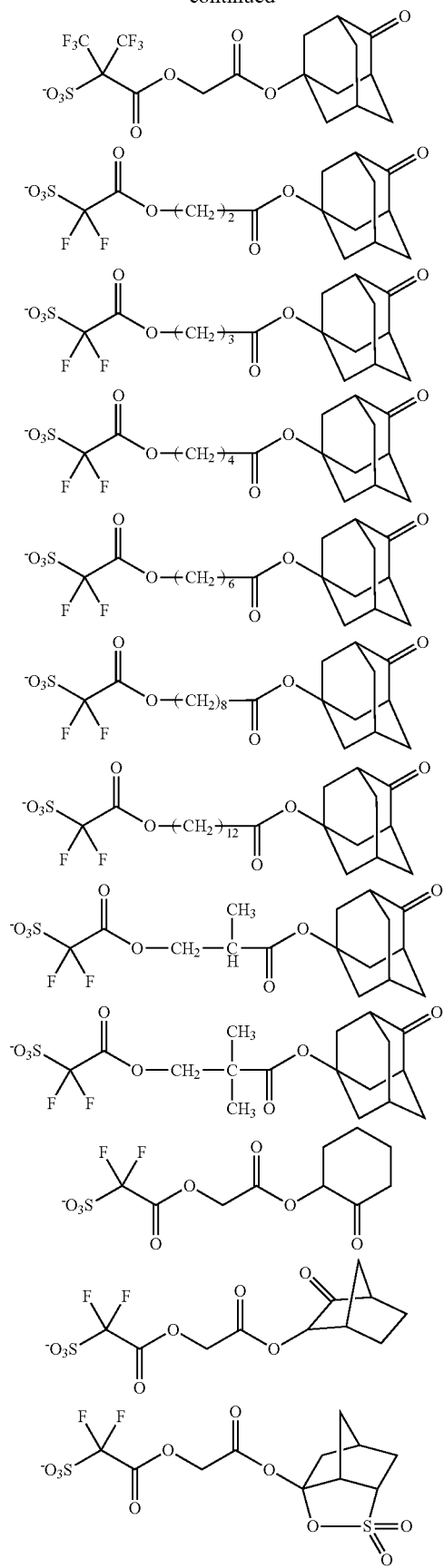
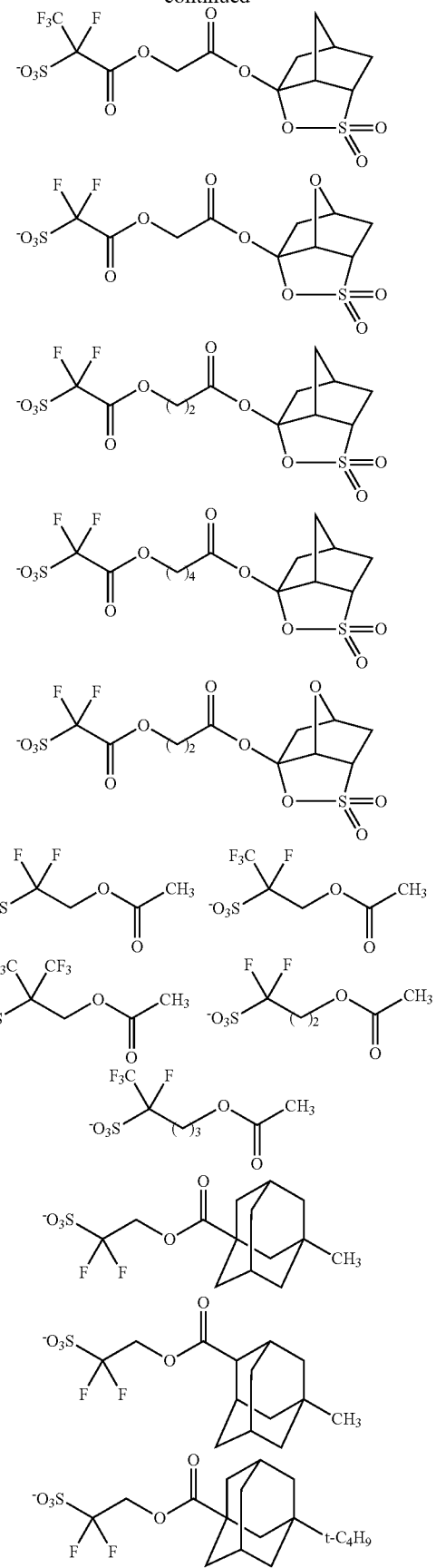

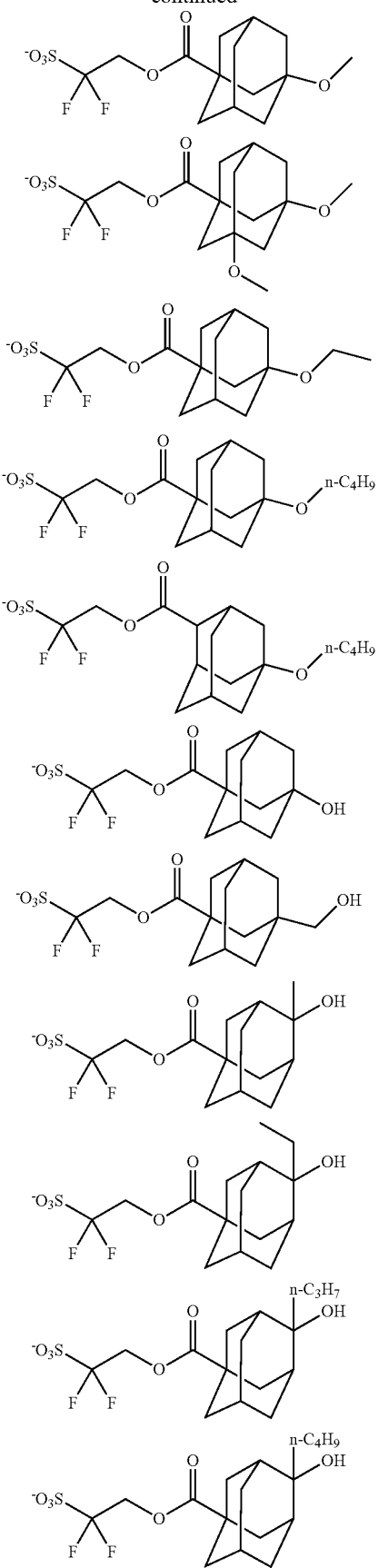
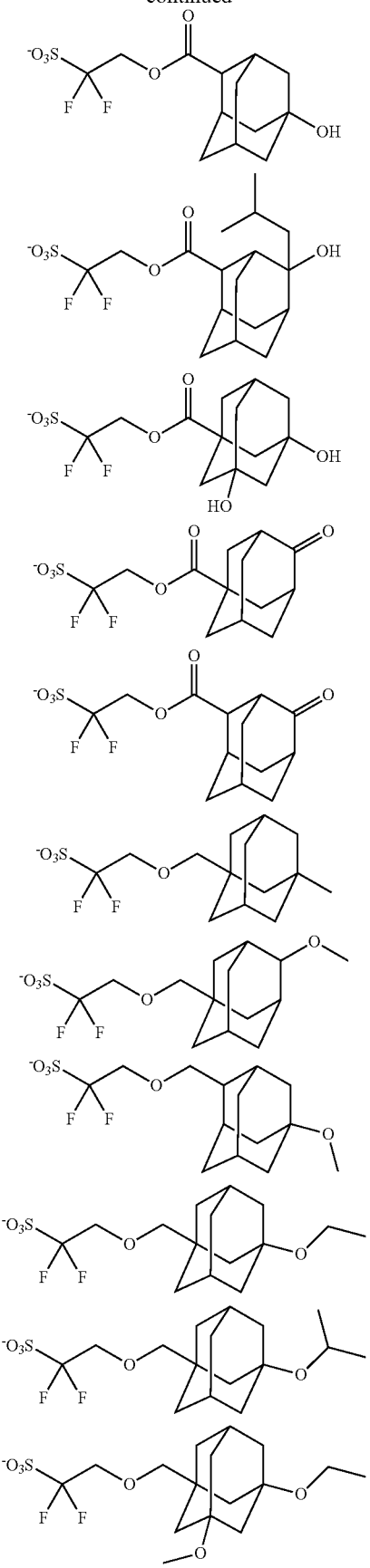

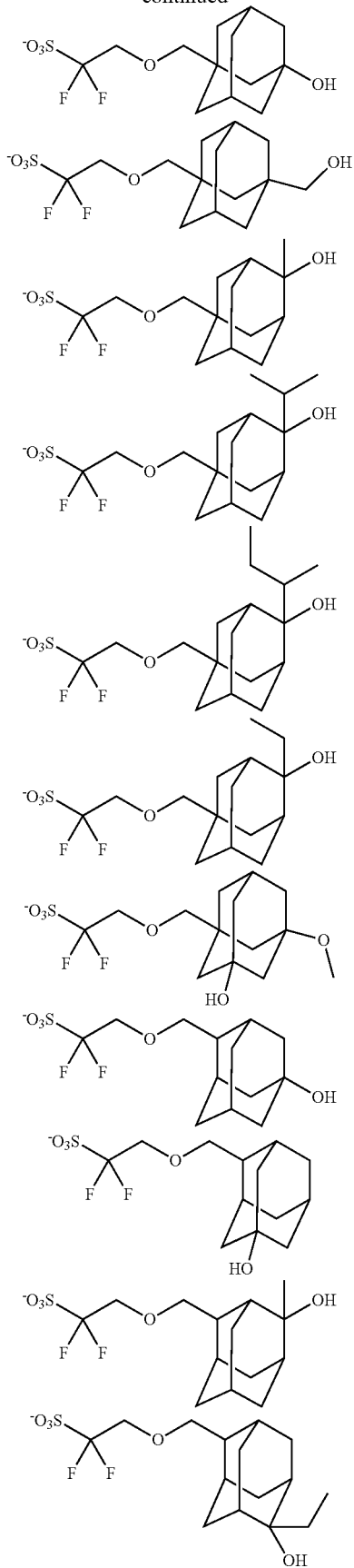
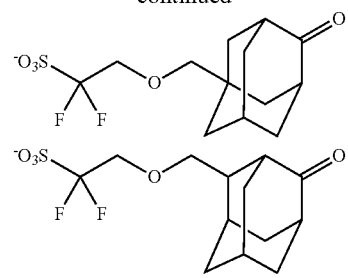
Among them, preferred are the following.
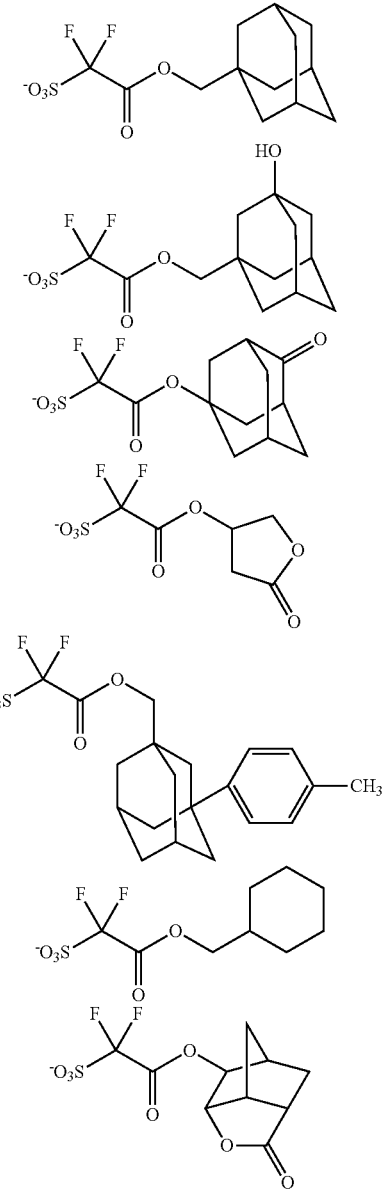
Examples of the cation part represented by include an organic onium cation such as a organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable.

Preferable examples of the cation part represented by $Z'^+$ include the cations represented by the above-mentioned formulae (b2-1) to (b2-4). Preferred is the cation represented by the formula (b2-1), and more preferred is the cation represented by the formula (b2-1-1), and still more preferred are a triphenylsulfonium cation and a tritolylsulfonium cation.

Examples of the known acid generators other than SALT (I) include a salt consisting of any one of the above-mentioned anions and any one of the above-mentioned cations. Specific examples thereof include a salt consisting of any one of the anions represented by the formulae (IIa) to (IIi) and the cation represented by the formula (b2-1-1), and a salt consisting of any one of the anions represented by the formulae (IIc) to (IIe) and the cation represented by the formula (b2-3).

Preferable examples of the known acid generators other than SALT (I) include the following salts represented by the formulae (B1-1) to (B1-20), and the salt containing a triphenylsulfonium cation or a tritolylsulfonium cation is more preferable, and the salts represented by the formulae (B1-1), (B1-2), (B1-3), (B1-6), (B1-7), (B1-11), (B1-12), (B1-13) and (B1-14) are especially preferable.

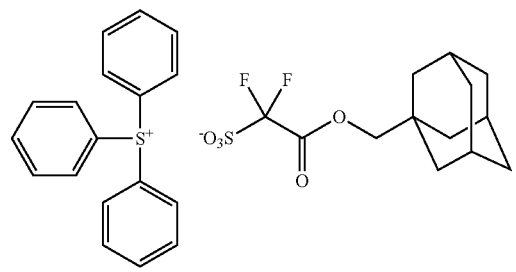

(B1-1)

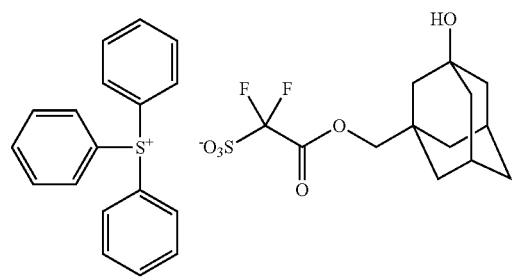

(B1-2)

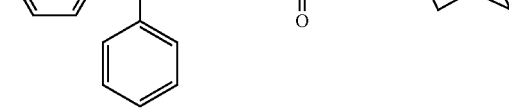

(B1-3)

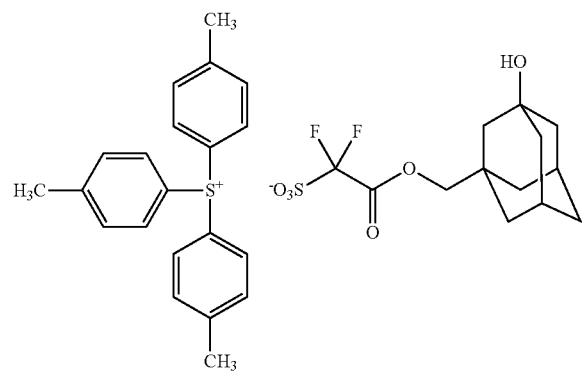

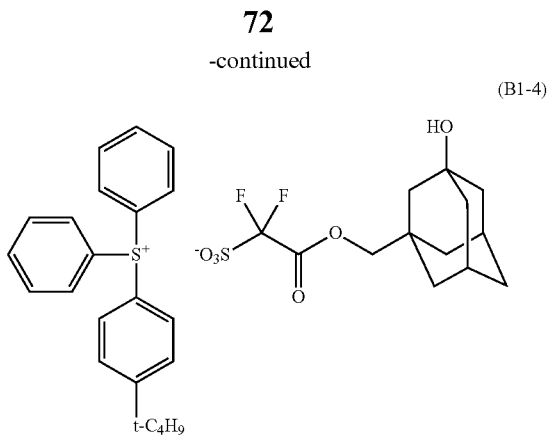

(B1-4)

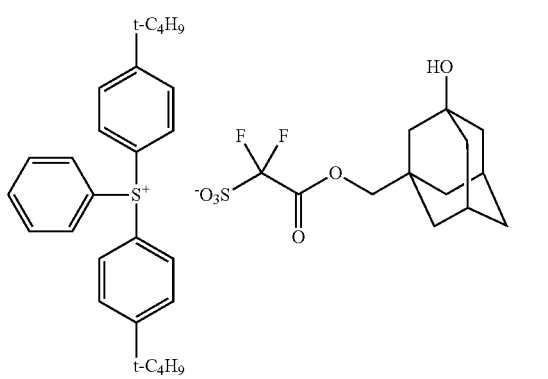

(B1-5)

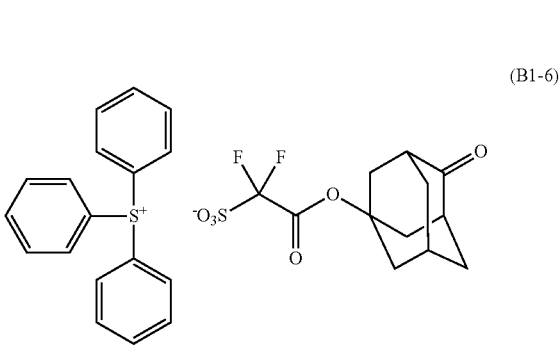

(B1-6)

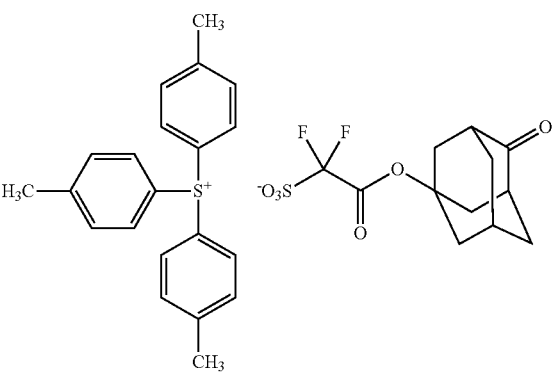

(B1-7)

(B1-8)
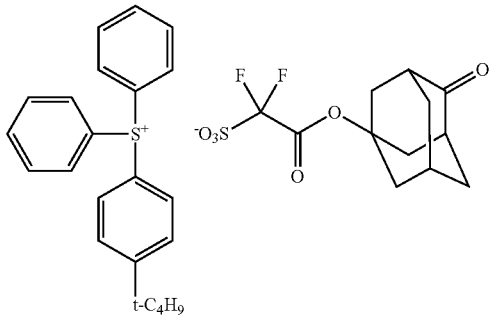
(B1-9)
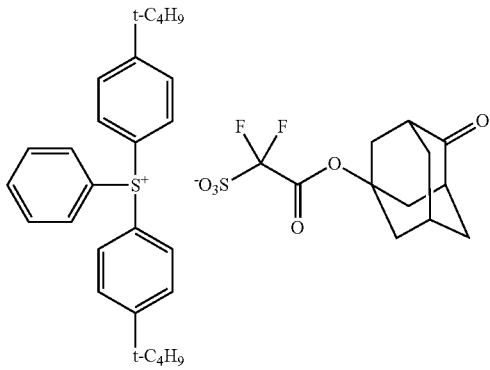
(B1-10)
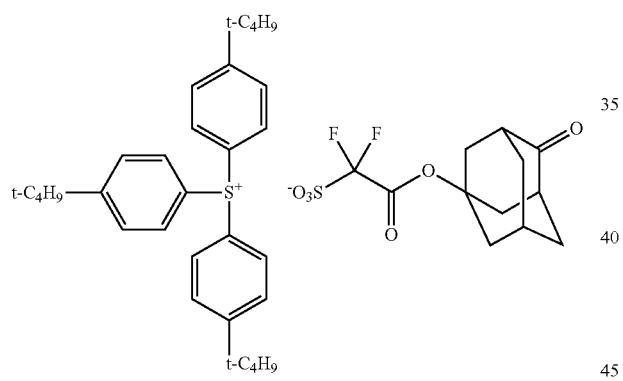
(B1-11)
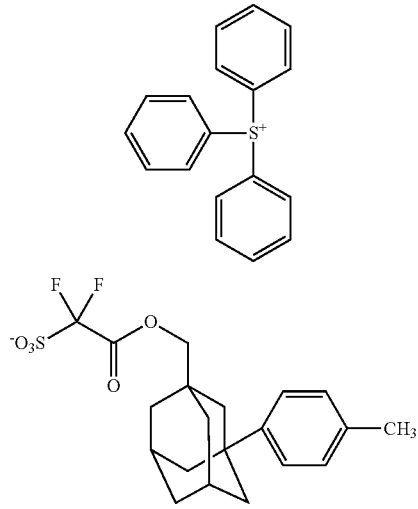
(B1-12)
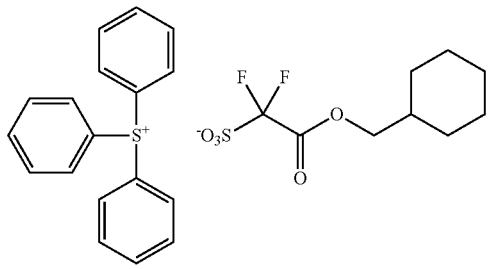
(B1-13)
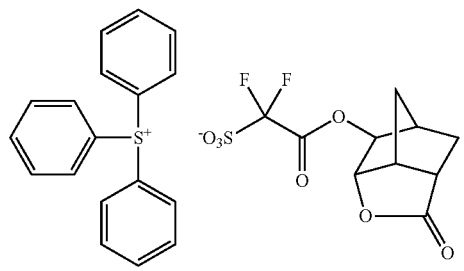
(B1-14)
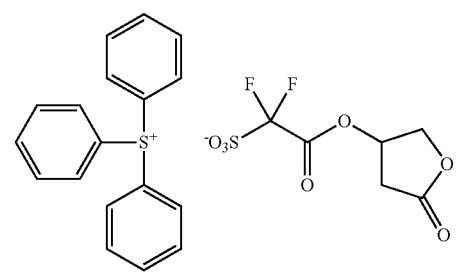
(B1-15)
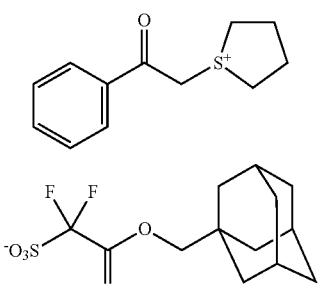
(B1-16)
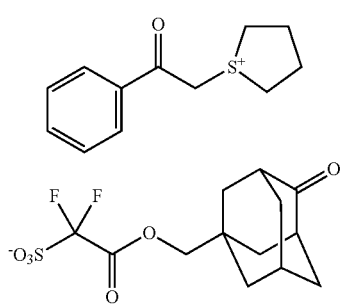

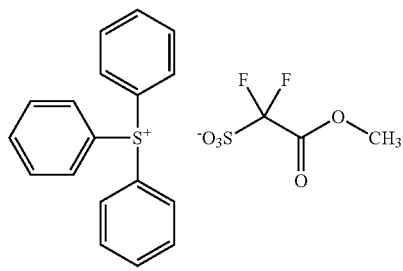

(B1-17)

(B1-18)

(B1-19)

(B1-20)

The acid generator of the present invention may consist of SALT (I). The content of SALT (I) in the acid generator of the present invention is preferably 10 parts by mass or more per 100 parts by mass of the acid generator of the present invention, and more preferably 30 parts by mass or more. The content of SALT (I) in the acid generator of the present invention is preferably 100 parts by mass or less per 100 parts by mass of the acid generator of the present invention, and more preferably 95 parts by mass or less, and still more preferably 90 parts by mass or less. When the acid generator of the present invention contains SALT (I) and the known acid generator other than SALT (I), the mass ratio of SALT (I) to known acid generator (SALT (I)/known acid generator) is usually 5/95 to 95/5, preferably 10/90 to 90/10, and more preferably 15/85 to 85/15.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid.

The content of SALT (I) in the photoresist composition of the present invention is preferably 0.1 part by mass or more per 100 parts by mass of the resin, and more preferably 0.2 part by mass or more. The content of SALT (I) in photoresist composition of the present invention is preferably 10 parts by mass or less per 100 parts by mass of the resin of the present invention, and more preferably 5 parts by mass or less. When the known acid generator other than SALT (I) is contained in the photoresist composition of the present invention, the content of the known acid generator is preferably 1 part by mass or more, and more preferably 3 parts by mass or more. The content of the known acid generator is preferably 30 parts by mass or less, and more preferably 25 parts by mass or less.

The resin is insoluble or poorly soluble in an alkali aqueous solution but becomes soluble in an alkali aqueous solution by the action of an acid. The resin has one or more acid-labile groups. In this specification, "an acid-labile group" means a group capable of being eliminated by the action of an acid.

Examples of the acid-labile group include a group represented by the formula (1):

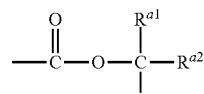

(1)

wherein $R^{a1}$, $R^{a2}$ and $R^{a3}$ independently each represent a C1-C8 aliphatic hydrocarbon group or a C3-C20 alicyclic hydrocarbon group, and $R^{a1}$ and $R^{a2}$ can be bonded each other to form a C3-C20 ring together with a carbon atom to which $R^{a1}$ and $R^{a2}$ are bonded, and one or more —CH$_2$— in the aliphatic hydrocarbon group, the alicyclic hydrocarbon group and the ring can be replaced by —O—, —S— or —CO—.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

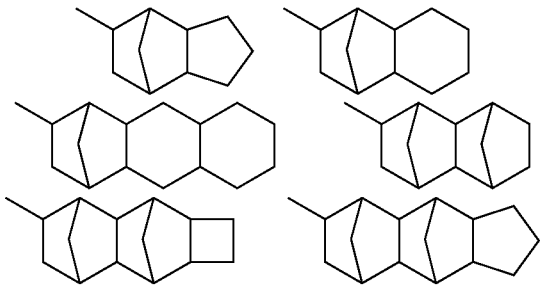

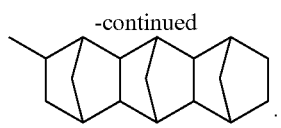

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

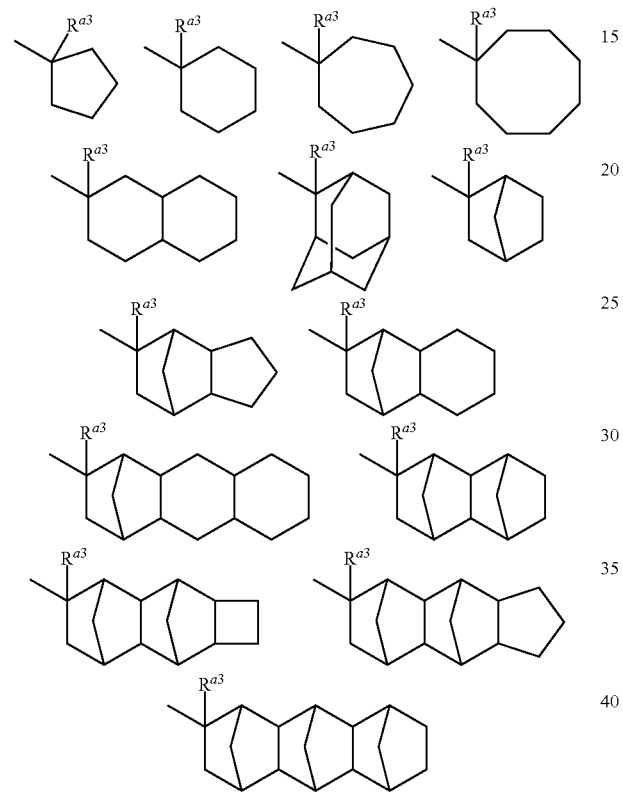

wherein $R^{a3}$ is the same as defined above.

The group represented by the formula (I) wherein $R^{a1}$, $R^{a2}$ and $R^{a3}$ independently each represent a C1-C8 alkyl group such as a tert-butyl group, the group represented by the formula (I) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (I) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The compound having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain.

A monomer having the group represented by the formula (1) in its side chain and a carbon-carbon double bond is preferable, and an acrylate monomer having the group represented by the formula (1) in its side chain or a methacryalte monomer having the group represented by the formula (1) in its side chain is more preferable.

An acrylate monomer having the group represented by the formula (1) in which $R^{a1}$ and $R^{a2}$ are bonded each other to form a C5-C20 alicycle together with the carbon atom to which they are bonded in its side chain or a methacryalte monomer having the group represented by the formula (1) in which $R^{a1}$ and $R^{a2}$ are bonded each other to form a C5-C20 alicycle together with the carbon atom to which they are bonded in its side chain is especially preferable.

Preferable examples of the structural unit derived from the monomer having an acid-labile group include the structural units represented by the formulae (a1-1) and (a1-2):

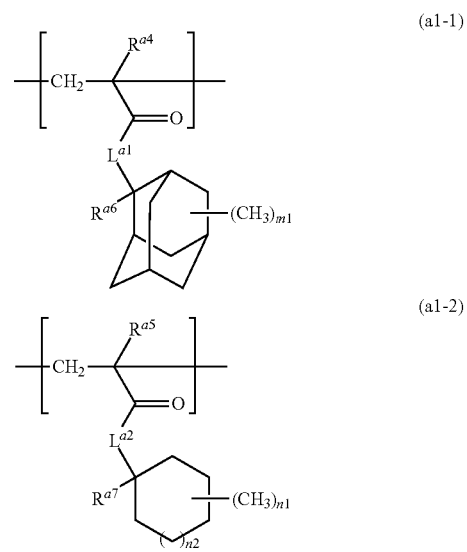

wherein $R^{a4}$ and $R^{a5}$ each independently represents a hydrogen atom or a methyl group, $R^{a6}$ and $R^{a7}$ each independently represents a C1-C8 alkyl group or a C3-C10 alicyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n2 represents an integer of 0 to 3.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

$R^{a4}$ and $R^{a5}$ are preferably methyl groups.

It is preferred that $R^{a6}$ and $R^{a7}$ independently each represent C1-C8 alkyl group or C3-C8 alicyclic hydrocarbon group, and it is more preferred that $R^{a6}$ and $R^{a7}$ independently each represent C1-C6 alkyl group or C3-C6 alicyclic hydrocarbon group. The alicyclic hydrocarbon group may be monocyclic or polycyclic. The alicyclic hydrocarbon group is preferably a saturated aliphatic cyclic hydrocarbon group. Examples of the alkyl group include a methyl group, an ethyl group, a propyl group, an isopropyl group, a tert-butyl group, a 2,2-dimethylethyl group, a propyl group, a 1-methylpropyl group, a 2,2-dimethylpropyl group, a 1-ethylpropyl group, a butyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the alicyclic hydrocarbon group include a cyloheptyl group, a methylcyloheptyl group, a cyclohexyl group, a methylcyclohexyl group, a dimethylcyclohexyl group, a norbornyl group, a methylnorbornyl group and the following.

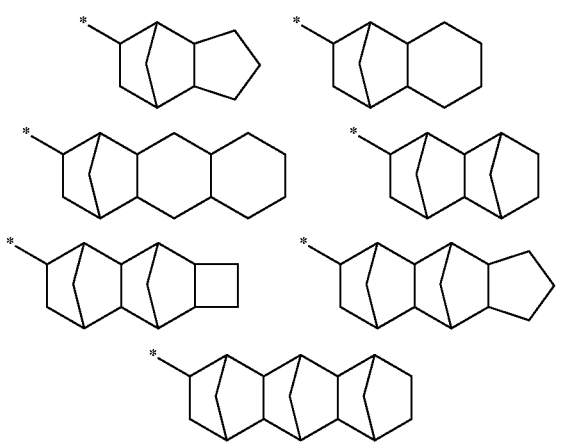

In the formula (a1-1), m1 is preferably an integer of 0 to 3, and is more preferably 0 or 1. In the formula (a1-2), n1 is preferably an integer of 0 to 3, and is more preferably 0 or 1, and n2 is preferably 0, 1 or 2, and more preferably 0 or 1. It is preferred that k1 is an integer of 1 to 4, and it is more preferred that k1 is 1.

Examples of the monomer giving the structural unit represented by the formula (a1-1) include the monomers described in JP2010-204646 A. Among them, preferred are the monomers represented by the formulae (a1-1-1) to (a1-1-8), and more preferred are the monomers represented by the formulae (a1-1-1) to (a1-1-4).

(a1-1-1)

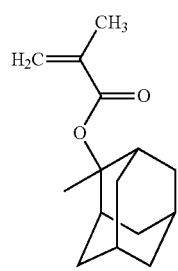

(a1-1-2)

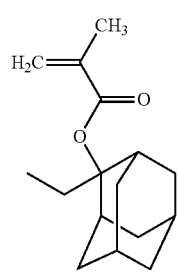

(a1-1-3)

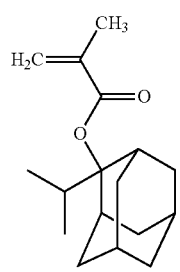

(a1-1-4)

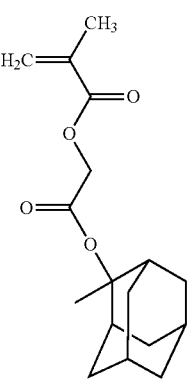

(a1-1-5)

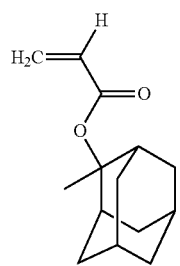

(a1-1-6)

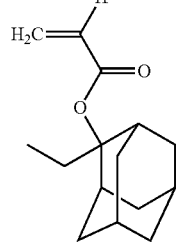

(a1-1-7)

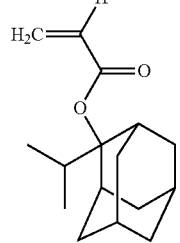

(a1-1-8)

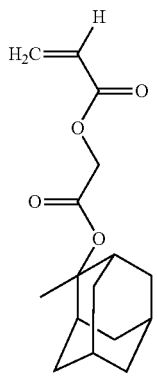

Examples of the monomer giving the structural unit represented by the formula (a1-2) include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate. Among them, preferred are the monomers represented by the formulae (a1-2-1) to (a1-2-6), and more preferred are the monomers represented by the formulae (a1-2-3) and (a1-2-4), and still more preferred is the monomer represented by the formula (a1-2-3).

(a1-2-1)

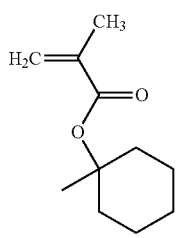

(a1-2-2)

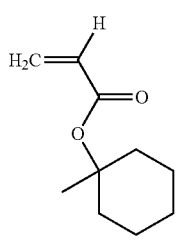

(a1-2-3)

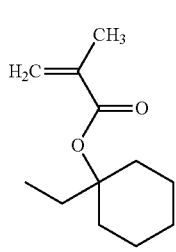

(a1-2-4)

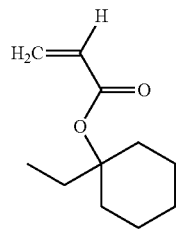

(a1-2-5)

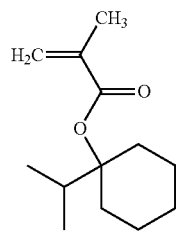

(a1-2-6)

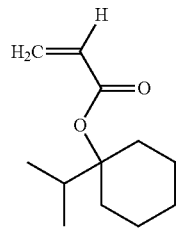

The content of the structural unit represented by the formula (a1-1) or (a1-2) in the resin is usually 10 to 95% by mole, preferably 15 to 90% by mole and more preferably 20 to 85% by mole and especially preferably 20 to 60% by mole based on 100% by mole of all the structural units of the resin.

The content of the structural unit represented by the formula (a1-1) or (a1-2) in the resin can be adjusted by adjusting the amount of the monomer giving the structural unit represented by the formula (a1-1) or (a1-2) based on the total amount of the monomers used for producing the resin. Specifically, the amount of the monomer giving the structural unit represented by the formula (a1-1) or (a1-2) is usually 10 to 95% by mole, preferably 15 to 90% by mole and more preferably 20 to 85% by mole and especially preferably 20 to 60% by mole based on 100% by mole of all the monomers used for producing the resin.

The content of the structural unit having an adamantyl group, especially the structural unit represented by the formula (a1-1) is preferably 15% by mole or more based on 100% by mole of all the structural units of the resin from the viewpoint of dry-etching resistance of the photoresist composition.

Other examples of the monomer having an acid-labile group include a monomer represented by the formula (a1-3):

(a1-3)

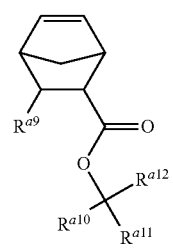

wherein $R^{a9}$ represents a hydrogen atom, a C1-C3 alkyl group which can have one or more hydroxyl groups, a carboxyl group, a cyano group or a —COOR$^{a13}$ group in which $R^{a13}$ represents a C1-C8 alkyl group or a C3-C20 alicyclic hydrocarbon group, and a group composed of a C1-C8 alkyl group and a C3-C20 alicyclic hydrocarbon group, and the alkyl group and the alicyclic hydrocarbon group can have one or more hydroxyl groups, and one or more —CH$_2$— in the alkyl group and the alicyclic hydrocarbon group can be replaced by —O— or —CO—, $R^{a10}$, $R^{a11}$ and $R^{a12}$ each independently represent a C1-C12 alkyl group or a C3-C20 alicyclic hydrocarbon group, and $R^{a10}$ and Rall can be bonded each other to form a C3-C20 ring together with the carbon atom to which $R^{a10}$ and $R^{a11}$ are bonded, and the alkyl group and the alicyclic hydrocarbon group can have one or more hydroxyl groups, and one or more —CH$_2$— in alkyl group and the alicyclic hydrocarbon group can be replaced by —O— or —CO—.

Examples of the C1-C3 alkyl group which can have one or more hydroxyl groups include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the C3-C20 ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

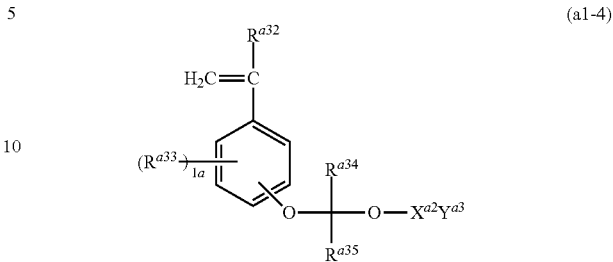

(a1-4)

wherein $R^{a32}$ represents a hydrogen atom, a halogen atom, a C1-C6 alkyl group or a C1-C6 halogenated alkyl group, $R^{a33}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{a34}$ and $R^{a35}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C18 hydrocarbon group, and the C1-C17 divalent saturated hydrocarbon group and the C1-C18 hydrocarbon group can have one or more substituents selected from the group consisting of a halogen atom, a hydroxyl group, a C1-C6 alkyl group, a C1-C6 alkoxy group, a C2-C4 acyl group and a C2-C4 acyloxy group.

Examples of the halogen atom include a fluorine atom, a chlorine atom, a bromine atom and an iodine atom.

Examples of the C1-C6 alkyl group include the same as described above, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the hydrocarbon group include the chain aliphatic hydrocarbon group described above, the alicyclic hydrocarbon group described above, and the groups formed by combining these groups such as 2-alkyl-2-adamantyl group and 1-(1-adamantyl)-1-alkyl group, and the aromatic hydrocarbon group.

Preferable examples of the hydrocarbon group represented by $R^{a34}$ and $R^{a35}$ include an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group.

Preferable examples of the substituents in the C1-C17 divalent saturated hydrocarbon group and the C1-C18 hydrocarbon group is a hydroxyl group.

Examples of the C1-C17 divalent aliphatic hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the monomer represented by the formula (a1-4) include the following.

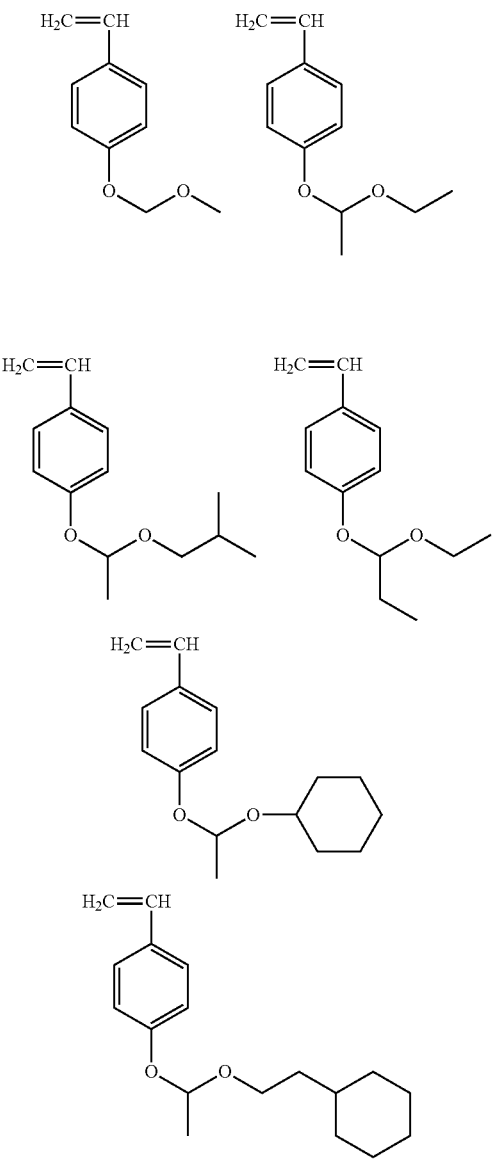

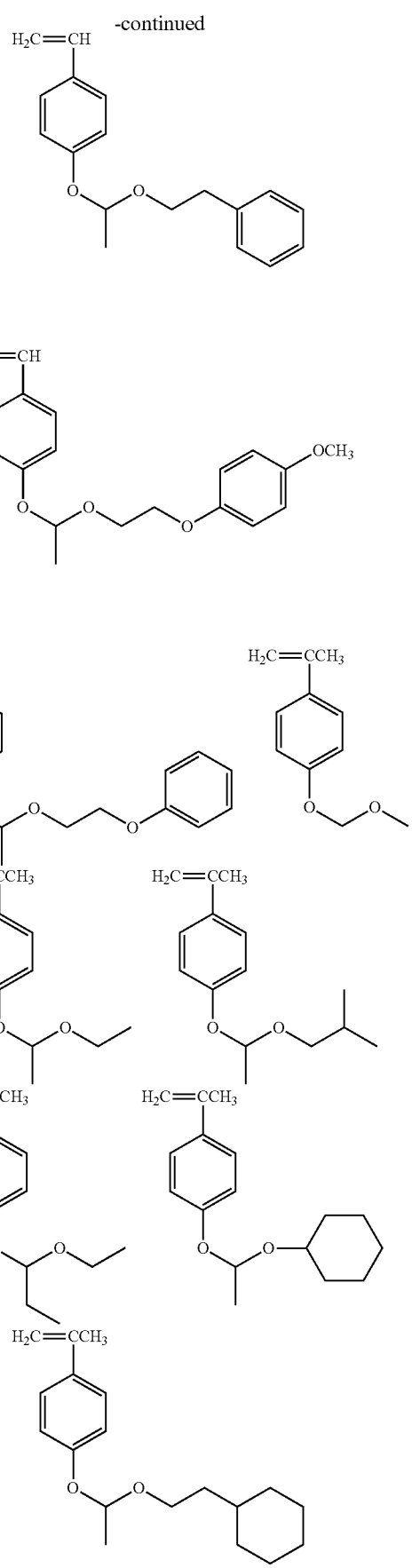

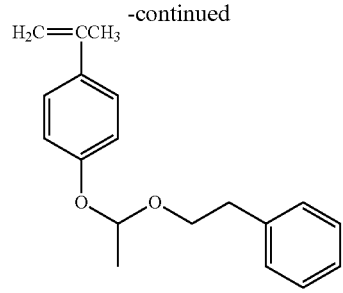
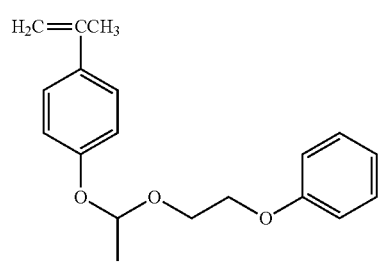
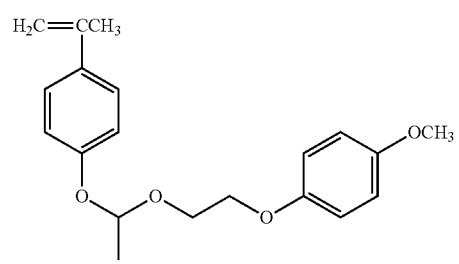
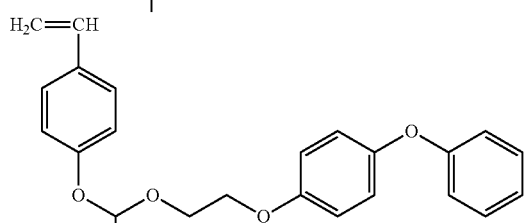
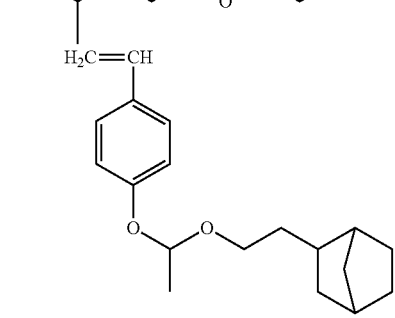
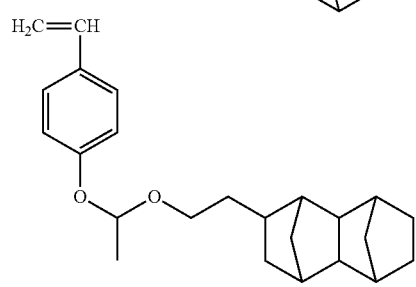
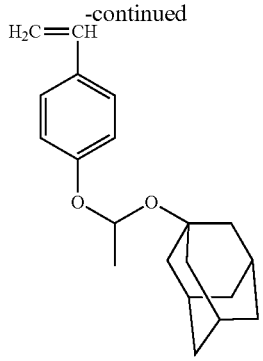
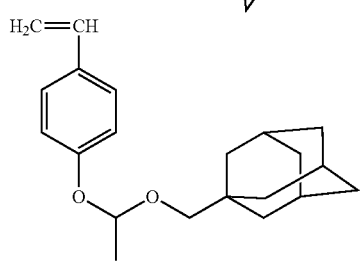
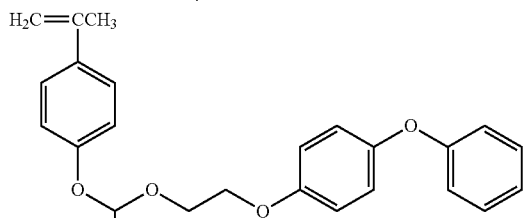
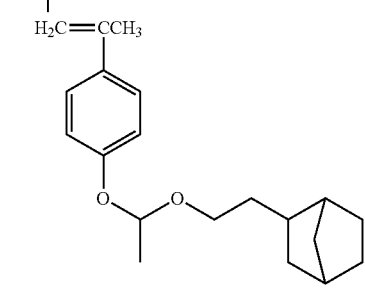
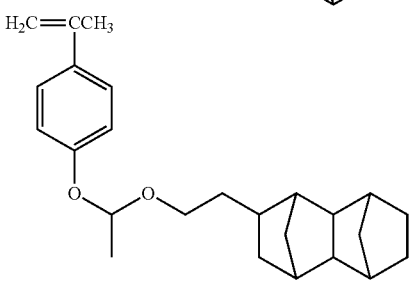
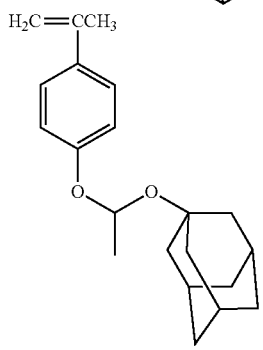

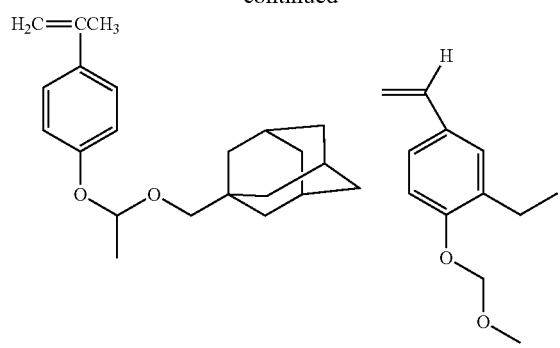
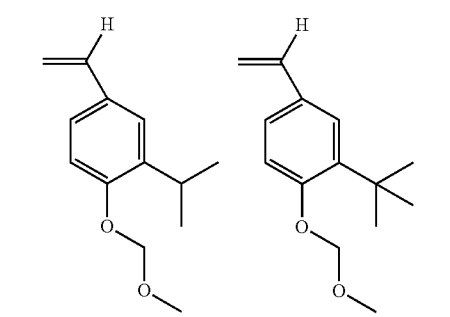
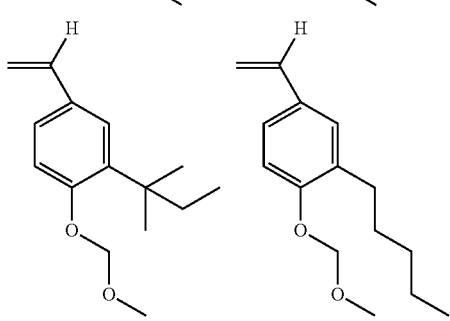
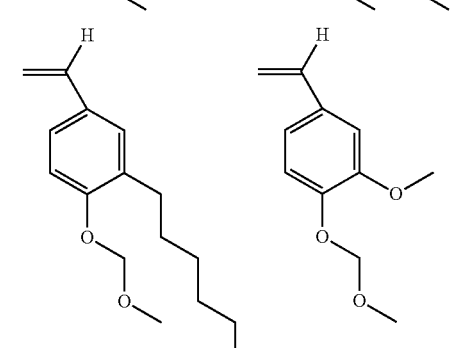
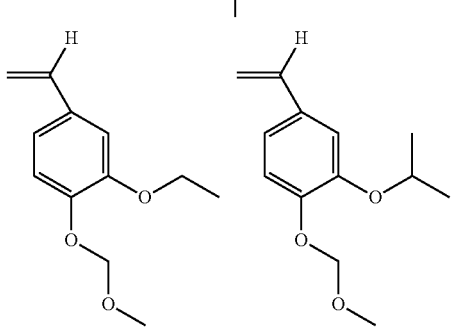
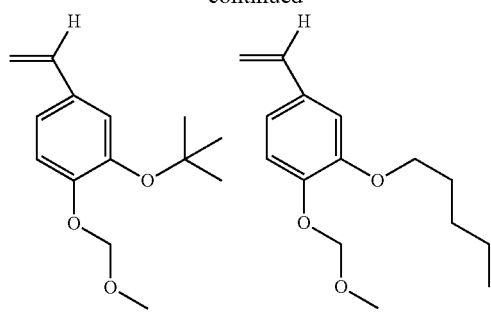

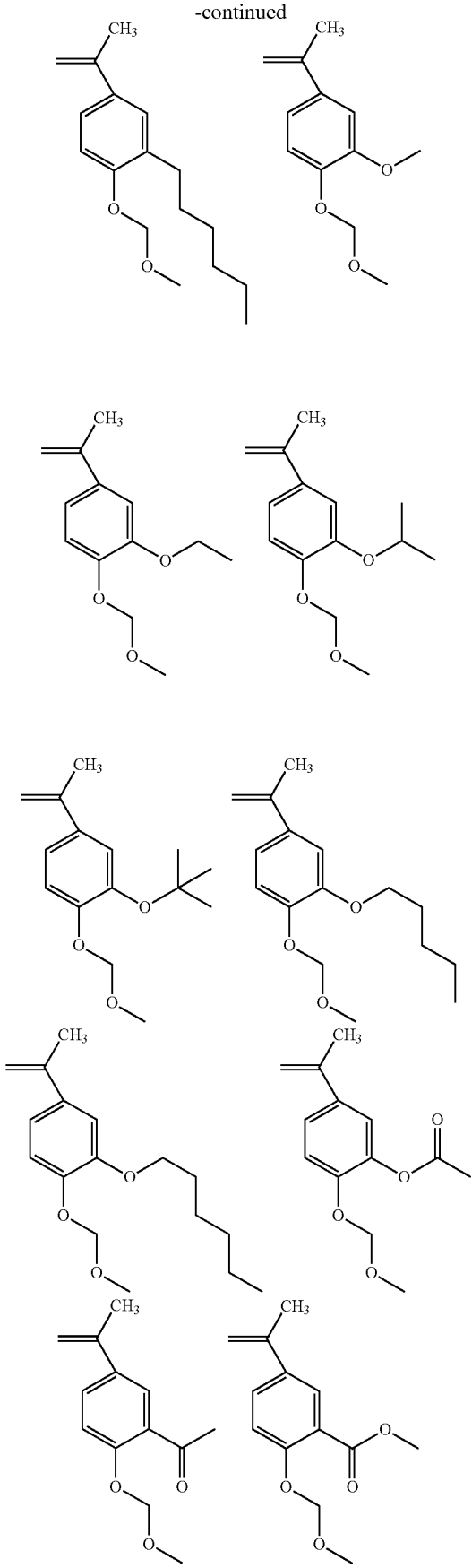

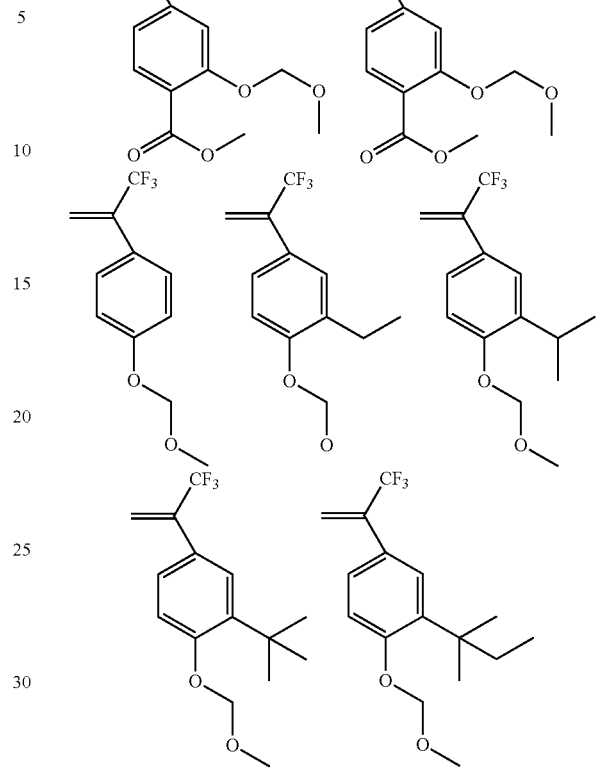

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

Other examples of the monomer having an acid-labile group include a monomer represented by the formula (a1-5):

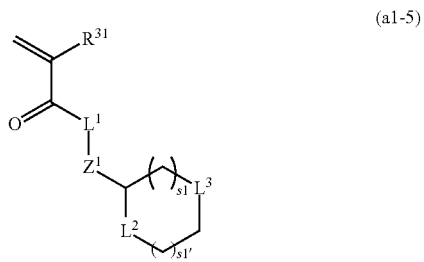

(a1-5)

wherein $R^{31}$ represents a hydrogen atom, a halogen atom, a C1-C6 alkyl group which may be substituted with a halogen atom, $L^1$ represents —O—, —S— or *—O— $(CH_2)_{k1}$— CO—O—, k1 represents an integer of 1 to 7, * represents a binding position to —CO—, $L^2$ and $L^3$ independently each represent —O— or —S—, $Z^1$ represents a single bond or a C1-C6 alkanediyl group in which one or more —$CH_2$— may be replaced by —O— or —CO—, s1 and s1' independently each represent an integer of 0 to 4.

Examples of the halogen atom include a fluorine atom, a chlorine atom and a bromine atom.

Examples of the C1-C6 alkyl group which may be substituted with a halogen atom include a methyl group, an ethyl group, a propyl group, an isopropyl group, a butyl group, an isobutyl group, a sec-butyl group, a tert-butyl group, a pentyl group, a hexyl group, a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group, and a C1-C4 alkyl group is preferable and a C1-C2 alkyl group is more preferable and a methyl group is especially preferable.

$R^{31}$ is preferably a hydrogen atom or a methyl group.

$L^1$ is preferably —O—.

It is preferred that one of $L^2$ and $L^3$ is —O— and the other is —S—.

In the formula (a1-5), s1 is preferably 1 and s1 is preferably 0, 1 or 2.

$Z^1$ is preferably a single bond, *—$(CH_2)_{n4}$—O— or *—$(CH_2)_{n4}$—CO—O— in which n4 represents an integer of 1 to 4, and * represents a binding position to $L^4$, and more preferably a single bond, —$CH_2$—O— or —$CH_2$—CO—O—.

Examples of the monomer represented by the formula (a1-5) include the following.

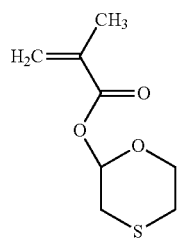

(a1-5-1)

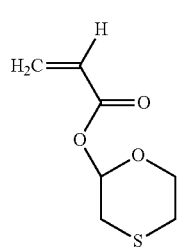

(a1-5-2)

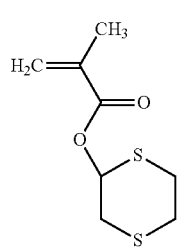

(a1-5-3)

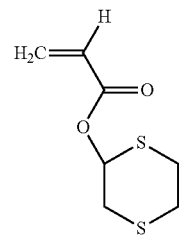

(a1-5-4)

When the resin contains the structural unit derived form the monomer represented by the formula (a1-5), the content of the structural unit derived from the monomer represented by the formula (a1-5) is usually 1 to 95% by mole and preferably 3 to 90% by mole and more preferably 5 to 85% by mole based on total molar of all the structural units of the resin.

The resin can have two or more kinds of structural units derived from the monomers having an acid-labile group.

The resin preferably contains the structural unit derived from the monomer having an acid-labile group and a structural unit derived from the monomer having no acid-labile group. The resin can have two or more kinds of structural units derived from the monomers having no acid-labile group. When the resin contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of the resin.

The monomer having no acid-labile group preferably contains one or more hydroxyl groups or a lactone ring. When the resin contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

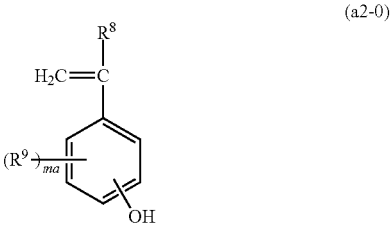

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

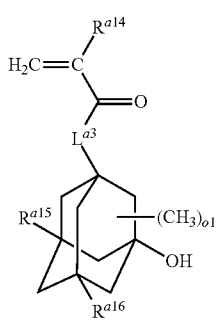
(a2-1)

wherein $R^{a14}$ represents a hydrogen atom or a methyl group, $R^{a11}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with a base.

Examples of the monomer represented by the formula (a2-0) include the monomers described in JP 2010-204646 A, and the monomers represented by the formulae (a2-0-1) and (a2-0-2):

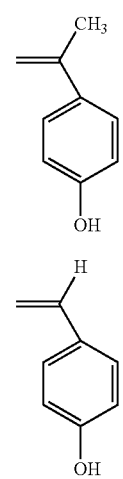
(a2-0-1)

(a2-0-2)

are preferable.

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and of is preferably 0, 1, 2 or 3 and is more preferably 0 or 1.

Examples of the monomer represented by the formula (a2-1) include the monomers described in JP 2010-204646 A, and the monomers represented by the formulae (a2-1-1) to (a2-1-6) are preferable, and the monomers represented by the formulae (a2-1-1) to (a2-1-4) are more preferable, and the monomers represented by the formulae (a2-1-1) and (a2-1-3) are still more preferable,

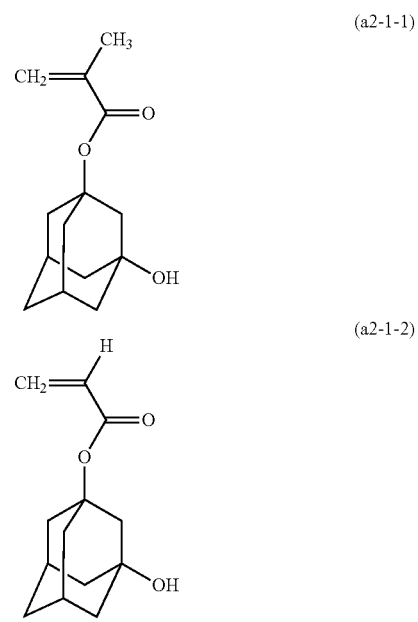
(a2-1-1)

(a2-1-2)

(a2-1-3)
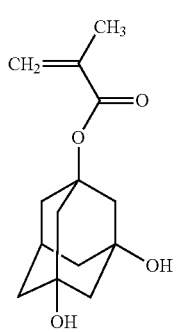

(a2-1-4)
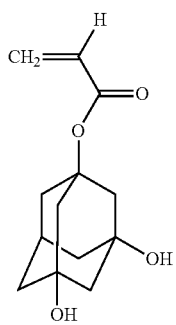

(a2-1-5)
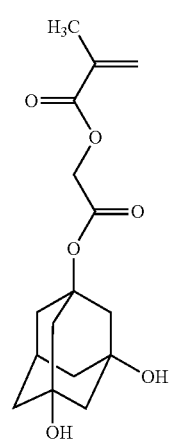

(a2-1-6)
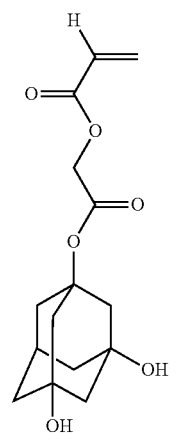

When the resin contains the structural unit derived from the monomer represented by the formula (a2-1), the content of the structural unit derived from the monomer represented by the formula (a2-1) is usually 3 to 45% by mole based on total molar of all the structural units of the resin, and preferably 5 to 40% by mole, and more preferably 5 to 35% by mole, and especially preferably 5 to 20% by mole.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

(a3-1)
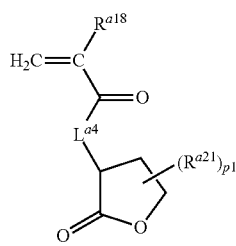

(a3-2)
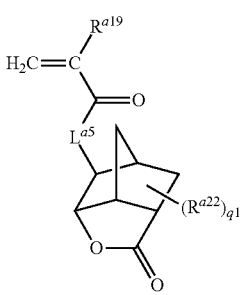

(a3-3)
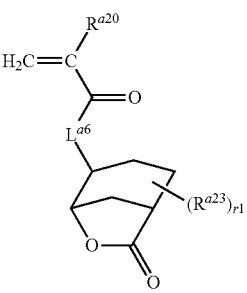

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 alkyl group, $R^{a22}$ and $R^{a23}$ are independently in each occurrence a carboxyl group, a cyano group or a C1-C4 alkyl group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the monomers described in JP 2010-204646 A, and the monomers represented by the formulae (a3-1-1) to (a3-1-4), (a3-2-1) to (a3-2-4) and (a3-3-1) to (a3-3-4) are preferable, and the monomers represented by the formulae (a3-1-1) to (a3-1-2) and (a3-2-3) to (a3-2-4) are more preferable, and the monomers represented by the formulae (a3-1-1) and (a3-2-3) are still more preferable.

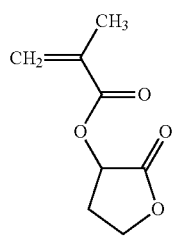
(a3-1-1)

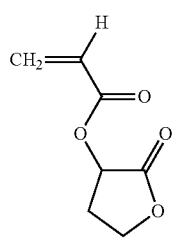
(a3-1-2)

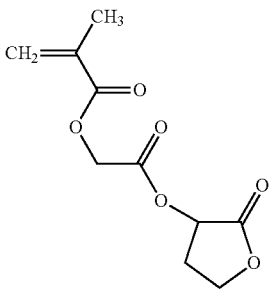
(a3-1-3)

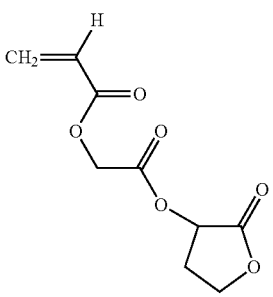
(a3-1-4)

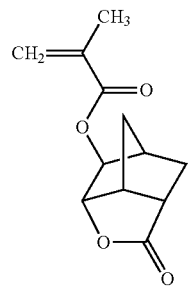
(a3-2-1)

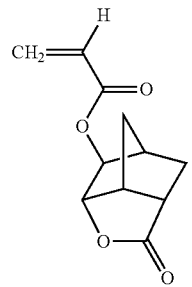
(a3-2-2)

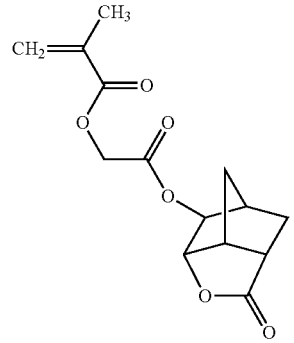
(a3-2-3)

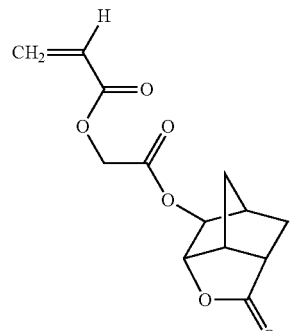
(a3-2-4)

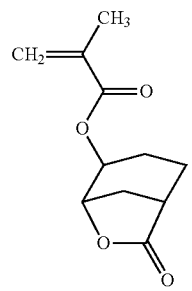
(a3-3-1)

(a3-3-2)

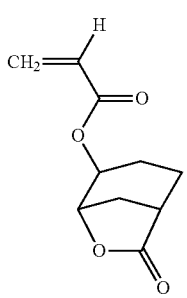

(a3-3-3)

(a3-3-4)

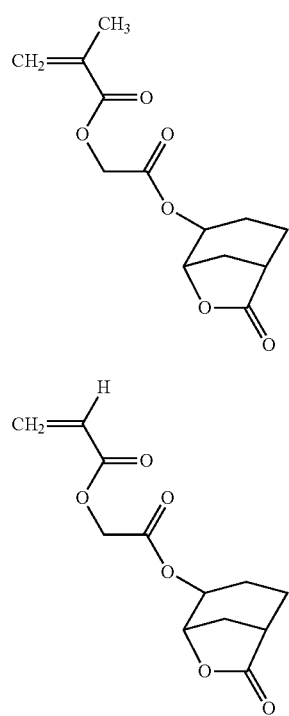

When the resin contains the structural unit derived from the monomer having no acid-labile group and having a lactone ring, the content thereof is usually 5 to 70% by mole based on total molar of all the structural units of the resin, and preferably 10 to 65% by mole and more preferably 10 to 60% by mole.

When the resin contains the structural unit derived from the monomer represented by the formula (a3-1), (a3-2) or (a3-3), the content thereof is usually 5 to 60% by mole based on total molar of all the structural units of the resin, and preferably 5 to 50% by mole and more preferably 10 to 50% by mole.

Examples of the other monomer having no acid-labile group include the monomers represented by the formulae (a4-1), (a4-2) and (a4-3):

(a4-1)

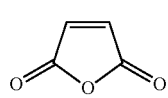

(a4-2)

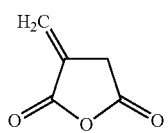

(a4-3)

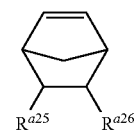

wherein $R^{a25}$ and $R^{a26}$ each independently represents a hydrogen atom, a C1-C3 alkyl group which can have one or more hydroxyl groups, a carboxyl group, a cyano group or a —COOR$^{a27}$ group in which $R^{a27}$ represents a C1-C18 alkyl group or a C3-C20 alicyclic hydrocarbon group, and one or more —CH$_2$— in the C1-C18 alkyl group and the C3-C20 alicyclic hydrocarbon group can be replaced by —O— or —CO—, with the proviso that the carbon atom bonded to —O— of —COO— of $R^{a27}$ is not a tertiary carbon atom, or $R^{a25}$ and $R^{a26}$ are bonded together to form a carboxylic anhydride residue represented by —C(=O)—O—C(=O)—.

Examples of the C1-C3 alkyl group which can have one or more hydroxyl groups include a methyl group, an ethyl group, a propyl group, a hydroxymethyl group and a 2-hydroxyethyl group. The C1-C18 alkyl group represented by $R^{a27}$ is preferably a C1-C8 alkyl group and is more preferably a C1-C6 alkyl group. The C3-C20 alicyclic hydrocarbon group represented by $R^{a27}$ is preferably a C4-C18 alicyclic hydrocarbon group, and is more preferably C4-C12 alicyclic hydrocarbon group. Examples of $R^{a27}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of the resin.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, preferably 3,000 or more of the weight-average molecular weight, and more preferably 4,000 or more of the weight-average molecular weight. The resin usually has 50,000 or less of the weight-average molecular weight, preferably has 30,000 or less of the weight-average molecular weight, and more preferably 15,000 or less of the weight-average molecular weight. The weight-average molecular weight can be measured with gel permeation chromatography.

The content of the resin in the photoresist composition of the present invention is usually 80% by mass or more based on sum of solid component, and usually 99% by mass or less. In this specification, "solid component" means components other than solvent in the photoresist composition.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

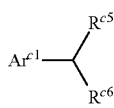
(C2)

wherein $Ar^{c1}$ represents an aromatic hydrocarbon group, and $R^{c5}$ and $R^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

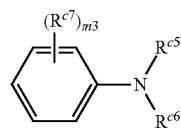
(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydro- carbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

(C3)

(C4)

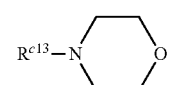
(C5)

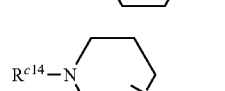
(C6)

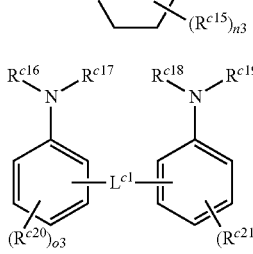
(C7)

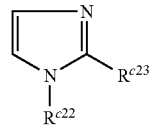
(C8)

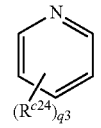
(C9)

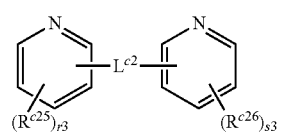
(C10)

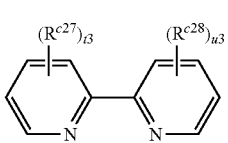

(C11)

wherein $R^{c8}$, $R^{c20}$, $R^{c21}$, and $R^{c23}$ to $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline.

Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 1% by mass based on sum of solid component.

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by mass or more, preferably 92% by mass or more preferably 94% by mass or more based on total amount of the photoresist composition of the present invention. The amount of the solvent is usually 99.9% by mass or less and preferably 99% by mass or less based on total amount of the photoresist composition of the present invention.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention are useful for a chemically amplified photoresist composition.

A photoresist pattern can be produced by the following steps (1) to (5):

(1) a step of applying the first or second photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having a pore size of 0.003 to 0.2 μm before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a mass basis unless otherwise specifically noted. The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 µL] using standard polystyrene as a standard reference material. Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Example 1

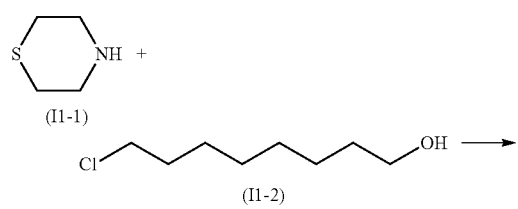

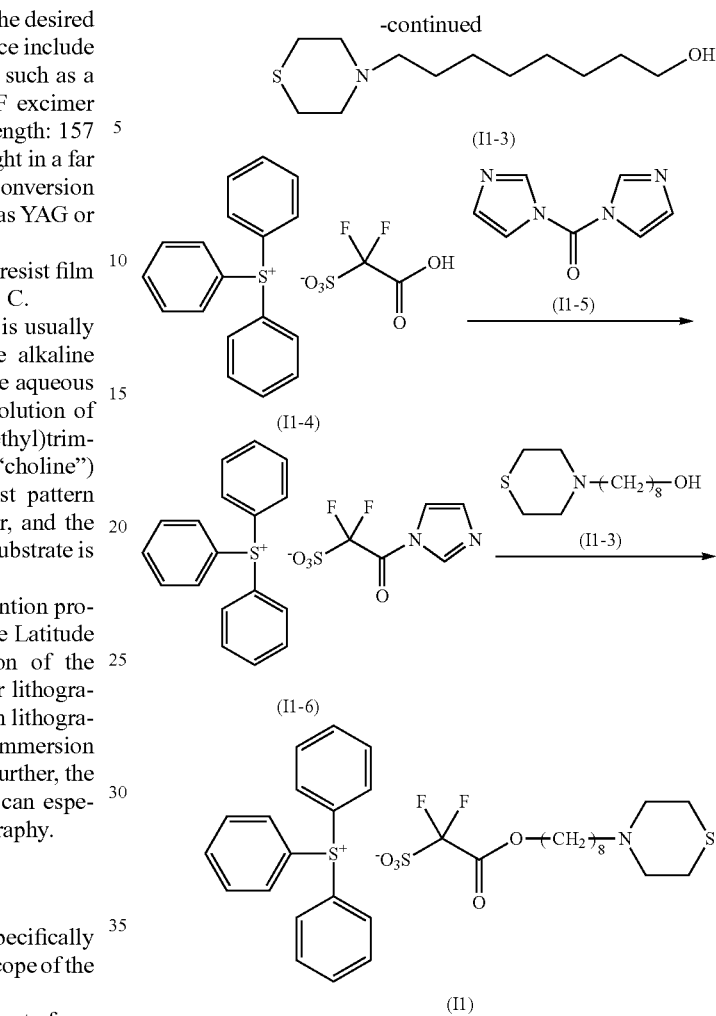

Five (5) parts of the compound represented by the formula (I1-2), 25.00 parts of methyl isobutyl ketone and 1.37 parts of N-methylpyrrolidine were mixed, and the resultant mixture was stirred at 23° C. for 30 minutes. To the mixture, 6.27 parts of the compound represented by the formula (I1-1) was added dropwise over 30 minutes. The mixture obtained was heated at 100° C. for 20 hours. The reaction mixture obtained was mixed with 12.50 parts of ion-exchanged water, and the resultant mixture was stirred and separated to obtain an organic layer. This washing was repeated five times. The organic layer obtained was mixed with 0.26 part of activated carbon, and the resultant mixture was stirred at 23° C. for 30 minutes followed by filtration. The filtrate obtained was concentrated to obtain 3.74 parts of the compound represented by the formula (I1-3).

The compound represented by the formula (I1-4) was prepared according to the method described in JP 2008-127367 A.

Five (5) parts of the salt represented by the formula (I1-4) and 25.10 parts of chloroform were mixed, and the resultant mixture was stirred at 23° C. for 30 minutes. To the mixture, 2.21 parts of the compound represented by the formula (I1-5) was added, and the mixture obtained was stirred at 60° C. for 1 hour. The reaction mixture obtained was cooled down to 23° C., and filtrated to obtain a solution containing the compound represented by the formula (I1-6). To the solution obtained, 3.54 parts of the compound represented by the formula (I1-3)

and 3.54 parts of chloroform were added, and the resultant mixture was stirred at 23° C. for 12 hours. The reaction mixture obtained was mixed with 12.55 parts of ion-exchanged water, and then the resultant mixture was stirred and separated to obtain an organic layer. This washing was repeated five times. The organic layer obtained was mixed with 0.59 part of activated carbon, and the resultant mixture was stirred at 23° C. for 30 minutes followed by filtration. The filtrate obtained was concentrated. The concentrate obtained was mixed with 52.30 parts of tert-butyl methyl ether followed by stirring. After removing a supernatant, the residue obtained was dissolved in acetonitrile. The solution obtained was concentrated to obtain 2.82 parts of the salt represented by the formula (II). This is called as Salt I1.

MS (ESI(+) Spectrum): M$^+$ 263.1
MS (ESI(−) Spectrum): M$^-$ 388.1

Example 2

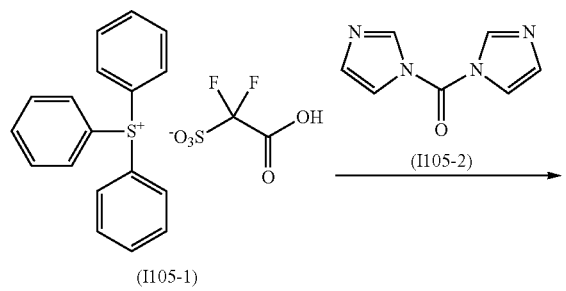

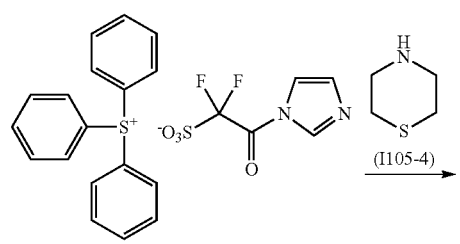

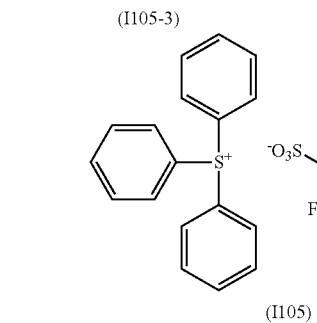

The compound represented by the formula (I105-1) was prepared according to the method described in JP 2008-127367 A.

Four point nine eight (4.98) parts of the salt represented by the formula (I105-1) and 25 parts of chloroform were mixed, and the resultant mixture was stirred at 23° C. for 30 minutes.

To the mixture, 2.20 parts of the compound represented by the formula (I105-2) was added, and the mixture obtained was stirred at 70° C. for 2 hours. The reaction mixture obtained was cooled down to 23° C., and filtrated to obtain a solution containing the compound represented by the formula (I105-3). To the solution obtained, 1.17 parts of the compound represented by the formula (I105-4) was added, and the resultant mixture was stirred at 23° C. for 12 hours. The reaction mixture obtained was concentrated, and then, the residue obtained was mixed with 40 parts of chloroform and 13.33 parts of ion-exchanged water. The resultant mixture was stirred and separated to obtain an organic layer. This washing was repeated five times. The organic layer obtained was mixed with 0.50 part of activated carbon, and the resultant mixture was stirred at 23° C. for 30 minutes followed by filtration. The filtrate obtained was concentrated. The concentrate obtained was mixed with 34.80 parts of tert-butyl methyl ether followed by stirring. The mixture obtained was filtrated to obtain 4.13 parts of the salt represented by the formula (I105). This is called as Salt I105.

MS (ESI(+) Spectrum): M$^+$ 263.1
MS (ESI(−) Spectrum): M$^-$ 260.0

Example 3

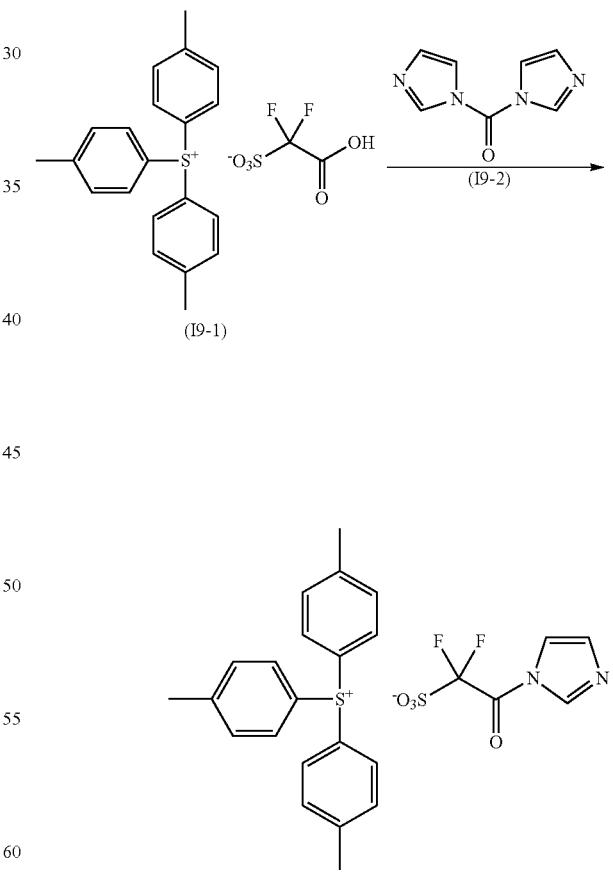

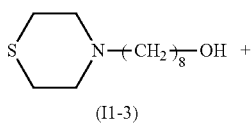

-continued

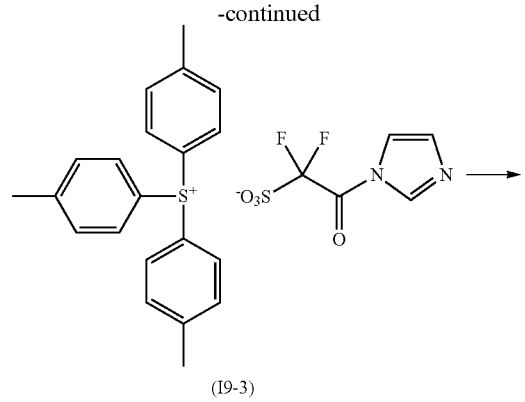

(I9-3)

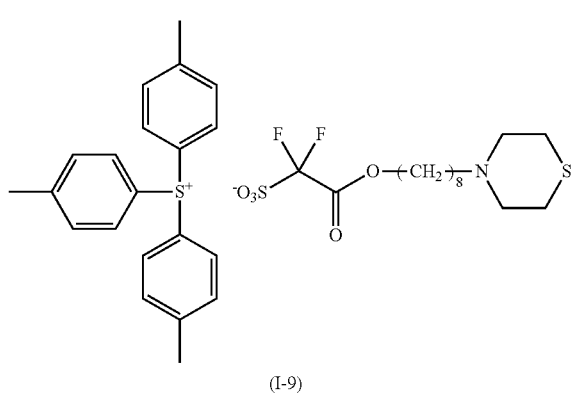

(I-9)

Three point two eight (3.28) parts of the salt represented by the formula (I9-1) and 15 parts of acetonitrile were mixed, and the resultant mixture was stirred at 23° C. for 30 minutes. To the mixture, 1.30 parts of the compound represented by the formula (I9-2) was added, and the mixture obtained was stirred at 70° C. for 2 hours. The reaction mixture obtained was cooled down to 23° C., and filtrated to obtain a solution containing the compound represented by the formula (I9-3). To the solution obtained, a solution prepared by dissolving 1.36 parts of the compound represented by the formula (I1-3) in 4.08 parts of chloroform was added, and the resultant mixture was stirred at 23° C. for 23 hours. The reaction mixture obtained was concentrated, and then, the residue obtained was mixed with 60 parts of chloroform and 30 parts of 2% aqueous oxalic acid solution. The resultant mixture was stirred and separated to obtain an organic layer. This washing was repeated twice. The organic layer obtained was washed five times with 30 parts of ion-exchanged water. The organic layer obtained was concentrated, and the residue obtained was dissolved in 30 parts of acetonitrile. The solution obtained was concentrated, and the residue obtained was mixed with 50 parts of tert-butyl methyl ether, and the resultant mixture was stirred. The supernatant was removed. The residue obtained was dissolved in acetonitrile, and the solution obtained was concentrated to obtain 1.63 parts of the salt represented by the formula (I-9). This is called as Salt 19.

MS (ESI(+) Spectrum): M⁺ 305.1
MS (ESI(−) Spectrum): M⁻ 388.1

Example 4

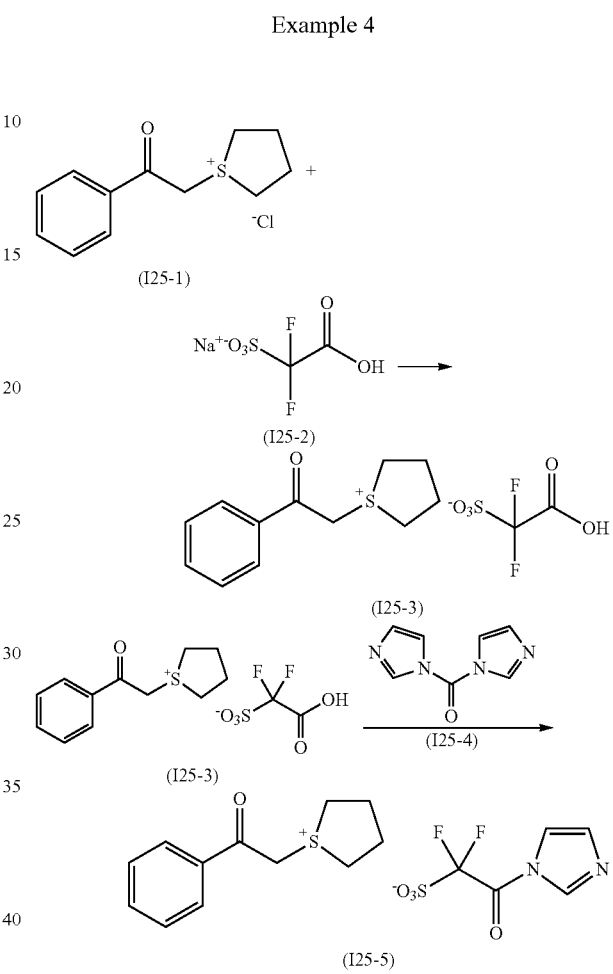

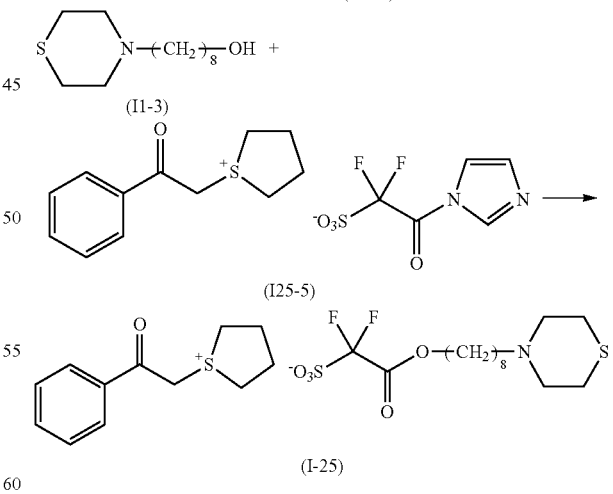

(I-25)

Ten point nine five (10.95) parts of the salt represented by the formula (I25-1), 8.96 parts of the salt represented by the formula (I25-2), 100 parts of acetonitrile and 50 parts of ion-exchanged water were mixed. The resultant mixture was stirred at 23° C. for 15 hours. The mixture obtained was concentrated followed by extracting with 100 parts of chloroform. The organic layer obtained was concentrated to obtain 14.63 parts of the salt represented by the formula (I25-3).

Two point six one (2.61) parts of the salt represented by the formula (I25-3) and 15 parts of acetonitrile were mixed, and the resultant mixture was stirred at 23° C. for 30 minutes. To the mixture, 1.30 parts of the compound represented by the formula (I25-4) was added, and the mixture obtained was stirred at 70° C. for 2 hours. The reaction mixture obtained was cooled down to 23° C., and filtrated to obtain a solution containing the compound represented by the formula (I25-5). To the solution obtained, a solution prepared by dissolving 1.36 parts of the compound represented by the formula (I1-3) in 4.08 parts of chloroform was added, and the resultant mixture was stirred at 23° C. for 23 hours. The reaction mixture obtained was concentrated, and then, the residue obtained was mixed with 60 parts of chloroform and 30 parts of 2% aqueous oxalic acid solution. The resultant mixture was stirred and separated to obtain an organic layer. This washing was repeated twice. The organic layer obtained was washed five times with 30 parts of ion-exchanged water. The organic layer obtained was concentrated, and the residue obtained was dissolved in 30 parts of acetonitrile. The solution obtained was concentrated, and the residue obtained was mixed with 50 parts of tert-butyl methyl ether, and the resultant mixture was stirred. The supernatant was removed. The residue obtained was dissolved in acetonitrile, and the solution obtained was concentrated to obtain 1.21 parts of the salt represented by the formula (I-25). This is called as Salt 125.

MS (ESI(+) Spectrum): M$^+$ 207.1

MS (ESI(−) Spectrum): M$^-$ 388.1

Example 5

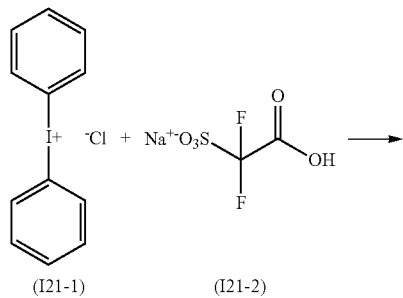

(I21-1)    (I21-2)

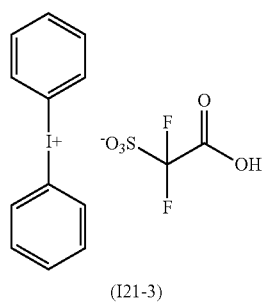

(I21-3)

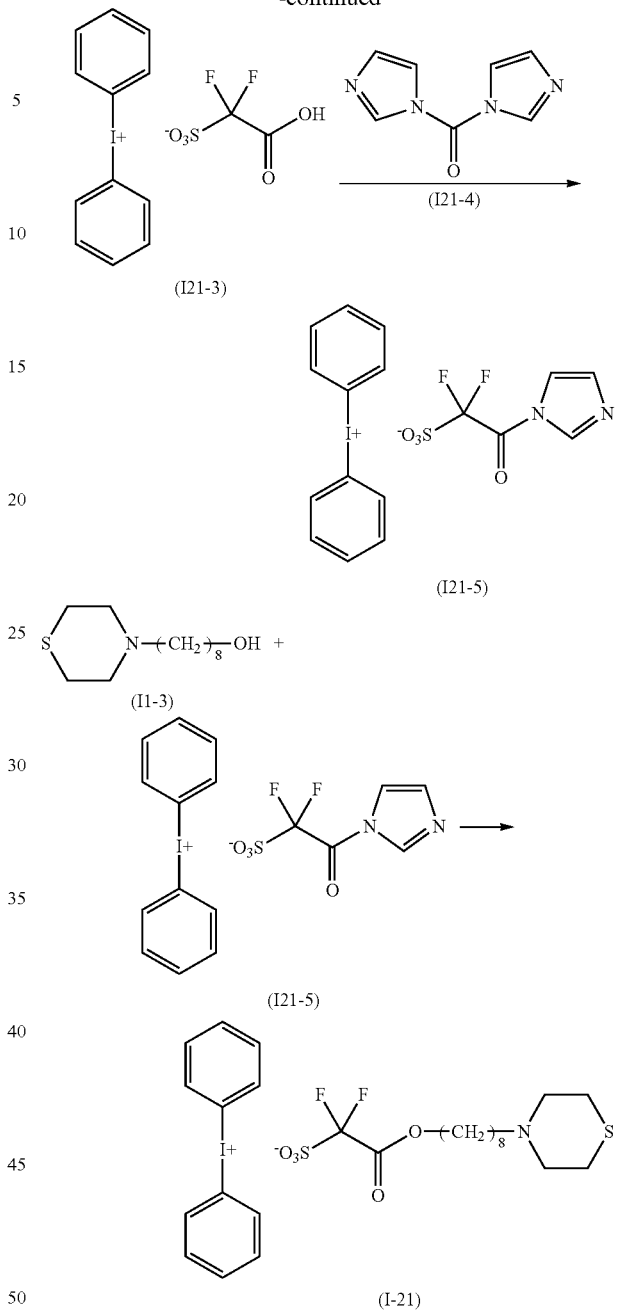

Fourteen point two eight (14.28) parts of the salt represented by the formula (I21-1), 8.96 parts of the salt represented by the formula (I21-2), 100 parts of acetonitrile and 50 parts of ion-exchanged water were mixed. The resultant mixture was stirred at 23° C. for 15 hours. The mixture obtained was concentrated followed by extracting with 100 parts of chloroform. The organic layer obtained was concentrated to obtain 19.30 parts of the salt represented by the formula (I21-3).

Three point one one (3.11) parts of the salt represented by the formula (I21-3) and 15 parts of acetonitrile were mixed, and the resultant mixture was stirred at 23° C. for 30 minutes. To the mixture, 1.30 parts of the compound represented by the formula (I21-4) was added, and the mixture obtained was stirred at 70° C. for 2 hours. The reaction mixture obtained was cooled down to 23° C., and filtrated to obtain a solution containing the compound represented by the formula (I21-5). To the solution obtained, a solution prepared by dissolving 1.36 parts of the compound represented by the formula (I1-3) in 4.08 parts of chloroform was added, and the resultant mixture was stirred at 23° C. for 23 hours. The reaction mixture obtained was concentrated, and then, the residue obtained was mixed with 60 parts of chloroform and 30 parts of 2% aqueous oxalic acid solution. The resultant mixture was stirred and separated to obtain an organic layer. This washing was repeated twice. The organic layer obtained was washed five times with 30 parts of ion-exchanged water. The organic layer obtained was concentrated, and the residue obtained was dissolved in 30 parts of acetonitrile. The solution obtained was concentrated, and the residue obtained was mixed with 50 parts of tert-butyl methyl ether, and the resultant mixture was stirred. The supernatant was removed. The residue obtained was dissolved in acetonitrile, and the solution obtained was concentrated to obtain 1.92 parts of the salt represented by the formula (I-21). This is called as Salt I21.

MS (ESI(+) Spectrum): M⁺ 281.0

MS (ESI(−) Spectrum): M⁻ 388.1

Monomers used in the following Resin Synthesis Examples 1 to 2 are following monomers (A), (B), (C), (D), (E), (F) and (G).

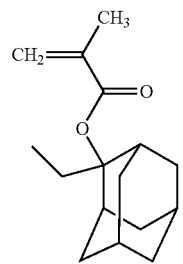

(A)

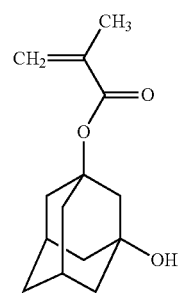

(B)

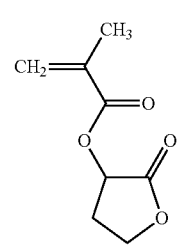

(C)

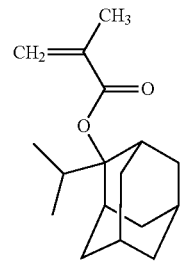

(D)

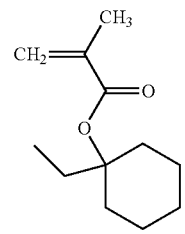

(E)

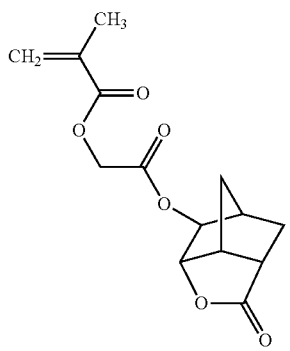

(F)

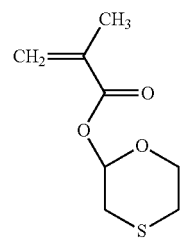

(G)

Resin Synthesis Example 1

The monomers (D), (E), (B), (C) and (F) were mixed in a molar ratio of 30/14/6/20/30 (monomer (D)/monomer (E)/monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (mass ratio (methanol/water)=4/1) to cause precipitation. The precipitate was collected by filtration and then, was dissolved followed by poured the resultant solution into a large amount of a mixture of methanol and water to cause precipitation. This operation was repeated twice for purification. As a result, a resin having a weight-average molecular weight of about 8.1×10³ was obtained in a yield of 65%. This resin is called as resin A1. Resin A1 had the following structural units.

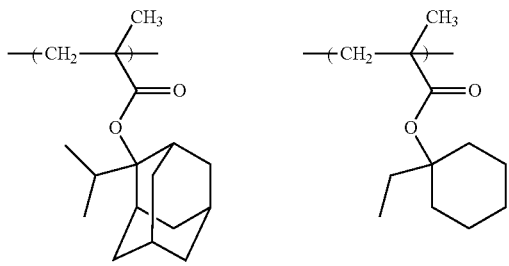
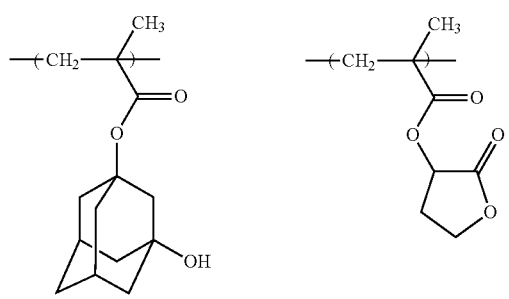
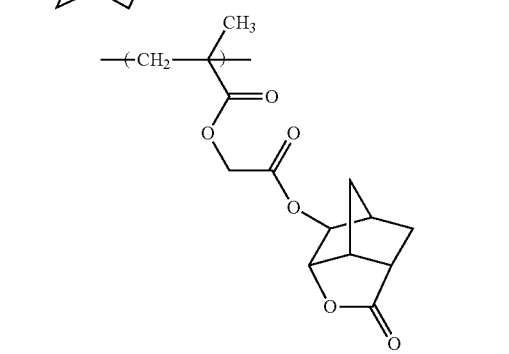

Resin Synthesis Example 2

The monomers (A), (E), (B), (C) and (F) were mixed in a molar ratio of 30/14/6/20/30 (monomer (A)/monomer(E)/ monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (mass ratio (methanol/water)=4/1) to cause precipitation. The precipitate was collected by filtration and then, was dissolved followed by poured the resultant solution into a large amount of a mixture of methanol and water to cause precipitation. This operation was repeated three times for purification. As a result, a resin having a weight-average molecular weight of about 7.8×10³ was obtained in a yield of 68%. This resin is called as resin A2. Resin A2 had the following structural units.

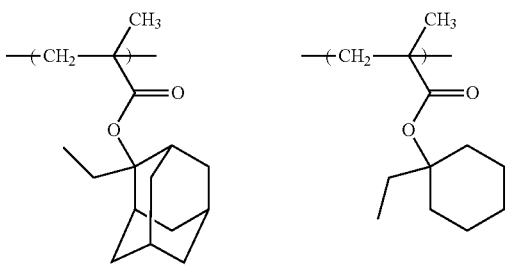
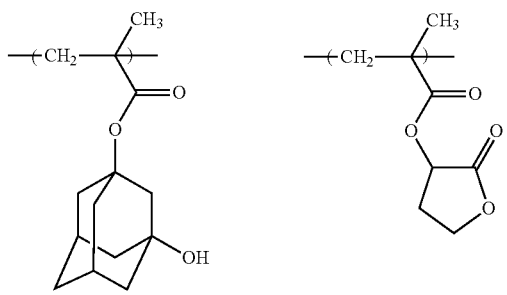
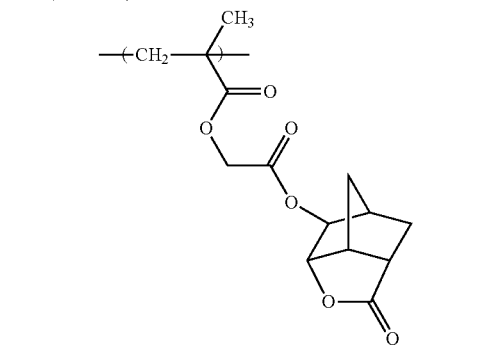

Resin Synthesis Example 3

The monomers (A), (B) and (C) were mixed in a molar ratio of 50/25/25 (monomer (A)/monomer (B)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 80° C. for about 8 hours. The reaction mixture obtained was poured into a large amount of a mixture of methanol and water (mass ratio (methanol/water)=4/1) to cause precipitation. The precipitate was collected by filtration and then, was dissolved followed by poured the resultant solution into a large amount of a mixture of methanol and water to cause precipitation.

This operation was repeated three times for purification. As a result, a resin having a weight-average molecular weight of about 9.2×10³ was obtained in a yield of 60%. This resin is called as resin A3. Resin A3 had the following structural units.

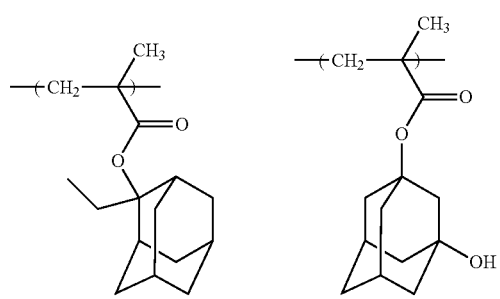
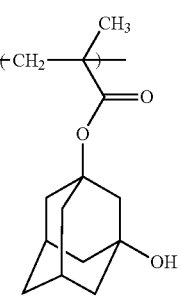
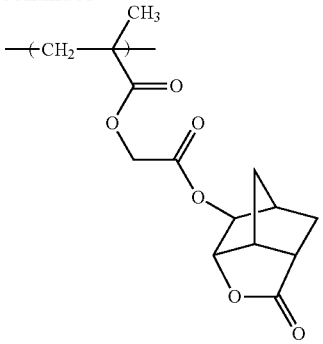

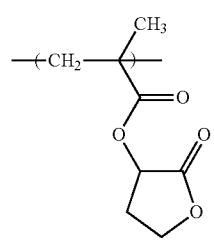
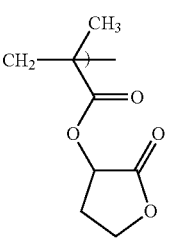

Resin Synthesis Example 4

The monomers (A), (E), (B), (F) and (C) were mixed in a molar ratio of 30/14/6/20/30 (monomer (A)/monomer (E)/monomer (B)/monomer (F)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis (2,4-dimethylvaleronitrile) as an initiator in a ratio of 3 mol % based on all monomer molar amount were added, and the obtained mixture was heated at 75° C. for about 5 hours. The reaction mixture obtained was poured into a large amount of a mixture of methanol and water to cause precipitation. The precipitate was collected by filtration and then, was dissolved followed by poured the resultant solution into a large amount of a mixture of methanol and water to cause precipitation. This operation was repeated twice for purification. As a result, a resin having a weight-average molecular weight of about $7.2 \times 10^3$ was obtained in a yield of 78%. This resin is called as resin A4. Resin A4 had the following structural units.

Resin Synthesis Example 5

The monomers (A), (G), (B), (F) and (C) were mixed in a molar ratio of 30/14/6/20/30 (monomer (A)/monomer (G)/monomer (B)/monomer (F)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a large amount of a mixture of methanol and water to cause precipitation. The precipitate was collected by filtration and then, was dissolved followed by poured the resultant solution into a large amount of a mixture of methanol and water to cause precipitation. This operation was repeated twice for purification. As a result, a resin having a weight-average molecular weight of about $7.2 \times 10^3$ was obtained in a yield of 78%. This resin is called as resin A5. Resin A5 had the following structural units.

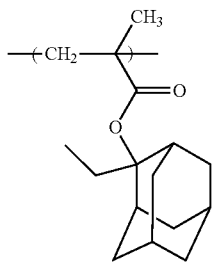
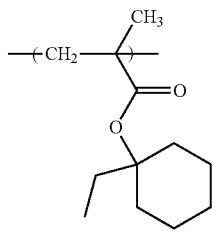
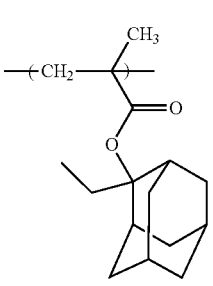
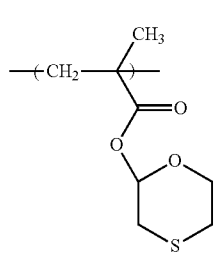

-continued

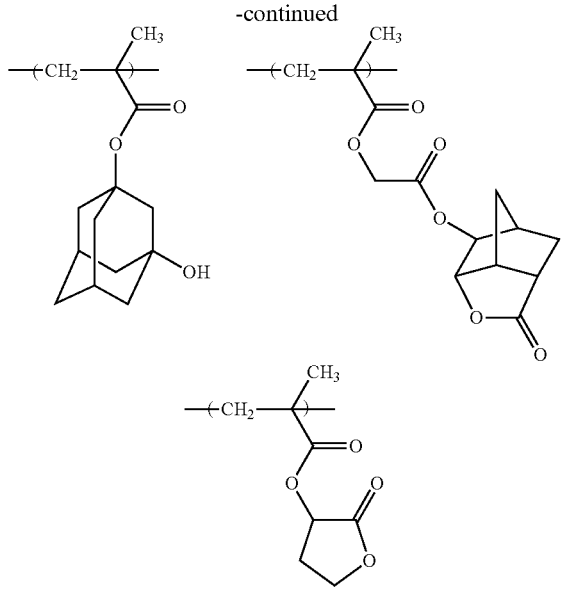

Examples 6 to 18, Comparative Example 1 and Reference Example 1

<Resin>
Resin A1, A2, A3, A4, A5
<Acid generator>
I1: Salt I1
I105: Salt I105
I9: Salt I9
I25: Salt I25
I21: Salt I21

B1:

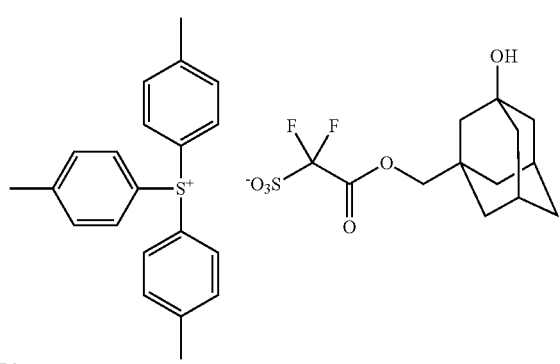

B2:

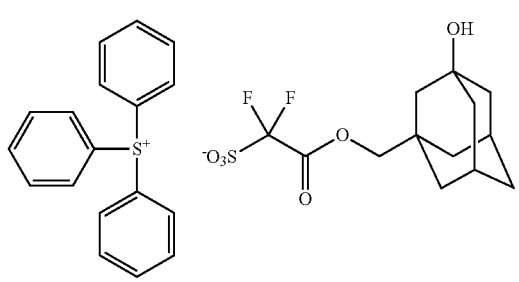

B3:

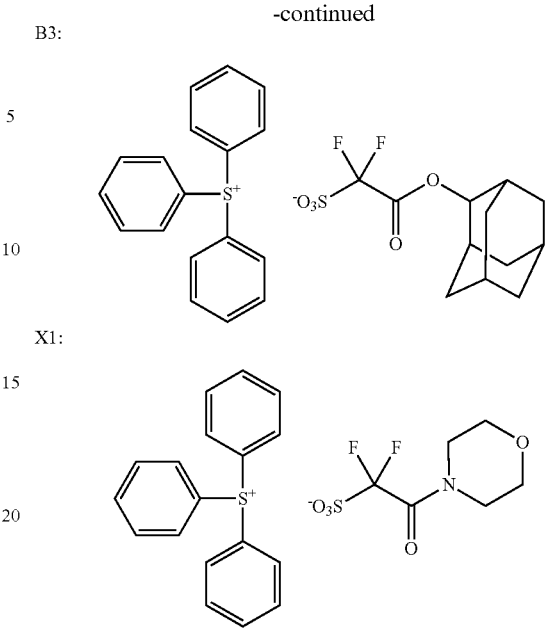

X1:

<Quencher>
C1: 2,6-diisopropylaniline

| | <Solvent> | |
|---|---|---|
| E1: | propylene glycol monomethyl ether acetate | 265 parts |
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.

Resin (kind and amount are described in Table 6) Acid generator (kind and amount are described in Table 6) Quencher (kind and amount are described in Table 6)
Solvent E1

TABLE 6

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 6 | A1/10 | I1/0.05 B1/0.85 | — | 100 | 95 |
| Ex. 7 | A2/10 | I1/0.05 B1/0.85 | — | 110 | 105 |
| Ex. 8 | A1/10 | I1/0.025 B1/0.85 | C1/0.07 | 100 | 95 |
| Ex. 9 | A2/10 | I1/0.025 B1/0.85 | C1/0.07 | 110 | 105 |
| Ex. 10 | A3/10 | I1/0.05 B3/0.85 | — | 110 | 105 |
| Ex. 11 | A3/10 | I1/0.025 B3/0.85 | C1/0.07 | 110 | 105 |
| Ex. 12 | A3/10 | I1/0.05 B2/0.85 | — | 110 | 110 |
| Ex. 13 | A4/10 | I1/0.05 B1/0.85 | — | 110 | 105 |
| Ex. 14 | A5/10 | I1/0.05 B1/0.85 | — | 110 | 105 |
| Ex. 15 | A5/10 | I105/0.05 B1/0.85 | — | 110 | 105 |

TABLE 6-continued

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 16 | A4/10 | I25/0.05 B1/0.85 | — | 110 | 105 |
| Ex. 17 | A4/10 | I21/0.05 B1/0.85 | — | 110 | 105 |
| Ex. 18 | A4/10 | I9/0.05 B1/0.85 | — | 110 | 105 |
| Comp. Ex. 1 | A3/10 | X1/0.05 B2/0.85 | — | 110 | 110 |
| Ref. Ex. 1 | A3/10 | B3/0.85 | C1/0.07 | 110 | 105 |

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each pre-baked on a direct hotplate at a temperature shown in the column "PB" in Table 6 for 60 seconds. Using an ArF excimer stepper for immersion exposure ("XT: 1900Gi" manufactured by ASML, NA=1.35, 3/4 Annular, X-Y polarization), each wafer thus formed with the respective resist film was subjected to line and space pattern exposure with the exposure quantity being varied stepwise. Ultrapure water was used as an immersion medium.

After the exposure, each wafer was subjected to post-exposure baking on a hotplate at a temperature shown in the column "PEB" in Table 6 for 60 seconds and then to paddle development for 60 seconds with an aqueous solution of 2.38% by mass tetramethylammonium hydroxide.

Each of patterns developed on the organic anti-reflective coating substrate after the development was observed with a scanning electron microscope, the results of which are shown in Table 7.

Effective Sensitivity (ES): It was expressed as the amount of exposure that the line and space pattern of 50 nm became 1:1 after exposure through line and space pattern mask and development.

Focus margin (DOF): The photoresist patterns were obtained at the exposure amount of ES, with the focal point distance being varied stepwise. Each of patterns developed on the organic anti-reflective coating substrate after the development were observed and the focal point distances when the patterns of which line width was within 50 nm±5% (about 47.5 to 52.5 nm) were measured and the difference between the max value of the focal point distance and the minimum value of the focal point distance was calculated. When the difference is more than 0.17 μm, DOF is very good and its evaluation is marked by "⊚", when the difference is more than 0.06 μm and 0.17 μm or less, DOF is good and its evaluation is marked by "○", and when the difference is 0.06 μm or less, DOF is bad and its evaluation is marked by "X". Further, each of the differences is also shown in parentheses in a column of "DOF". The difference is bigger, the better focus margin the photoresist composition has.

TABLE 7

| Ex. No. | DOF |
|---|---|
| Ex. 6 | ⊚ (0.18) |
| Ex. 7 | ⊚ (0.21) |
| Ex. 8 | ⊚ (0.18) |
| Ex. 9 | ⊚ (0.18) |
| Ex. 10 | ○ (0.12) |
| Ex. 11 | ○ (0.09) |
| Ex. 12 | ⊚ (0.18) |
| Ex. 13 | ⊚ (0.21) |
| Ex. 14 | ⊚ (0.21) |
| Ex. 15 | ○ (0.15) |
| Ex. 16 | ⊚ (0.21) |
| Ex. 17 | ⊚ (0.21) |
| Ex. 18 | ⊚ (0.21) |
| Comp. Ex. 1 | X (0.06) |
| Ref. Ex. 1 | X (0.06) |

The salt of the present invention is suitable for an acid generator and the photoresist composition comprising the acid generator comprising the salt of the present invention provides a good photoresist pattern having good focus margin (DOF).

What is claimed is:

1. A salt represented by the formula (I):

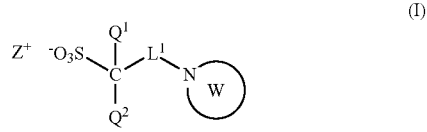

wherein $Q^1$ and $Q^2$ independently each represent a fluorine atom or a C1-C6 perfluoroalkyl group, $L^1$ represents a C1-C20 divalent saturated hydrocarbon group in which one or more —CH$_2$— can be replaced by —O— or —CO—, W represents a group represented by the formula (W1), (W2), (W3), (W4) or (W5):

(W1)

(W2)

(W3)

(W4)

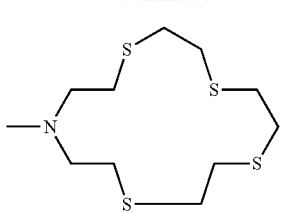

(W5)

and $Z^+$ represents an organic counter ion.

2. The salt according to claim 1, wherein W is the group represented by the formula (W1).

3. The salt according to claim 1, wherein $L^1$ is *—CO— or *—CO—O—$(CH_2)_n$— wherein * represents a binding position to —$C(Q^1)(Q^2)$- and n represents an integer of 1 to 18.

4. The salt according to claim 1, wherein $L^1$ is *—CO—O—$(CH_2)_n$— wherein * represents a binding position to —$C(Q^1)(Q^2)$- and n is 1, 2, 4, 6, 8, 10 or 12.

5. An acid generator comprising the salt according to any one of claims 1 to 4.

6. A photoresist composition comprising the acid generator according to claim 5 and a resin having an acid-labile group, being insoluble or poorly soluble in an aqueous alkali solution but becoming soluble in an aqueous alkali solution by the action of an acid.

7. The photoresist composition according to claim 6, which further comprises a basic compound.

8. The photoresist composition according to claim 6, which further comprises a solvent.

9. The photoresist composition according to claim 7, which further comprises a solvent.

10. A process for producing a photoresist pattern comprising the following steps (1) to (5):
    (1) a step of applying the photoresist composition according to claim 6 on a substrate,
    (2) a step of forming a photoresist film by conducting drying,
    (3) a step of exposing the photoresist film to radiation,
    (4) a step of baking the exposed photoresist film, and
    (5) a step of developing the baked photoresist film with an alkaline developer, thereby forming a photoresist pattern.

* * * * *